(12) United States Patent
Atwood

(10) Patent No.: US 11,474,109 B2
(45) Date of Patent: Oct. 18, 2022

(54) COMPOSITIONS AND METHODS FOR CONTROLLABLY MERGING EMULSION DROPLETS AND SAMPLE ANALYSIS

(71) Applicant: Scintimetrics, Inc., San Diego, CA (US)

(72) Inventor: Christopher Gordon Atwood, San Diego, CA (US)

(73) Assignee: Scintimetrics, Inc., San Diego, CA (US)

( * ) Notice: Subject to any disclaimer, the term of this patent is extended or adjusted under 35 U.S.C. 154(b) by 359 days.

(21) Appl. No.: 16/685,376

(22) Filed: Nov. 15, 2019

(65) Prior Publication Data

US 2020/0158736 A1    May 21, 2020

Related U.S. Application Data

(60) Provisional application No. 62/768,743, filed on Nov. 16, 2018, provisional application No. 62/768,754, filed on Nov. 16, 2018.

(51) Int. Cl.
*G01N 33/58* (2006.01)
*G01N 21/21* (2006.01)
(Continued)

(52) U.S. Cl.
CPC .......... *G01N 33/582* (2013.01); *G01N 21/21* (2013.01); *G01N 33/5434* (2013.01); *G01N 2021/216* (2013.01)

(58) Field of Classification Search
CPC .. G01N 33/582; G01N 21/21; G01N 33/5434; G01N 2021/216
See application file for complete search history.

(56) References Cited

U.S. PATENT DOCUMENTS 5,641,640 A    6/1997  Hanning
5,965,456 A   10/1999  Malmqvist
(Continued)

FOREIGN PATENT DOCUMENTS

EP    1 362 634    11/2003
EP    1 757 357     2/2007
(Continued)

OTHER PUBLICATIONS

Gammon, Snow, Shanabrook, Katzer, and Park; "Fine Structure Splitting in the Optical Spectra of Single GaAs Quantum Dots", Phys. Rev. Letters 1996, 76, 3005.
(Continued)

*Primary Examiner* — Christopher Adam Hixson
(74) *Attorney, Agent, or Firm* — Morrison & Foerster LLP

(57) ABSTRACT

The present disclosure in some aspects provides methods for the controlled merging of emulsion droplets, which can be used to assemble useful compositions such as droplets (e.g., stabilized micelles) containing a precise combination of analytes and/or analytical reagents. In some embodiments, disclosed herein is a method, e.g., for detecting the presence/absence, a level or amount, and/or an activity of an analyte in a sample, comprising merging two or more emulsion droplets such that an interaction between an analyte and an analyte-interacting reagent occurs in the merged droplet. The two or more emulsion droplets may be merged using a method for the controlled merging of emulsion droplets disclosed herein.

19 Claims, 26 Drawing Sheets

(51) Int. Cl.
*G01N 33/543* (2006.01)
*G01N 21/64* (2006.01)
*G01N 33/536* (2006.01)

(56) References Cited

U.S. PATENT DOCUMENTS

| | | | |
|---|---|---|---|
| 6,020,141 | A | 2/2000 | Pantoliano et al. |
| 6,036,920 | A | 3/2000 | Pantoliano et al. |
| 6,127,183 | A | 10/2000 | Ivarsson |
| 6,214,293 | B1 | 4/2001 | Pantoliano et al. |
| 6,493,097 | B1 | 12/2002 | Ivarsson |
| 6,589,798 | B1 | 7/2003 | Lofas |
| 6,714,303 | B2 | 3/2004 | Ivarsson |
| 6,775,003 | B2 | 8/2004 | Ivarsson |
| 6,999,175 | B2 | 2/2006 | Ivarsson |
| 7,012,694 | B2 | 3/2006 | Ivarsson |
| 7,081,958 | B2 | 7/2006 | Ivarsson |
| 7,262,866 | B2 | 8/2007 | Ivarsson |
| 7,268,167 | B2 | 9/2007 | Higuchi et al. |
| 7,373,255 | B2 | 5/2008 | Karlsson et al. |
| 7,375,140 | B2 | 5/2008 | Higuchi et al. |
| 7,717,615 | B2 | 5/2010 | Higuchi et al. |
| 7,772,287 | B2 | 8/2010 | Higuchi et al. |
| 8,741,192 | B2 | 6/2014 | Torii et al. |
| 9,658,219 | B2 | 5/2017 | Verschuren |
| 9,664,667 | B2 | 5/2017 | Walt et al. |
| 2007/0195127 | A1* | 8/2007 | Ahn .................. B01J 19/0093 347/55 |
| 2008/0011977 | A1 | 1/2008 | Atwood |
| 2011/0059435 | A1 | 3/2011 | Vogelstein et al. |
| 2012/0164680 | A1 | 6/2012 | McNaughton et al. |
| 2014/0186822 | A1 | 7/2014 | Atwood |
| 2014/0248632 | A1 | 9/2014 | Kopelman et al. |
| 2015/0010903 | A1 | 1/2015 | Schawaller et al. |
| 2015/0112612 | A1 | 4/2015 | Walt et al. |
| 2017/0336403 | A1 | 11/2017 | Atwood |
| 2020/0158736 | A1 | 5/2020 | Atwood |

FOREIGN PATENT DOCUMENTS

| | | |
|---|---|---|
| WO | WO-2002/068104 | 9/2002 |
| WO | WO-2005/089921 | 9/2005 |
| WO | WO-2021/097301 | 5/2021 |

OTHER PUBLICATIONS

Hayat, et al., "Fast Active Merging of Microdroplets in Microfluidic Chambers Driven by Photo-Isomerisation of Azobenzene Based Surfactants," Biosensors 2019, 9, 129; doi:10.3390/bios9040129.

A. Kulesa, J. Kehe, J. Hurtado, P Tawde, P. Blainey, "Combinatorial Drug Discovery in Nanoliter Droplets", Proceedings of the National Academy of Sciences, 115 (26) 6685-6690, Jun. 26, 2018.

Pouya, Koochesfahani, Snce, Bawendi, and Nocera; "Single Quantum Dot Imaging of Fluid Flow Near Surface", Experiments in Fluids, published Oct. 2005.

Yu, et al., "A Facile Approach to Fabrication of Bifunctional Magnetic-Optical $Fe_3O_4$@ZnS Microspheres", *Chem. Mater.* 2009, 21, 4892-4898.

H. Zhang, L. Sepunaru, S. Sokolov, et al. in "Electrochemistry of single droplets of inverse (water-in-oil) emulsions", Phys. Chem. Chem. Phys. 2017, 19, 15662-15666.

* cited by examiner

COMPOSITIONS AND METHODS FOR CONTROLLABLY MERGING EMULSION DROPLETS AND SAMPLE ANALYSIS

CROSS-REFERENCE TO RELATED APPLICATIONS

This application claims benefit of priority to U.S. Provisional Application No. 62/768,743, filed Nov. 16, 2018, entitled "Methods for the Detection of Analyte Concentrations and Binding Interactions," and U.S. Provisional Application No. 62/768,754, filed Nov. 16, 2018, entitled "Methods for Controlled Merging of Emulsion Droplets," the contents of which applications are herein incorporated by reference in their entireties for all purposes.

FIELD

The present disclosure relates in some aspects to compositions and methods for controlled merging of emulsion droplets, e.g., for analyzing one or more analyte in a sample, such as a biological sample. In some aspects, the compositions and methods disclosed herein are useful in biomarker discovery and disease diagnosis.

BACKGROUND

Samples of complex biological media, such as blood, contain specific components that are useful in diagnosing illnesses. The concentrations of these specific components need to be measured reliably despite the concomitant presence of much larger concentrations of similar components. Methods for measuring concentrations of these specific components are known. Said specific components are referred to as "analytes," and may comprise proteins, small molecules, or nucleic acids. Measurement is commonly achieved by the use of complementary components that bind to the analytes. Said complementary components are referred to as "analyte binding reagents." An example of an analyte and analyte binding reagent pair is an antigen and antibody.

Some of these analytes may be biologically significant at presently undetectable concentrations, necessitating new techniques that have a high intrinsic sensitivity and specificity. Additionally, the complexity of the media increases the risk of false positives and false negatives, which may be ameliorated by new techniques for disease marker diagnostics. Additionally, discovery of new disease markers and discovery of new drug therapies are research areas that would benefit from improved methods. The present disclosure addresses these and other needs.

SUMMARY

In some embodiments, provided herein is a method for analyzing an analyte, comprising: contacting (i) a first emulsion comprising a first aqueous droplet in a first liquid matrix, with (ii) a second emulsion comprising a second aqueous droplet in a second liquid matrix, wherein the first aqueous droplet comprises an analyte and the second aqueous droplet comprises a reagent, under conditions that allow the first aqueous droplet to merge with the second aqueous droplet to form a merged droplet, wherein an interaction or a reaction in the merged droplet involving the analyte and the reagent generates a detectable signal.

In some embodiments, the detectable signal is detected for analyzing the presence or absence, an amount or concentration, and/or an activity of the analyte in a sample.

In any of the preceding embodiments, the first aqueous droplet can have a first net ionic charge, and the second aqueous droplet can have a second net ionic charge that is the opposite of the first net ionic charge.

In any of the preceding embodiments, the first aqueous droplet can comprise a first charged surfactant and the second aqueous droplet can comprises a second charged surfactant of opposite charge from the charge of the first charged surfactant.

In any of the preceding embodiments, the reagent can comprise a fluorescent label.

In any of the preceding embodiments, the reagent can comprise a magnetic label.

In any of the preceding embodiments, the contacting step can comprise mixing streams of the first emulsion and the second emulsion and at least one demulsifying agent.

In any of the preceding embodiments, the contacting step can comprise mixing streams of the first emulsion and the second emulsion and at least one surfactant.

In any of the preceding embodiments, the detectable signal can comprise a fluorescent signal, which may be optionally induced by a non-polarized excitation light, a linearly polarized excitation light, a circularly polarized excitation light, an elliptically polarized excitation light, a non-coherent excitation light, a coherent excitation light, a continuous excitation light, a pulsed excitation light, an excitation light applied at a single incident angle, or an excitation light applied at a set of incidence angles.

In any of the preceding embodiments, the method can further comprise applying an external electric field to the merged droplet to modify the distribution of the electric field vector of an evanescent wave within each droplet and thereby affect fluorescence emission.

In any of the preceding embodiments, the method can further comprise applying an external electric field to distort the merged droplet.

In any of the preceding embodiments, the reagent can comprise a fluorescent particle and can specifically bind to the analyte.

In any of the preceding embodiments, the first and second emulsions can be mixed on a surface in an analytical chamber, thereby allowing the first and second aqueous droplets to form the merged droplet on the surface, and allowing the reagent to specifically bind to the analyte in the merged droplet.

In any of the preceding embodiments, the method can further comprise applying an excitation light at an angle sufficient to produce total internal reflection on the surface during said mixing process sufficient to cause fluorescence of the fluorescent particle, wherein said fluorescence is dependent on fluorescent particle position within the electric field vector of an evanescent wave that arises from a refractive index difference between said flat surface and the aqueous droplet.

In any of the preceding embodiments, the method can further comprise detecting and/or measuring the magnitude of the fluorescence emission during said mixing process; and determining the identity of reagent used within each droplet from the pattern of fluorescent emission wavelengths from each droplet, wherein a change in the stochastic behavior of the magnitude of the fluorescence emission provides an indication of analyte presence/absence, amount or concentration, and/or binding interaction.

In any of the preceding embodiments, the first and second emulsions can be mixed to form a combined emulsion wherein the merged droplet is in suspension in the combined emulsion.

In any of the preceding embodiments, the method can further comprise applying an excitation light during said mixing process sufficient to cause fluorescence of the fluorescent particle, wherein said fluorescence is dependent on fluorescent particle position within the electric field vector of an evanescent wave that arises from a refractive index difference between said liquid matrix and the aqueous droplet.

In any of the preceding embodiments, the method can further comprise detecting and/or measuring the magnitude of the fluorescence emission during said mixing process; and determining the identity of reagent used within each droplet from the pattern of fluorescent emission wavelengths from each droplet, wherein a change in the stochastic behavior of the magnitude of the fluorescence emission provides an indication of analyte presence/absence, amount or concentration, and/or binding interaction.

In any of the preceding embodiments, the merging of the first and second aqueous droplets can be controlled, and the controlled merging can be provided by: (i) the first aqueous droplet comprising a first redox species and the first liquid matrix comprising a first electrolyte, the second aqueous droplet comprising a second redox species and the second liquid matrix comprising a second electrolyte, wherein the first and second aqueous droplets are each contacted with an electrode to cause charge transfer between the aqueous droplet and the electrode; (ii) the first emulsion stabilized with a first charged surfactant, and the second emulsion stabilized with a second charged surfactant of opposite charge from that of the first charged surfactant; (iii) contacting the first emulsion with a positive electrode sufficient to cause electrostatic charging of the first aqueous droplet, and contacting the second emulsion with a negative electrode sufficient to cause electrostatic charging of the second aqueous droplet; and/or (iv) the first aqueous droplet comprising a first magnetic particle, the second aqueous droplet comprising a second magnetic particle, wherein an external magnetic field is applied to produce an attractive force between said first magnetic particle and said second magnetic particle.

In some embodiments, provided herein is a method for controlled merging of emulsion droplets, comprising contacting (i) a first emulsion comprising a first aqueous droplet in a first liquid matrix, with (ii) a second emulsion comprising a second aqueous droplet in a second liquid matrix, under conditions that allow the first aqueous droplet to merge with the second aqueous droplet to form a merged droplet, wherein the merging is controlled and is provided by: (i) the first aqueous droplet comprising a first redox species and the first liquid matrix comprising a first electrolyte, the second aqueous droplet comprising a second redox species and the second liquid matrix comprising a second electrolyte, wherein the first and second aqueous droplets are each contacted with an electrode to cause charge transfer between the aqueous droplet and the electrode; (ii) the first emulsion stabilized with a first charged surfactant, and the second emulsion stabilized with a second charged surfactant of opposite charge from that of the first charged surfactant; (iii) contacting the first emulsion with a positive electrode sufficient to cause electrostatic charging of the first aqueous droplet, and contacting the second emulsion with a negative electrode sufficient to cause electrostatic charging of the second aqueous droplet; and/or (iv) the first aqueous droplet comprising a first magnetic particle, the second aqueous droplet comprising a second magnetic particle, wherein an external magnetic field is applied to produce an attractive force between said first magnetic particle and said second magnetic particle.

BRIEF DESCRIPTION OF THE DRAWINGS

Embodiments in accordance with the present disclosure are described, by way of example only, with reference to the accompanying drawings.

DETAILED DESCRIPTION

Figure 1:
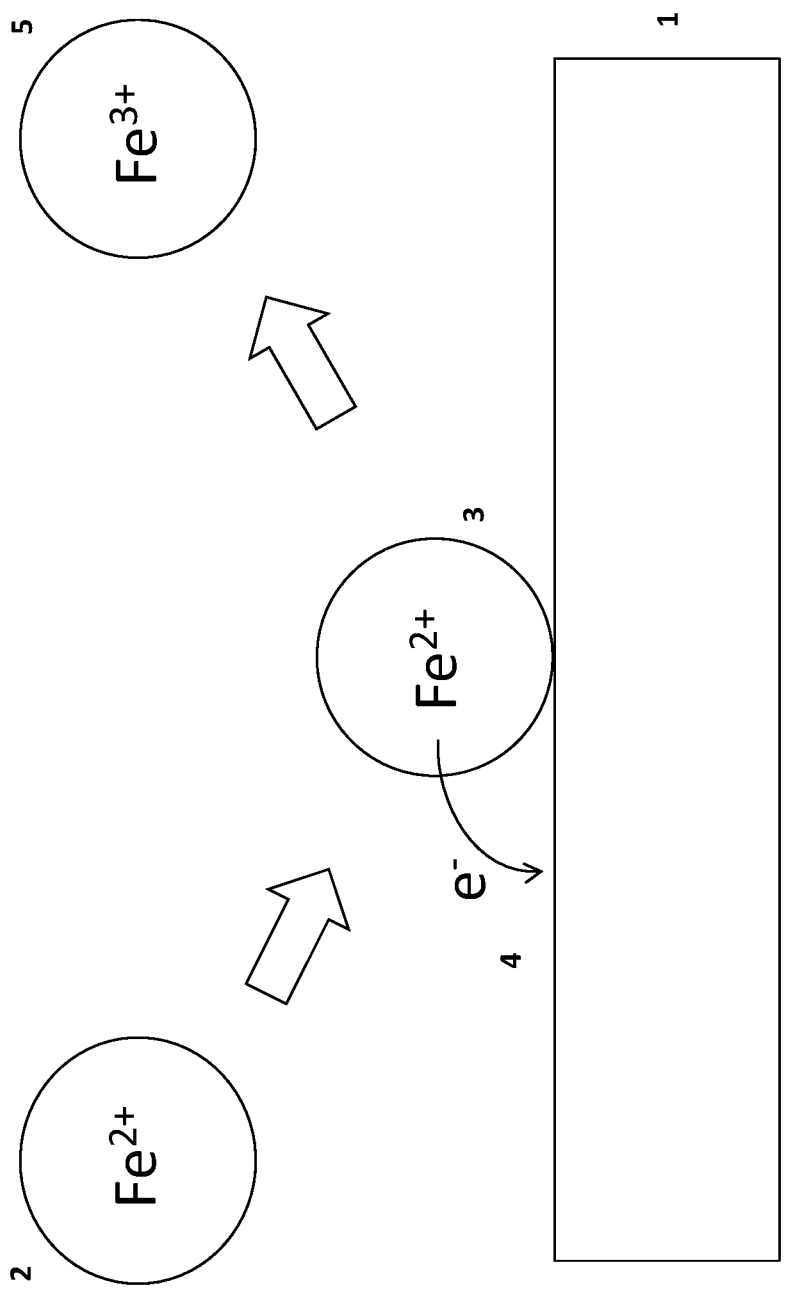
FIG. 1 shows an electrode performing charge transfer with an aqueous droplet within a water-immiscible host matrix, according to certain embodiments of the present disclosures.

Embodiments of the present disclosure are overviewed, and examples in accordance with various embodiments are described. Throughout this patent specification, like reference numerals are used to denote like parts. The examples and embodiments are provided to facilitate understanding of the invention, and are not intended to limit its scope.

In some embodiments, a method disclosed herein comprises using a heterogeneous assay format, e.g., one which uses a fixed surface of analyte binding reagents exposed to a solvated sample. In some embodiments, a method disclosed herein comprises the use of a homogeneous assay format, e.g., one which uses entirely solvated analyte binding reagents and samples.

Various aspects of the following exemplary assays may be included or excluded from the presently disclosed assay compositions and methods without departing from the true scope and spirit of the disclosure. Such embodiments with various aspects of the following exemplary assays included or excluded are intended to fall within the scope of the present disclosure.

One exemplary assay involves the use of electrodes, where analytes bind specifically to an electrode surface that has been derivatized with a reagent that binds to an analyte contained in a sample. This binding interaction alters the electron-transport behavior of the electrode in a manner that allows determination of the analyte presence or concentration.

A second exemplary assay is Enzyme Linked Immuno Sorbent Assay (ELISA). ELISA uses a fixed surface that is coated with an array of differing analyte binding reagents, which is typically exposed to a labeled sample for 30 to 120 minutes, rinsed, and then scanned for bound label. The labels can be fluorescent, radioactive, magnetic, or have some other detectable property. For fluorescent markers, rinsing can be avoided by having the fixed surface be transparent, and using an evanescent field, e.g., as described in Patent Application US2015/0010903A1.

A third exemplary assay is Surface Plasmon Resonance (SPR), such as that used by Biacore. SPR uses a fixed surface that is coated with an array of differing analyte binding reagents, exposed to a sample for several minutes, and then scanned for surface plasmon resonance. Total internal reflection from the array produces quantitative variations in the reflection angle, e.g., as described in U.S. Pat. Nos. 7,373,255, 7,262,866, 7,081,958, 7,012,694, 6,999,175, 6,775,003, 6,714,303, 6,589,798, 6,493,097, 6,127,183, 5,965,456, and 5,641,640.

A fourth exemplary assay is a homogeneous assay. These include agglutination assays and Fluorescence Resonance Energy Transfer (FRET) assays. Additionally, there is Differential Scanning Fluorimetry (DSF), such as that used by ThermaFluor. DSF uses a hydrophobic fluorescent dye that embeds within the hydrophobic center of a protein, which becomes exposed to the aqueous solvent as the temperature is raised and the protein molecule melts. This exposure unquenches the fluorescent dye. Reagents that bind to the protein affect the melting point, and thus the temperature at which fluorescence is unquenched. This provides an analytical signal for the binding interaction, e.g., as described in U.S. Pat. Nos. 6,214,293, 6,036,920, and 6,020,141.

A fifth exemplary assay involves the use of particles that are both fluorescent and magnetic, and can bind to analytes, e.g., as described in U.S. Pat. No. 9,658,219, where the particles are allowed to bind to analytes, are magnetically immobilized on a surface containing an evanescent wave, and are detected by optical attenuation or fluorescence.

A sixth exemplary assay involves the use of derivatized fluorescent quantum dots that can bind to particular analytes, e.g., as described in U.S. Pat. No. 9,664,667, where the quantum dots are allowed to bind to analytes, are placed near a surface containing an evanescent wave, and are detected individually by optical measurement. Brownian movement of each quantum dot causes it to move stochastically in and out of the evanescent field, at a certain diffusion rate. This movement produces corresponding variations in the fluorescence intensity of the particle. Optical tracking provides a measure of the diffusion rate of the quantum dot. The diffusion rate is affected by the binding interaction, where the binding interaction tends to increase the effective size of the quantum dot and reduce its diffusion rate. The combinatorial address space is constrained by the limited number of distinct colors of quantum dots. A larger address space may be attained by the use of heterogeneous structures composed of different quantum dots. Such heterogeneous structures are difficult to synthesize with a uniform composition and diffusivity, e.g., as described by Yu, Wan, et al. (2009). The fluorescence bands are broadened, the fluorescence quantum yield is reduced, and the larger size reduces sensitivity for measurements of binding interaction. Aside from the use of such heterogeneous structures, a description of how to enlarge the address space is not obvious. Also, a description of how to measure the transition in diffusivity during a binding interaction is not obvious. Lastly, a description of how to measure association and dissociation constants for the binding interaction is not obvious.

A seventh exemplary assay involves the use of aqueous emulsions to contain the sample and transport it to measurement apparatus, e.g., as described in Patent publication WO2002/068104 (including U.S. Pat. Nos. 7,268,167, 7,772,287, 7,717,615, and 7,375,140) and Patent publication WO2005/089921 (including U.S. Pat. No. 8,741,192) of the Japan Science and Technology Agency.

An eighth exemplary assay involves the use of aqueous emulsions to measure the effectiveness of antibiotics with synergistic compounds against a variety of bacteria, e.g., as described by Kulesa, Kehe, et al. (2018). Random pairs of droplets are contained within chambers, stimulated to merge using an electric field, and then each resulting merged droplet observed over time for the behavior of an entrapped bacterium. Droplets are labeled with a set of quantum dots, which allows identification of the antibiotics, compounds, and bacteria present in each droplet. This requires the use of a fixed array of chambers, each containing a random pair of droplets, in order to achieve a binary pairing of droplets.

In contrast, the present disclosure avoids the requirement for a fixed array, and instead uses binary interactions without pair containment. This allows a simpler analytic chamber with a random array of droplets, e.g., as described in the various embodiments provided herein.

In some embodiments, a method disclosed herein is applicable to disease marker diagnostics, discovery of the disease markers, discovery of drug therapies, and evaluation of drug therapies. In some embodiments, provided herein is a method to detect the presence of an analyte in a sample, which comprises: providing a first emulsion that comprises a first aqueous droplet in a first liquid matrix, wherein the first aqueous droplet comprises a portion of the sample; providing a second emulsion that comprises a second aqueous droplet in a second liquid matrix, wherein the second aqueous droplet comprises an analyte binding reagent; contacting the first emulsion with the second emulsion to form a combined emulsion under conditions that allow the first aqueous droplet to merge with the second aqueous droplet to form a merged droplet; and detecting a signal generated by a binding interaction of the analyte with the analyte binding reagent.

In some embodiments, provided herein is a method for detection of an analyte interacting with an analyte binding reagent, comprising: providing a first emulsion comprising aqueous sample droplets within a water-immiscible host matrix, stabilized with a charged surfactant, wherein the sample droplets comprise the analyte; providing a second emulsion comprising aqueous reagent droplets within a water-immiscible host matrix, stabilized with a surfactant of opposite charge, wherein the reagent droplets contain one or more fluorescent particles, where each fluorescent particle has a unique analyte binding reagent surface; mixing of both emulsions together at a flat surface in an analytic chamber and allowing said droplets to merge into merged droplets; asserting excitation light at an angle sufficient to produce total internal reflection at said flat surface during said mixing process sufficient to cause fluorescence of the said fluorescent particle, wherein said fluorescence is dependent on fluorescent particle position within the electric field vector of an evanescent wave that arises from a refractive index difference between said flat surface and the droplet; detecting and/or measuring the magnitude of the fluorescence emission during said mixing process; determining the identity of the analyte binding reagent used within each droplet from the pattern of fluorescent emission wavelengths from each droplet, wherein a change in the stochastic behavior of the magnitude of the fluorescence emission provides an indication of analyte presence, concentration, and/or binding interaction.

In some embodiments, provided herein is a method for detection of an interaction between an analyte in a sample and an analyte binding reagent, wherein the method comprises: providing a first aqueous emulsion comprising droplets containing a portion of the sample in a water-immiscible host matrix, wherein the emulsion is stabilized with a charged surfactant; providing a second aqueous emulsion comprising one or more analyte binding reagents in droplets in a water-immiscible host matrix, where each analyte binding reagent is on the surface of a fluorescent particle, wherein the second aqueous emulsion is stabilized with a surfactant having the opposite charge from that of the charged surfactant in the first aqueous emulsion; mixing the first and second aqueous emulsions together to form a combined emulsion under conditions where droplets from the first emulsion can combine with droplets from the second emulsion to form merged droplets; directing excitation light to the combined emulsion during and/or after mixing, sufficient to cause fluorescence of said fluorescent particles, wherein said fluorescence is dependent on the position of each fluorescent particle within the electric field vector of an evanescent wave that arises from a refractive index difference between the host matrix and the droplet; detecting the fluorescence emission and/or measuring the magnitude of the fluorescence emission from the merged droplets; and determining the identity of each analyte binding reagent within each merged droplet from the pattern of fluorescent emission wavelengths from each merged droplet, wherein a change in the stochastic behavior of the magnitude of the fluorescence emission provides an indication of analyte presence, concentration, and/or binding interaction.

In any of the preceding embodiments, the method can use an emulsion of aqueous sample droplets containing analytes that is mixed with an emulsion of aqueous reagent droplets (droplets comprising an analyte binding reagent). In any of the preceding embodiments, the sample droplets can contain analytes to be measured. In any of the preceding embodiments, the sample droplet surfaces can be stabilized with a surfactant, e.g., a cationic surfactant. In any of the preceding embodiments, the reagent droplets each can contain at least a single fluorescent particle, and can have a surface comprising a reagent that can bind to said analytes. In any of the preceding embodiments, the reagent droplet surfaces can be stabilized with an anionic surfactant (surfactant of opposite charge relative to the surfactant used in the sample droplets). In some embodiments, upon mixing of the two emulsions together, oppositely-charged pairs of droplets can merge together to form neutrally-charged merged droplets of summed mass, which mixes the analytes with the fluorescent particle and allows a binding interaction to occur. In some embodiments, during the mixing process, excitation light illuminates both emulsions, producing fluorescence emission which is continuously monitored and tracked for each fluorescent particle. In some embodiments, due to refraction and diffraction at the surface of each droplet, the magnitude of the electric field vector of the excitation light is not uniform across the droplet internal volume. In some embodiments, as Brownian motion moves the fluorescent particle within a droplet, its fluorescence varies with the magnitude of the local electric field vector. In some embodiments, the movement is affected by a binding interaction with an analyte, and hence affects the stochastic behavior of the magnitude of the fluorescence emission. In some embodiments, the transition in the stochastic behavior of the magnitude of the fluorescence emission during each droplet merge event constitutes a measurement of the analyte.

The methods disclosed herein find widespread applicability for disease marker diagnostics of complex biological media. Additionally, such methods may also be used for disease marker discovery, drug discovery, and drug evaluation, where the sample is known and less complex. A strong advantage of these methods over existing methods is that the methods disclosed herein are easily scaled to arbitrarily large parallelization without restriction to fixed plate arrays. These methods are also independent of pH or other solution characteristics, can be used with opaque samples, and can use extremely small sample volumes with minimal transport loss.

The methods disclosed herein can be used to detect the presence, absence, or degree of binding interactions between analytes and analyte binding reagents, and to determine the presence, absence or amount (e.g., concentration) of analytes in samples.

These methods are useful for the discovery and characterization of binding interactions between known analytes and known analyte binding reagents, and useful for diagnosing the presence of analytes in biological samples. Current methods for performing these tasks suffer from a variety of deficiencies, such as the speed of analysis, limitation on array size, requirement for large sample volumes, and analyte handling losses. These methods described herein address many of these limitations and provide a new way to detect intermolecular interactions and measure analytes of various types, including ones having clinical significance and/or diagnostic relevance. The use of emulsions instead of fixed array plates allows the formation of arrays of arbitrary size, allows the sample volume to be small, and avoids having the sample contact plumbing surfaces that can adsorb analytes. The mixing occurs over short timescales during which the binding interaction process can be monitored.

A specific field where these methods would be useful is in biotechnology, for the measurement of protein interactions. There are an extremely large number of proteins used in every biological system, which interact in a complex network that is dependent on many factors. Diseases distort this network, adding or removing components and interaction pathways. An understanding of these systems allows early diagnosis of disease, and a way to chemically repair the system through drug therapy. The most populous and stable proteins within these systems have been partially studied, but much further study is warranted. The addition of new and more powerful tools, such as the methods described herein, to the repertoire of medical researchers would deepen the understanding of the protein networks and allow the development of new diagnostics and new drug therapies.

I. COMPOSITIONS AND METHODS FOR CONTROLLED MERGING OF EMULSION DROPLETS

In some aspects, disclosed herein are methods for the controlled merging of emulsion droplets, which can be used to assemble useful compositions such as droplets (e.g., stabilized micelles) containing a precise combination of analytes and/or analytical reagents, such as proteins, binding reagents, particles, and detectable labels.

In some embodiments, emulsions of water droplets in a water-immiscible host matrix are used, e.g., as or in a useful system, for handling aqueous samples. In some embodiments, the benefits of using such a system include not contacting the sample with the large inner surface area of the walls of liquid-handling equipment, usage of extremely small volumes, and the ability to have a large number of disparate samples within an analytical device. In some embodiments, these benefits are particularly important with biological samples, where trace amounts of an analyte (e.g., a protein) can be adsorbed onto tubing surfaces and never be detected, only very small amounts of the analyte e.g., a protein) can be obtained, and the need to test binding interactions, e.g., of a protein molecule against a large library of antigens.

In some aspects, the methods described herein use an electrically charged emulsion of aqueous droplets that is mixed with an oppositely-charged emulsion of aqueous droplets to provide binary merging of oppositely-charged droplets. Electrical charging is produced by either an electrochemical method, by the use of a surfactant method, or by an electrostatic method. Electrochemical charging is achieved by applying droplets to an electrode surface and allowing a charge transfer to occur between the electrode surface and a redox species within the droplet. Surfactant charging is achieved by use of charged surfactants that produce a surface charge on each droplet. Electrostatic charging is achieved by applying droplets to a highly charged electrode that transfers an electrostatic charge onto each droplet. Upon mixing of the two emulsions together, oppositely-charged pairs of droplets may merge together to form neutrally-charged merged droplets of summed mass, which mixes the contents of the droplets.

In some embodiments, the methods described herein are applicable to controlled merging of emulsion droplets. In some embodiments, the methods use two separate emulsions of aqueous droplets within a water-immiscible host matrix, where the droplets have been modified, such as being electrically charged with opposite polarities. In some embodiments, combining the two separate emulsions causes the opposing charges to attract, thereby causing contact, and finally merging of oppositely-charged pairs in a merge event. Like-charged droplets would repel each other and not merge, thus the composition of the merged droplet products is controlled. In some embodiments, the contents of the two droplets become mixed by turbulence and diffusion in the merged droplet after the merge event. In some embodiments, the droplets comprise fluorescent markers which can be optically identified and tracked within a complex mixture throughout the merge event.

In some embodiments, electrical charging is performed on the resulting droplet of the merge event, followed by a subsequent merge event with a third emulsion. In this manner, a large number of controlled droplet combinations can be performed.

In some embodiments, the methods disclosed herein find widespread applicability for generation of emulsions containing specific combinations of materials in aqueous solution and suspension. For example, the methods allow the formation an emulsion where each droplet contains a different antibody and a unique combination of quantum dots in free suspension that can serve as a tracking label or unique fingerprint that identifies the contents of the droplet. This would effectively be a library-in-a-vial that could be used for disease marker discovery, drug discovery, and drug evaluation.

The following enumerated embodiments represent selected aspects of the invention. While these are often described as "comprising" specified features and/or steps, the invention also includes corresponding embodiments "consisting essentially of" and embodiments "consisting of" the specified features and/or steps.

Embodiment 1

A method for controlled merging of emulsion droplets, comprising: (a) providing a first emulsion comprising aqueous droplets containing a first redox species within a first water-immiscible host matrix containing a first electrolyte; (b) contacting said first emulsion with an anode of an electrochemical cell sufficient to cause charge transfer with the aqueous droplets of the first emulsion; (c) providing a second emulsion comprising aqueous droplets containing a second redox species within a second water-immiscible host matrix containing a second electrolyte; (d) contacting said second emulsion with a cathode of an electrochemical cell sufficient to cause charge transfer with the aqueous droplets of the second emulsion; (e) mixing said first and second emulsions together to form a combined emulsion, wherein droplets from the first emulsion selectively combine with droplets from the second emulsion to form merged droplets.

Embodiment 2

The method of Embodiment 1, wherein said first emulsion has droplets at least partially coated with a surfactant selected from the group consisting of: nonionic surfactant; amphoteric surfactant; anionic surfactant; cationic surfactant; membrane protein; and no surfactant.

Embodiment 3

The method of Embodiment 1 or 2, wherein said second emulsion has droplets at least partially coated with a surfactant selected from the group consisting of: nonionic surfactant; amphoteric surfactant; anionic surfactant; cationic surfactant; membrane protein; and no surfactant.

Embodiment 4

The method of any one of Embodiments 1-3, wherein said first water-immiscible matrix and said second water-immiscible host matrix are the same, and said water-immiscible host matrix contains a gelling agent that reversibly gels the water-immiscible host matrix below a temperature selected from the group consisting of: 10 degrees Celsius; 20 degrees Celsius; 30 degrees Celsius; 40 degrees Celsius; and 50 degrees Celsius.

Embodiment 5

The method of any one of the preceding Embodiments, wherein said first and/or second redox species are contained within a water-immiscible droplet that is itself within an aqueous droplet of a secondary emulsion.

Embodiment 6

The method of any one of the preceding Embodiments, wherein the aqueous droplets of the first emulsion contain a first cargo, and the aqueous droplets from the second emulsion contain a second cargo, and combining the first and second emulsions selectively forms merged droplets that contain both the first cargo and the second cargo.

Embodiment 7

The method of Embodiment 6, wherein the first cargo and the second cargo are different.

Embodiment 8

The method of Embodiment 6 or Embodiment 7, wherein the first cargo comprises a compound or particle capable of producing a fluorescent signal.

Embodiment 9

The method of Embodiment 8, wherein the second cargo comprises an analyte.

Embodiment 10

The method of Embodiment 9, wherein the analyte is a protein, bioactive small molecule, or polynucleotide.

Embodiment 11

A method for controlled merging of emulsion droplets, comprising: (a) providing a first emulsion comprising aqueous droplets within a first water-immiscible host matrix, stabilized with a first charged surfactant; (b) providing a second emulsion comprising aqueous droplets within a second water-immiscible host matrix, stabilized with a second surfactant of opposite charge from that of the first charged surfactant; (c) mixing the first and second emulsions together to form a combined emulsion, wherein droplets from the first emulsion selectively combine with droplets from the second emulsion to form merged droplets.

Embodiment 12

The method of Embodiment 11, wherein said water-immiscible host matrix contains a gelling agent that reversibly gels the water-immiscible host matrix below a temperature selected from the group consisting of: 10 degrees Celsius; 20 degrees Celsius; 30 degrees Celsius; 40 degrees Celsius; and 50 degrees Celsius.

Embodiment 13

A method for controlled merging of emulsion droplets, comprising: (a) providing a first emulsion comprising aqueous droplets; (b) contacting said first emulsion with a positive electrode of an electrostatic cell sufficient to cause electrostatic charging of the aqueous droplets of the first emulsion; (c) providing a second emulsion comprising aqueous droplets; (d) contacting said second emulsion with a negative electrode of an electrostatic cell sufficient to cause electrostatic charging of the aqueous droplets of the second emulsion; (e) mixing of both emulsions together, wherein droplets from the first emulsion selectively combine with droplets from the second emulsion to form merged droplets.

Embodiment 14

The method of Embodiment 13, wherein said first emulsion has droplets coated with a surfactant selected from the group consisting of: (a) nonionic surfactant; (b) amphoteric surfactant; (c) anionic surfactant; (d) cationic surfactant; (e) membrane protein; and (f) no surfactant.

Embodiment 15

The method of Embodiment 13, wherein said second emulsion has droplets coated with a surfactant selected from the group consisting of: nonionic surfactant; amphoteric surfactant; anionic surfactant; cationic surfactant; membrane protein; and no surfactant.

Embodiment 16

The method of Embodiment 13, wherein said water-immiscible host matrix contains a gelling agent that reversibly gels the water-immiscible host matrix below a temperature selected from the group consisting of: 10 degrees Celsius; 20 degrees Celsius; 30 degrees Celsius; 40 degrees Celsius; and 50 degrees Celsius.

Embodiment 17

A method for controlled merging of emulsion droplets, comprising: (a) providing a first emulsion comprising aqueous droplets that contain a first cargo and have a positive charge and are suspended in a first water-immiscible host matrix; (b) providing a second emulsion comprising aqueous droplets that contain a second cargo and have a negative charge and are suspended in a second water-immiscible host matrix; (c) mixing said first emulsion and said second emulsion together to form a combined emulsion, wherein aqueous droplets from the first emulsion selectively combine with aqueous droplets from the second emulsion to form merged droplets that contain both the first cargo and the second cargo.

Embodiment 18

The method of Embodiment 17, wherein said water-immiscible host matrix contains a gelling agent that reversibly gels the water-immiscible host matrix below a temperature selected from the group consisting of: 10 degrees Celsius; 20 degrees Celsius; 30 degrees Celsius; 40 degrees Celsius; and 50 degrees Celsius.

Embodiment 19

The method of Embodiment 17 or 18, wherein the method of any one of Embodiments 1, 11, and 13, or a combination thereof, is used to provide positive charge or negative charge within the droplets of the emulsions.

Embodiment 20

A method for controlled merging of emulsion droplets, comprising: (a) providing a first emulsion comprising aqueous droplets containing a first magnetic particle within a first water-immiscible host matrix; (b) providing a second emulsion comprising aqueous droplets containing a second magnetic particle within a second water-immiscible host matrix; (c) mixing said first and second emulsions together to form a combined emulsion; (d) applying an external magnetic field sufficient to produce an attractive force between said first magnetic particle and said second magnetic particle, wherein droplets from the first emulsion selectively combine with droplets from the second emulsion to form merged droplets.

Embodiment 21

The method of Embodiment 20, wherein said first magnetic particle has an electric charge.

Embodiment 22

The method of Embodiment 20, wherein said second magnetic particle has an electric charge.

Embodiment 23

The method of Embodiment 20, wherein said first emulsion has droplets at least partially coated with a surfactant selected from the group consisting of: nonionic surfactant; amphoteric surfactant; anionic surfactant; cationic surfactant; membrane protein; and no surfactant.

Embodiment 24

The method of any one of Embodiments 20-23, wherein said second emulsion has droplets at least partially coated with a surfactant selected from the group consisting of: nonionic surfactant; amphoteric surfactant; anionic surfactant; cationic surfactant; membrane protein; and no surfactant.

Embodiment 25

The method of any one of the preceding embodiments, wherein said first water-immiscible matrix and said second water-immiscible host matrix are the same, and said water-immiscible host matrix contains a gelling agent that reversibly gels the water-immiscible host matrix below a temperature selected from the group consisting of: 10 degrees Celsius; 20 degrees Celsius; 30 degrees Celsius; 40 degrees Celsius; and 50 degrees Celsius.

Embodiment 26

The method of any one of the preceding embodiments, wherein said first and/or second magnetic particles are contained within a water-immiscible droplet that is itself within an aqueous droplet of a secondary emulsion.

Embodiment 27

The method of any one of the preceding embodiments, wherein the aqueous droplets of the first emulsion contain a first cargo, and the aqueous droplets from the second emulsion contain a second cargo, and combining the first and second emulsions selectively forms merged droplets that contain both the first cargo and the second cargo.

Embodiment 28

The method of Embodiment 27, wherein the first cargo and the second cargo are different.

Embodiment 29

The method of Embodiment 27 or Embodiment 28, wherein the first cargo comprises a compound or particle capable of producing a fluorescent signal.

Embodiment 30

The method of any one of Embodiments 27 to 29, wherein the second cargo comprises an analyte.

Embodiment 31

The method of Embodiment 30, wherein the analyte is a protein, bioactive small molecule, or polynucleotide.

Additional exemplary embodiments are described below.
A. Emulsion Comprising Redox Species
In some aspects, provided herein is a first emulsion comprising aqueous droplets that contain a first redox species in a first water-immiscible host matrix. In some embodiments, the method comprises a step of generating or providing the first emulsion.

In some embodiments, the first emulsion is contacted with the anode of an electrochemical cell, under conditions that cause droplets in the first emulsion to take on a positive charge.

In some aspects, provided herein is a second emulsion comprising aqueous droplets that contain a second redox species in a second water-immiscible host matrix. In some embodiments, the method comprises a step of generating or providing the second emulsion.

In some embodiments, the second emulsion is contacted with the cathode of the same cell under conditions that cause droplets in the second emulsion to take on a negative charge. In some embodiments, droplets within both emulsions are electrochemically charged but with opposite charges. In some embodiments, the two emulsions are then mixed together. In some embodiments, droplets of opposite electrochemical charge are attracted to each other and merge, while little or no merging of like-charged droplets occurs. In some embodiments, the method thus causes preferential merging of droplets that originated in different emulsions. The result is a combined emulsion wherein each droplet contains the aqueous content of a droplet from the first emulsion mixed with the aqueous content of a droplet from the second emulsion. In some embodiments, the merging of oppositely-charged droplets substantially eliminates the electrochemical charges, thus producing a combination emulsion selectively containing primarily merged droplets from the first and second emulsions.

For example, an emulsion X is formed using methods known in the art. An example of a method well known in the art is to combine a slow flow of aqueous media with a fast flow of water-immiscible media within a flow cell. This generates aqueous droplets having a highly uniform size within a water-immiscible host matrix. Secondary emulsions that are composed of a water-immiscible droplet within an aqueous droplet that is itself within a water-immiscible host matrix can also be formed. In this example, an emulsion Y is also formed using methods well known in the art.

In some embodiments, the aqueous media may contain fluorescent particles, such that the resulting aqueous droplets of at least one of the two emulsions (emulsions X and Y) contain the fluorescent particles. In some embodiments, the concentration of the fluorescent particles in the aqueous media is set such that statistically there is only one fluorescent particle per aqueous droplet. Subsequent handling of the resulting droplets may then implement fluorescence-based sorting to yield a population of droplets containing a single fluorescent particle.

Fluorescent particles that are quantum dots typically have a semiconductor core surrounded by a protective layer, and are typically about 5 nm diameter. These are suitable for use to label droplets in emulsions of the methods described herein. Other types of fluorescent particles that can be used in the methods herein include fluorescent proteins, fluorescent molecules, and polymeric spheres that contain quantum dots, fluorescent proteins, or fluorescent molecules.

In some embodiments, the aqueous media used to form either emulsion X or emulsion Y (or both) may contain materials other than fluorescent particles, for either labeling the droplet, or as a desired cargo to be included in a merged droplet. For example, the aqueous media may contain protein molecules such as enzymes or receptors, nucleic acid molecules such as DNA or RNA, or small reagent molecules.

In some embodiments, the aqueous media may include or consist of a complex biological sample. For example, the aqueous media may contain samples or components of blood, saliva, or cerebrospinal fluid.

The droplets of each emulsion X and Y may each be separately suspended in a suitable host matrix. The host matrix of each emulsion is a liquid or liquid crystal that is water-immiscible. Examples of host matrices are lipids, hydrocarbon oils, and fluorocarbon oils. A host matrix may be chosen such that it forms a gel or glass at low temperatures, to enhance storage stability over long time periods.

In some embodiments, the density of the droplets relative to its host matrix imposes gravitationally-driven movement of the droplets, either floating upwards or sinking downwards. This movement tends to compact the droplets together, which lessens emulsion stability. This gravitationally-driven movement is mitigated by Brownian motion, such that emulsion stability is improved.

Either or both of emulsion X and emulsion Y may be stabilized with one or more surfactants. In some embodiments, no surfactant is used.

A surfactant is an amphiphilic molecule containing a polar, hydrophilic group and a nonpolar, hydrophobic group. The polar, hydrophilic group can be either positively charged by a cation moiety, negatively charged by an anion moiety, nonionic, or amphoteric. Examples of cationic surfactants are benzalkonium chloride, benzethonium chloride, cetrimonium bromide, stearalkonium chloride, tetramethylammonium hydroxide, and thonzonium bromide. Examples of anionic surfactants are sodium alkyl sulfates, alkylbenzene sulfonates, chlorosulfolipids, perfluoroalkyl sulfonic acids, phospholipids, and sulfolipids. Examples of nonionic surfactants are alkyl polyglycosides, alkyl glucosides, cetyl alcohol, glycerol monostearate, maltosides, nonoxynols, polysorbates, and sorbitan stearates. Examples of amphoteric surfactants are imino propionates, imino acetates, lauryl betaine, betaine citrate, sodium hydroxymethylglycinate, sodium lauroamphoacetate, and (carboxymethyl)dimethyloleylammonium hydroxide. Amphoteric surfactants are also known as zwitterionic surfactants.

In some embodiments, without being bound to any particular theory, each emulsion is stabilized by having a charged surfactant, because their droplets have a like surface charge that repels other droplets, minimizing coalescence of the droplets. The surfactants self-assemble onto the surface of each droplet such that the polar, hydrophilic group of the surfactant molecule is toward the aqueous interior of the droplet, and the nonpolar, hydrophobic group of the surfactant molecule is away from the droplet.

In some embodiments, the sample droplet surfaces or the reagent droplet surfaces are populated with proteins that can occur as membrane proteins in cells. Such proteins have a hydrophobic component that extends into the phospholipid bilayer of cell membranes. Herein, such proteins are considered to be surfactants.

The emulsion X and emulsion Y may be flowed as separate streams into an electrochemical cell. An electrochemical cell drives a redox reaction through the application of an electric potential across a cathode and anode. Optionally, a reference electrode may be used for precise control of the electric potential. A redox reaction is a chemical reaction in which the oxidation states of atomic or molecular species is changed by electron transfer.

The emulsion X is electrochemically charged at the anode of an electrochemical cell, as shown in FIG. 1. A droplet (2) is electrochemically charged by contacting it with an anode (1) at an electric potential sufficient to cause charge transfer (4) between the anode (1) and the droplet (3), and thereby cause an oxidation reaction to occur within the droplet (3) to produce a positively-charged droplet (5). An example of an oxidation reaction is ferrous (2+) ion to ferric (3+) ion plus one electron transferred to the anode, resulting in an electrochemically charged droplet. If the water-immiscible host matrix contains an electrolyte, then the positive charge transferred into the droplet is balanced by opposing anionic charges of the electrolyte associated with the outer surface of the droplet. Examples of such electrolytes are tetrabutylammonium hexafluorophosphate and tetrabutylammonium tetrafluoroborate.

In some embodiments, care is exercised in the selection of electrolyte, because an electrolyte may reduce the zeta-potential of the droplet surfaces and lead to uncontrolled demulsification. In some embodiments, the electrolytes are selected to reduce, minimize, or eliminate the reduction in zeta-potential of the droplet surfaces caused by electrolyte, since the reduction in zeta-potential may lead to uncontrolled demulsification.

The surfactant may be selected to have double or triple bonds along the length of the hydrophobic portion of the molecule, to assist with charge transfer.

The emulsion Y may be electrochemically charged at the cathode of said electrochemical cell. Droplets are electrochemically charged by contacting them with a cathode at an electric potential sufficient to cause charge transfer between the cathode and the droplet, and thereby cause a reduction reaction to occur within the droplet giving it a net negative charge. If the water-immiscible host matrix contains an electrolyte, then the negative charge transferred into the droplet is balanced by opposing cationic charges of the electrolyte on the outer surface of the droplet.

Oxidation or reduction may occur with molecular, atomic, or ionic species that are present within a droplet.

Oxidation or reduction may occur with particular molecular, atomic, or ionic species that are specifically incorporated into the droplets during generation, where such species have favorable oxidation or reduction potentials. In some implementations of the method, at least one suitable charge-carrying molecular species is included in the aqueous mixture when an emulsion for use with the methods herein is formed.

Figure 11:
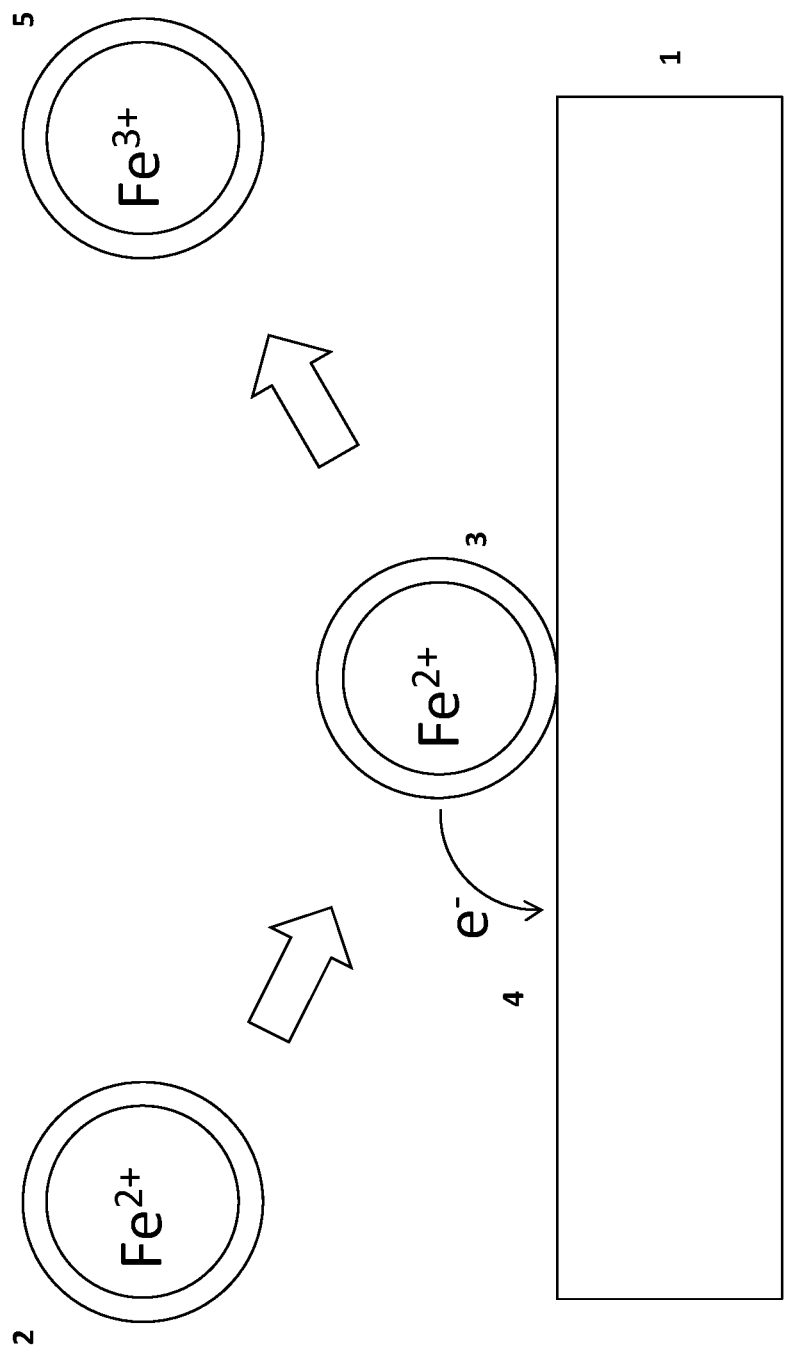
FIG. 11 is a schematic of an electrode performing charge transfer with a water-immiscible droplet within an aqueous droplet that is within a water-immiscible host matrix, according to certain embodiments of the present disclosures.

Oxidation or reduction may occur with molecular, atomic, or ionic species that are within the inner water-immiscible droplet of a secondary emulsion, as shown in FIG. 11.

Figure 2:
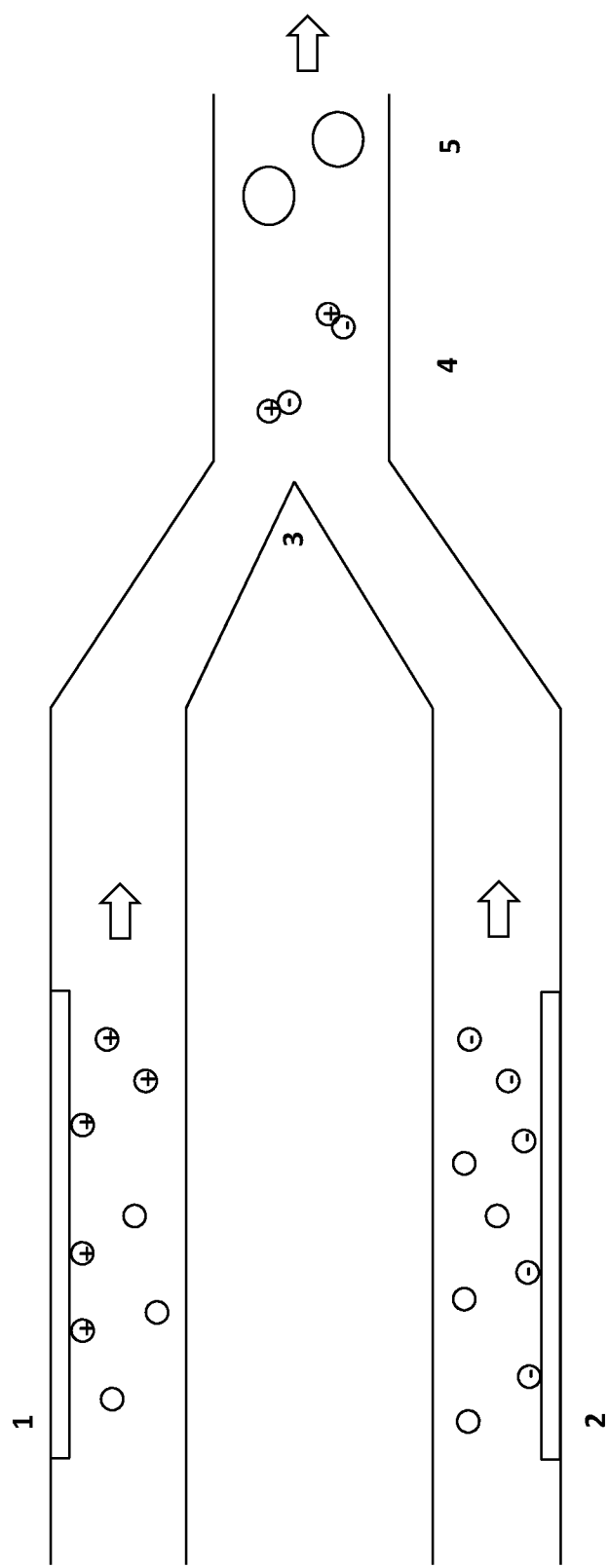
FIG. 2 is a schematic of a pair of electrodes in an electrochemical cell performing oxidation and reduction respectively with an aqueous droplet within a water-immiscible host matrix, according to certain embodiments of the present disclosures.

The emulsion X and emulsion Y can be electrochemically charged within the same electrochemical cell, as shown in FIG. 2. An anode (1) and a cathode (2) are housed in separate channels. Separation between the electrodes ensures that the two emulsions are not mixed prematurely. The two channels are then combined at a junction (3), where the droplets touch (4) and then merge (5). The balance of electrolyte charge passes through the junction (3).

In some embodiments, care is taken to minimize electric field gradients within the electrochemical cell, which can cause uncontrolled demulsification. In some embodiments, the electric field gradients within the electrochemical cell are selected to reduce, minimize, or eliminate the electric field gradients which may lead to uncontrolled demulsification.

Figure 3:
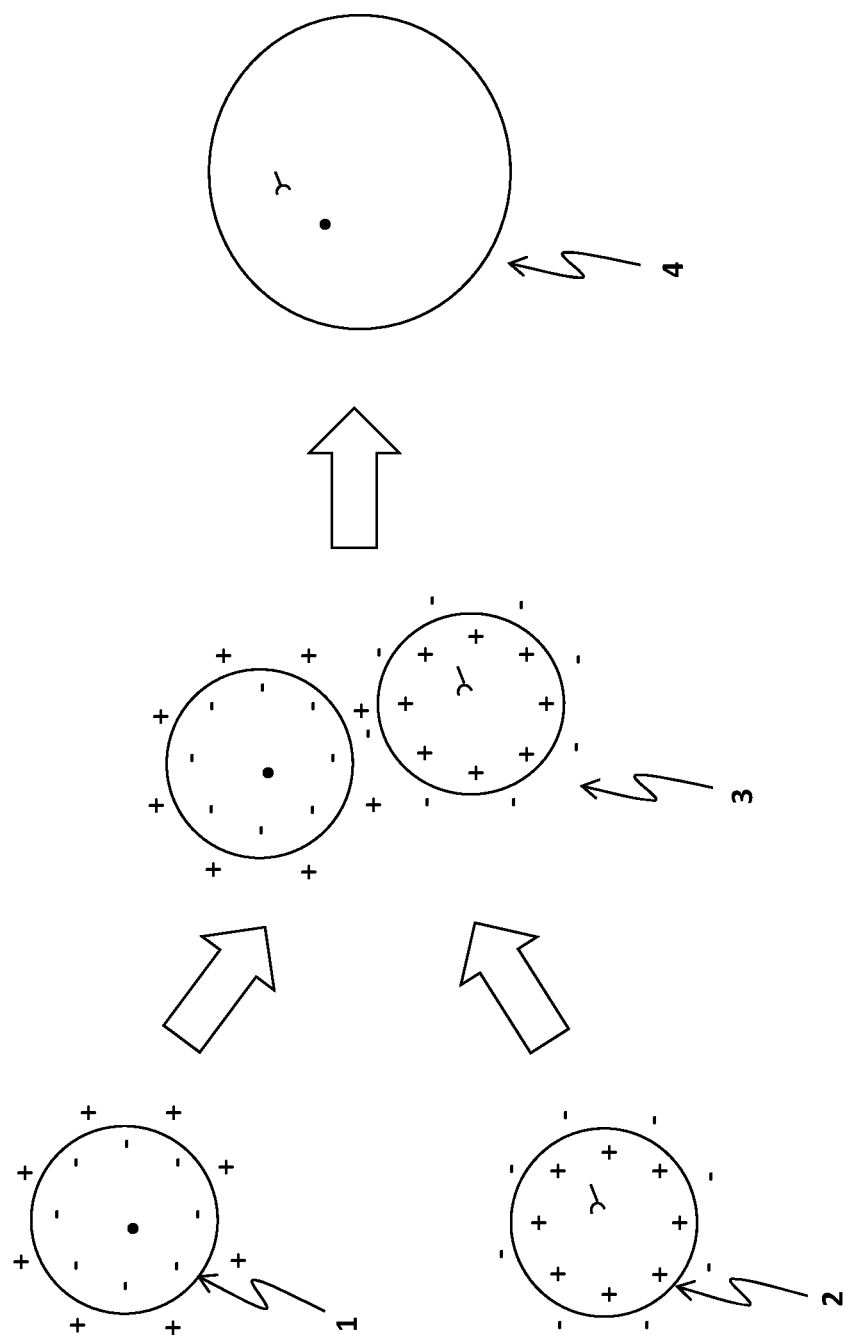
FIG. 3 is schematic of merging droplets having opposite electrochemical charges, according to certain embodiments of the present disclosures.

In some embodiments, after electrochemical charging, the two emulsions are mixed together in an analytic chamber, for instance as shown in FIG. 3. Opposing surface charges may cause attraction between droplets (1) from the anode and droplets (2) from the cathode. This leads to contact of the two droplets (3). In some embodiments, the attraction due to the electrochemical charge differential is greater than the repulsion due to like-charged surfactants, if present. The two droplets then merge together to form a merged droplet (4) of summed mass, which mixes the contents of the two droplets, one from Emulsion X and one from Emulsion Y. This is referred to as a binary merge event. By selecting suitable conditions for emulsion formation and electrochemical charging of the droplets, the droplet size and droplet charge in the two emulsions to be combined can be controlled so that binary merge events produce merged droplets where the electrochemical charges imparted to the individual droplets are balanced, so the merged droplet does not tend to attract other droplets.

In some embodiments, mixing of the pair of electrochemically-charged is implemented by a pair of streams that are continuously flowed into an analytic chamber. In some embodiments, the pair of electrochemically-charged emulsions is mixed together by diffusion or by turbulence. Turbulence may be added by the use of static obstacles to the flow, or by the use of moving components. In some embodiments, the static obstacle is a stationary object in the path of a stream that causes the flow of the stream to become turbulent. In some embodiments, the moving component is a moving object in the path of a stream that causes the flow of the stream to become turbulent, such as a propeller. The pair of streams may be adjacent, transverse, perpendicular, oblique, opposed, or concentric.

In some embodiments, the mixing of the pair of electrochemically-charged emulsions is implemented by a pair of streams that are flowed into an analytic chamber carrying plugs of the emulsions; the flows are stopped when the plugs are delivered to the analytic chamber. In some embodiments, the pair of electrochemically-charged emulsions is mixed together by diffusion or by turbulence. Turbulence may be added by the use of static obstacles to the flow, or by the use of moving components. In some embodiments, the pair of streams may be adjacent, transverse, perpendicular, oblique, opposed, or concentric.

In some embodiments, the mixing of the pair of electrochemically-charged emulsions may be implemented by injecting a stream of one emulsion into an analytic chamber that contains the other emulsion. In some embodiments, the pair of disparate emulsions is mixed together by diffusion or by turbulence. Turbulence may be added by the use of static obstacles to the flow, or by the use of moving components.

In some embodiments, the mixing of the pair of electrochemically-charged emulsions is implemented by repeatedly compressing and expanding the thickness of the analytic chamber.

In some embodiments, after the binary merge event, the electrochemical charges neutralize each other, such that the net charge on the resulting droplet is neutral. In some embodiments, the resulting neutrally-charged droplet does not attract either positively charged or negatively charged droplets, and thus there is no further merging with other droplets. In some embodiments, the result of mixing of the two emulsions is thus largely constrained to binary merge events between droplets of opposite electrochemical charge.

B. Emulsion Comprising Surfactant

In some aspects, provided herein is a method in which a first emulsion is contacted with a stream of anionic surfactant, and a second emulsion is separately contacted with a stream of cationic surfactant. In some embodiments, the method comprises a step of generating or providing the first emulsion. In some embodiments, the method comprises a step of generating or providing the second emulsion.

In some embodiments, the surfactants attach to the surfaces of the droplets, and the droplets thereby become electrically charged. In some embodiments, the two emulsions are then mixed together. Droplets having opposite surfactant charges are attracted to each other and merge.

In some embodiments, the droplets are electrically charged by surfactant molecules rather than electrochemically charged as described in Section I-A, but the features and options of the compositions and methods described in Section I-A may be included in this section. Unlike the use of redox species, the use of surfactant does not require that the aqueous droplets contain species that can be oxidized or reduced, and does not require that the water-immiscible host matrix contain an electrolyte.

For example, an emulsion X is formed using methods known in the art. An example of a method well known in the art is to combine a slow flow of aqueous media with a fast flow of water-immiscible media within a flow cell. This generates aqueous droplets having a highly uniform size within a water-immiscible host matrix. Secondary emulsions that are composed of a water-immiscible droplet within an aqueous droplet that is itself within a water-immiscible host matrix can also be formed. In this example, an emulsion Y is also formed using methods known in the art.

The aqueous media may contain fluorescent particles, such that the resulting aqueous droplets contain the fluorescent particles. In some embodiments, the concentration of the fluorescent particles in the aqueous media is set such that statistically there is only one fluorescent particle per aqueous droplet. Subsequent handling of the resulting droplets may then implement fluorescence-based sorting to yield a population of droplets containing a single fluorescent particle.

Fluorescent particles that are quantum dots typically have a semiconductor core surrounded by a protective layer, and are typically about 5 nm diameter. Other types of fluorescent particles include fluorescent proteins, fluorescent molecules, and polymeric spheres that contain quantum dots, fluorescent proteins, or fluorescent molecules.

The aqueous media may contain particles other than fluorescent particles. For example, the aqueous media may contain protein molecules, nucleic acid molecules such as DNA or RNA, or small reagent molecules.

The aqueous media may contain a complex biological sample. For example, the aqueous media may contain samples of or components of blood, saliva, or cerebrospinal fluid.

The droplets of each emulsion X and Y are suspended in a host matrix. The host matrix of each emulsion is a liquid or liquid crystal that is water-immiscible. Examples of host matrices are lipids, hydrocarbon oils, and fluorocarbon oils. A host matrix may be chosen such that it forms a gel or glass at low temperatures, to enhance storage stability over long time periods.

The density of the droplets relative to its host matrix is thought to impose gravitationally-driven movement of the droplets, either floating upwards or sinking downwards. This movement tends to compact the droplets together, which lessens emulsion stability. This gravitationally-driven movement is mitigated by Brownian motion, such that emulsion stability is improved.

Figure 4:
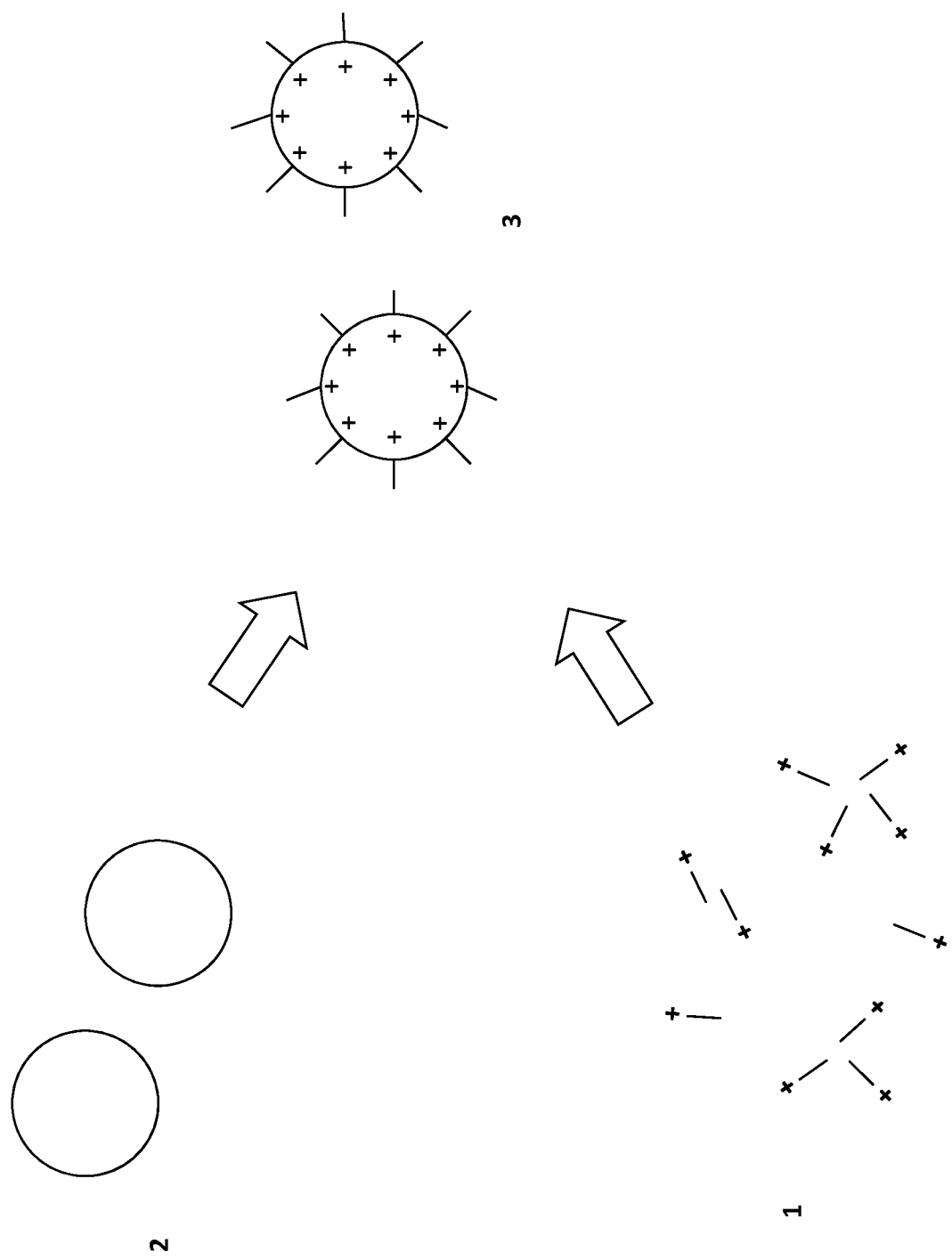
FIG. 4 is a schematic of a droplet interacting with surfactant molecules and micelles, according to certain embodiments of the present disclosures.
Figure 5:
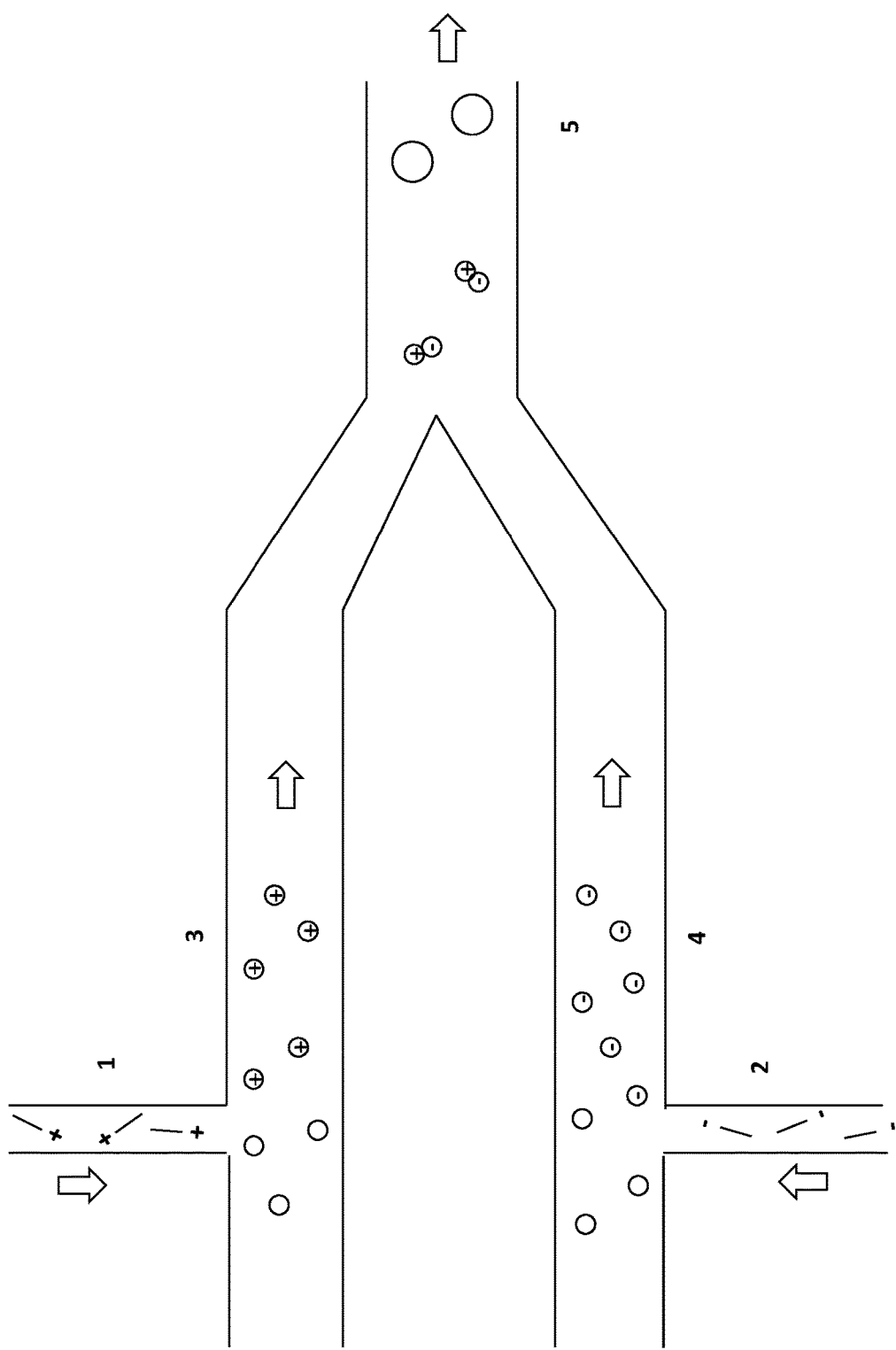
FIG. 5 is a schematic of droplets interacting with cationic surfactants and droplets interacting with cationic surfactants, followed by interaction of the resulting droplets, according to certain embodiments of the present disclosures.

The emulsion X is mixed with a cationic surfactant, sufficient to produce droplets with a positive charge on the inner (aqueous) side of the droplet wall, as shown in FIG. 4. Droplets (2) are mixed with a cationic surfactant stream (1). This produces positive surfactant-charged droplets (3). The emulsion Y is mixed with an anionic surfactant, sufficient to produce droplets with a negative charge on the inner (aqueous) side of the droplet wall. This produces negative surfactant-charged droplets. The emulsion X and emulsion Y are mixed with surfactants in separate channels, as shown in FIG. 5. A cationic surfactant channel (1) and an anionic surfactant channel (2) perform their mixing operations separately, to produce separate populations of positively-charged droplets (3) and negatively-charged droplets (4).

A surfactant is an amphiphilic molecule containing a polar, hydrophilic group and a nonpolar, hydrophobic group. The polar, hydrophilic group can be either positively charged by a cation moiety, negatively charged by an anion moiety, nonionic, or amphoteric. Examples of cationic surfactants are benzalkonium chloride, benzethonium chloride, cetrimonium bromide, stearalkonium chloride, tetramethylammonium hydroxide, and thonzonium bromide. Examples of anionic surfactants are sodium alkyl sulfates, alkylbenzene sulfonates, chlorosulfolipids, perfluoroalkyl sulfonic acids, phospholipids, and sulfolipids.

In some embodiments, without being bound to any particular theory, each emulsion is stabilized by the surfactants because their droplets have a like surface charge that repels other droplets, minimizing coalescence of the droplets. The surfactants self-assemble onto the surface of each droplet such that the polar, hydrophilic group of the surfactant molecule is toward the droplet, and the nonpolar, hydrophobic group of the surfactant molecule is away from the droplet.

In some embodiments, the sample droplet surfaces or the reagent droplet surfaces are populated with proteins that can occur as membrane proteins in cells. Such proteins have a hydrophobic component that extends into the phospholipid bilayer of cell membranes. Herein, such proteins are considered to be surfactants.

In some embodiments, the positive surfactant-charged emulsion X and negative surfactant-charged emulsion Y are flowed as separate streams into an analytic chamber. The separate streams are mixed together in the analytic chamber. In some embodiments, opposing surfactant charges cause attraction between droplets with a cationic surfactant and droplets with an anionic surfactant. This leads to contact of the two droplets. In some embodiments, the two droplets then merge together to form a merged droplet of summed mass, which mixes the contents of the two droplets. This is referred to as a binary merge event.

Figure 6:
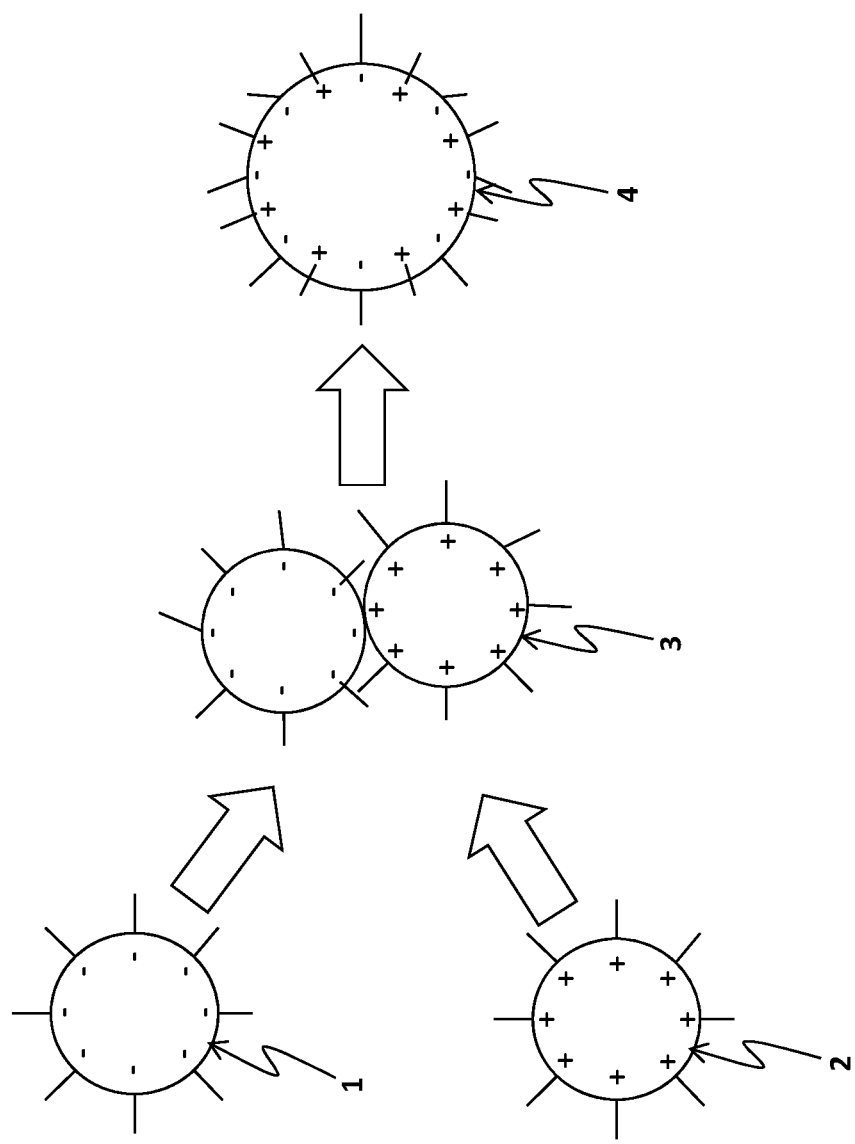
FIG. 6 is a schematic of droplets having oppositely-charged surfactants that interact and merge, according to certain embodiments of the present disclosures.

In some embodiments, mixing of the pair of surfactant-charged emulsions is implemented by a pair of streams that are continuously flowed into an analytic chamber, as shown in FIG. 6. The inputs to the analytic chamber are a stream of positive surfactant-charged droplets (2) and a stream of negative surfactant-charged droplets (1). The pair of surfactant-charged emulsions is mixed together by diffusion or by turbulence. Turbulence may be added by the use of static obstacles to the flow, or by the use of moving components. A static obstacle is a stationary object in the path of a stream that causes the flow of the stream to become turbulent. A moving component is a moving object in the path of a stream that causes the flow of the stream to become turbulent, such as a propeller. The pair of streams may be adjacent, transverse, perpendicular, oblique, opposed, or concentric.

In some embodiments, the mixing of the pair of disparate emulsions is implemented by a pair of streams that are flowed into an analytic chamber carrying plugs of the emulsions; the flows are stopped when the plugs are delivered to the analytic chamber. The pair of surfactant-charged emulsions is mixed together by diffusion or by turbulence. Turbulence may be added by the use of static obstacles to the flow, or by the use of moving components. The pair of streams may be adjacent, transverse, perpendicular, oblique, opposed, or concentric.

In some embodiments, the mixing of the pair of surfactant-charged emulsions is implemented by injecting a stream of one emulsion into an analytic chamber that contains the other emulsion. The pair of disparate emulsions is mixed together by diffusion or by turbulence. Turbulence may be added by the use of static obstacles to the flow, or by the use of moving components.

In some embodiments, the mixing of the pair of disparate emulsions is implemented by repeatedly compressing and expanding the thickness of the analytic chamber.

In some embodiments, after the binary merge event (3), the surfactant charges neutralize each other, such that the net charge on the resulting droplet (4) is neutral. The resulting neutrally-charged droplet does not attract either positively charged or negatively charged droplets, and thus there is no further merging with other droplets. The result of mixing of the two emulsions is thus largely constrained to binary merge events between droplets of opposite surfactant charge.

C. Electrostatically Charged Emulsion

In some aspects, electrostatically charged emulsion droplets are used in a method disclosed herein. In some embodiments, a first emulsion is contacted with an electrode at a high electric potential, and a second emulsion is contacted with an electrode at a high and opposite electric potential. The droplets thereby become electrostatically charged. The two emulsions are then mixed together. Droplets of opposite electrostatic charge are attracted to each other and merge.

In some embodiments, the method comprises a step of generating or providing the first emulsion and/or a step of generating or providing the second emulsion.

In some aspects, the droplets are electrostatically charged by high potential rather than electrochemically charged as described in Section I-A, but the features and options of the compositions and methods described in Section I-A may be included in this section. Unlike the use of electrochemically charged droplets, the use of electrostatically charged droplets does not require that the aqueous droplets contain species that can be oxidized or reduced, and does not require that the water-immiscible host matrix contain an electrolyte.

In some examples, an emulsion X is formed using methods well known in the art. An example of a method well known in the art is to combine a slow flow of aqueous media with a fast flow of water-immiscible media within a flow cell. This generates aqueous droplets having a highly uniform size within a water-immiscible host matrix. Secondary emulsions that are composed of a water-immiscible droplet within an aqueous droplet that is itself within a water-immiscible host matrix can also be formed. In these examples, an emulsion Y is also formed using methods well known in the art.

In some embodiments, the aqueous media may contain fluorescent particles, such that the resulting aqueous droplets contain the fluorescent particles. In some embodiments, the concentration of the fluorescent particles in the aqueous media is set such that statistically there is only one fluorescent particle per aqueous droplet. Subsequent handling of the resulting droplets may then implement fluorescence-based sorting to yield a population of droplets containing a single fluorescent particle.

Fluorescent particles that are quantum dots typically have a semiconductor core surrounded by a protective layer, and are typically about 5 nm diameter. Other types of fluorescent particles include fluorescent proteins, fluorescent molecules, and polymeric spheres that contain quantum dots, fluorescent proteins, or fluorescent molecules.

The aqueous media may contain particles other than fluorescent particles. For example, the aqueous media may contain protein molecules, nucleic acid molecules such as DNA or RNA, or small reagent molecules.

The aqueous media may comprise a complex biological sample. For example, the aqueous media may contain blood, saliva, or cerebrospinal fluid.

In some embodiments, the droplets of each emulsion X and Y are suspended in a host matrix. The host matrix of each emulsion is a liquid or liquid crystal that is water-immiscible. Examples of host matrices are lipids, hydrocarbon oils, and fluorocarbon oils. A host matrix may be chosen such that it forms a gel or glass at low temperatures, to enhance storage stability over long time periods.

In some embodiments, the density of the droplets relative to its host matrix imposes gravitationally-driven movement of the droplets, either floating upwards or sinking downwards. This movement tends to compact the droplets together, which lessens emulsion stability. This gravitationally-driven movement is mitigated by Brownian motion, such that emulsion stability is improved.

The emulsion X and the emulsion Y may be stabilized with one or more surfactants or none at all. A surfactant is an amphiphilic molecule containing a polar, hydrophilic group and a nonpolar, hydrophobic group. The polar, hydrophilic group can be either positively charged by a cation moiety, negatively charged by an anion moiety, nonionic, or amphoteric. Examples of cationic surfactants are benzalkonium chloride, benzethonium chloride, cetrimonium bromide, stearalkonium chloride, tetramethylammonium hydroxide, and thonzonium bromide. Examples of anionic surfactants are sodium alkyl sulfates, alkylbenzene sulfonates, chlorosulfolipids, perfluoroalkyl sulfonic acids, phospholipids, and sulfolipids. Examples of nonionic surfactants are alkyl polyglycosides, alkyl glucosides, cetyl alcohol, glycerol monostearate, maltosides, nonoxynols, polysorbates, and sorbitan stearates. Examples of amphoteric surfactants are imino propionates, imino acetates, lauryl betaine, betaine citrate, sodium hydroxymethylglycinate, sodium lauroamphoacetate, and (carboxymethyl)dimethyloleylammonium hydroxide. Amphoteric surfactants are also known as zwitterionic surfactants.

In some embodiments, without being bound to any particular theory, each emulsion is stabilized by the surfactants because their droplets have a like surface charge that repels other droplets, minimizing coalescence of the droplets. In some embodiments, the surfactants self-assemble onto the surface of each droplet such that the polar, hydrophilic group of the surfactant molecule is toward the droplet, and the nonpolar, hydrophobic group of the surfactant molecule is away from the droplet.

In some embodiments, the sample droplet surfaces or the reagent droplet surfaces are populated with proteins that can occur as membrane proteins in cells. Such proteins have a hydrophobic component that extends into the phospholipid bilayer of cell membranes. Herein, such proteins are considered to be surfactants.

In some embodiments, the emulsion X and emulsion Y are flowed as separate streams into an electrostatic cell. An electrostatic cell drives an electrostatic charge onto the droplets through the application of a high electric potential across a pair of electrodes.

Figure 7:
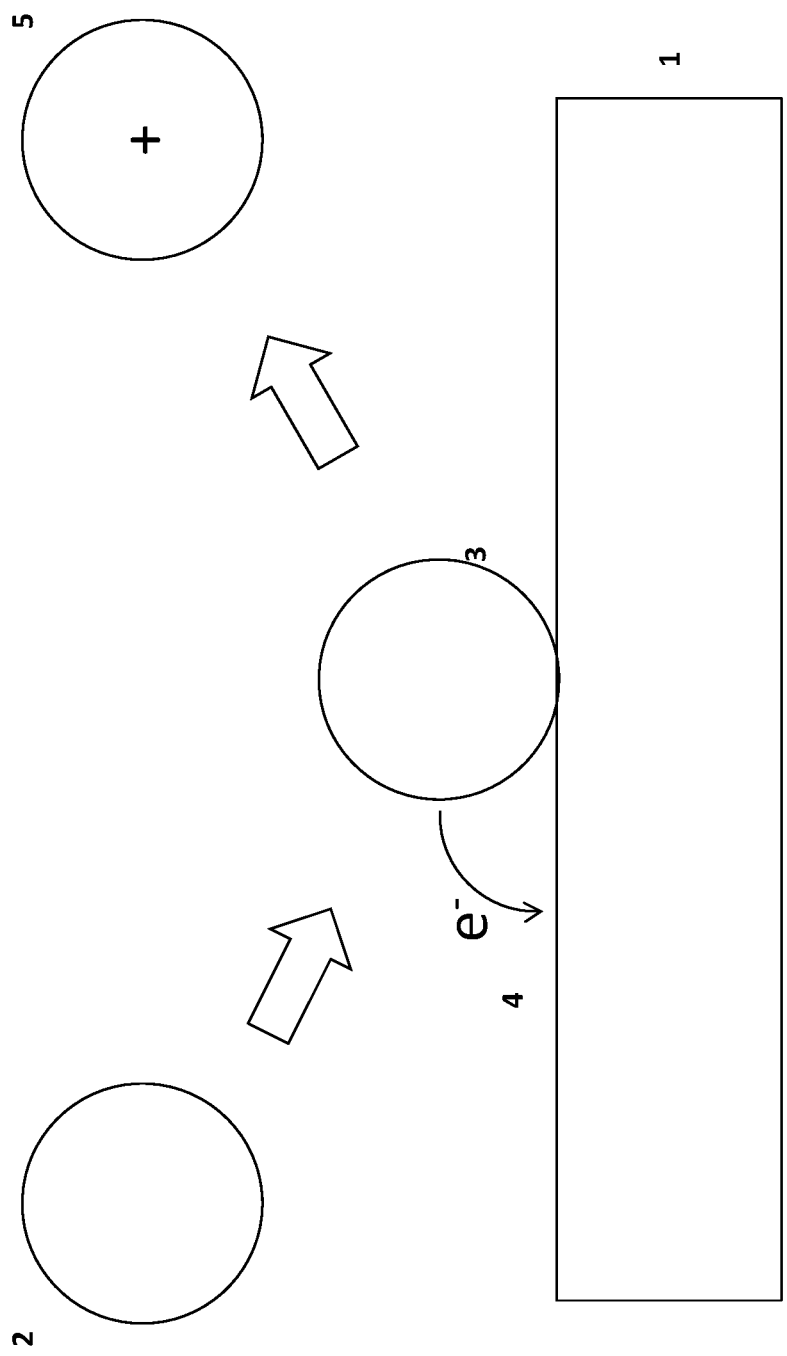
FIG. 7 is a schematic of a droplet contacting an electrode and transferring an electron to the electrode, according to certain embodiments of the present disclosures.

In some embodiments, the emulsion X is electrostatically charged at the positive electrode of an electrostatic cell, as shown in FIG. 7. A droplet (2) is electrostatically charged by passing it to a positive electrode (1) at a high positive electric potential sufficient to cause removal of electrons (4) from the droplet (3) to produce a positively-charged droplet (5).

In some embodiments, the emulsion Y is electrostatically charged at the negative electrode of said electrostatic cell. Droplets are electrostatically charged by passing them to a negative electrode at a high negative potential sufficient to cause addition of electrons to the droplet.

Figure 8:
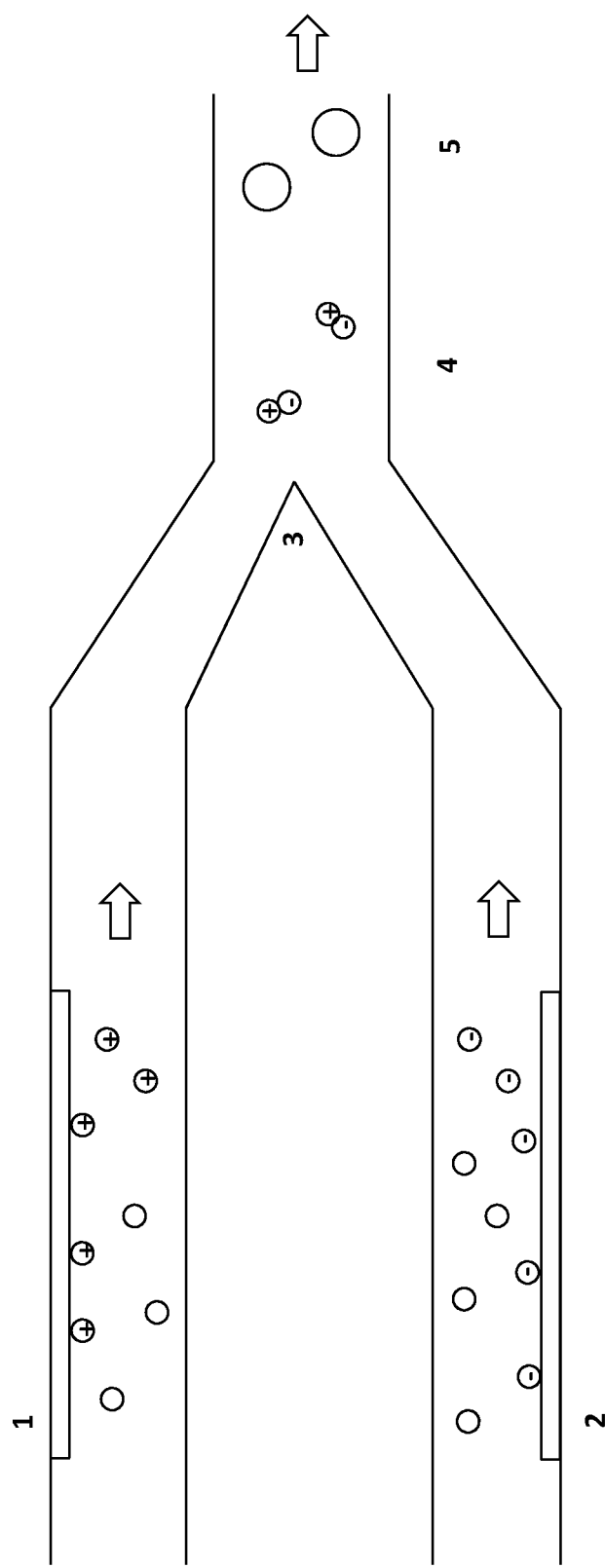
FIG. 8 is a schematic of a pair of high-potential electrodes inducing electrostatic charges on droplets, followed by interaction of the resulting droplets, according to certain embodiments of the present disclosures.

In some embodiments, the emulsion X and emulsion Y are electrostatically charged within the same electrostatic cell, as shown in FIG. 8. A positive electrode (1) and a negative electrode (2) are housed in separate channels. Separation between the electrodes ensures that the two emulsions are not mixed prematurely. The two channels are then combined at a junction (3), where the droplets touch (4) and then merge (5).

In some embodiments, especially when higher electric potentials are used, electric field gradients within the electrochemical cell are reduced, minimized, or eliminated, since electric field gradients may cause uncontrolled demulsification.

Figure 9:
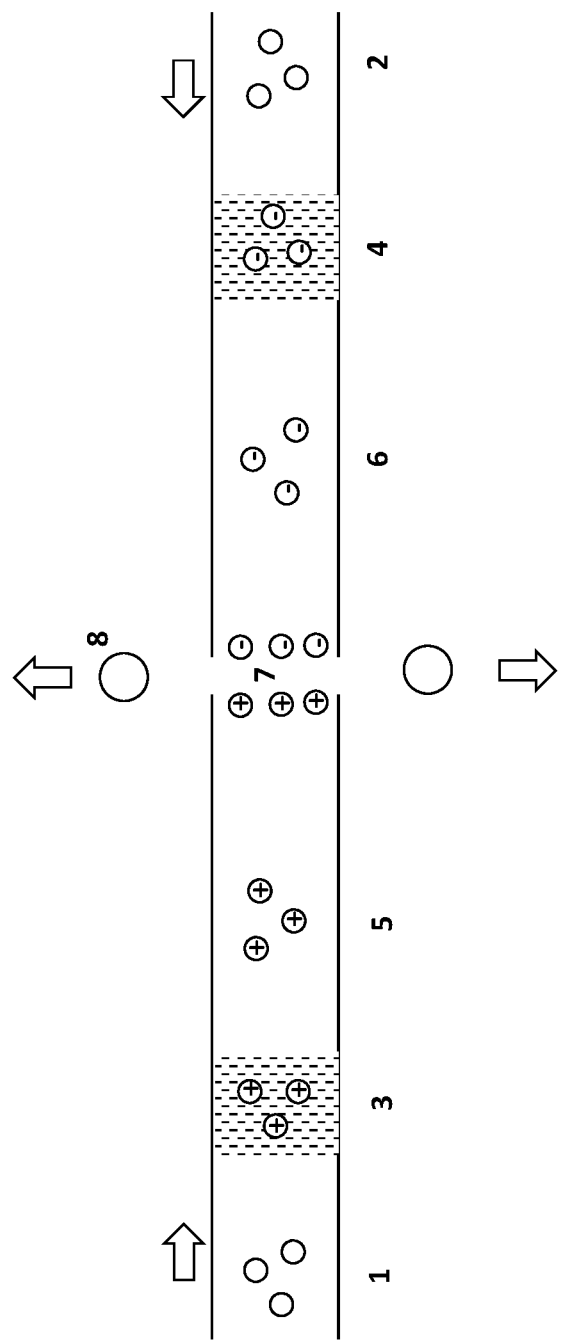
FIG. 9 is a schematic of a pair of streams of oppositely-charged droplets that impinge each other to allow the droplets to merge, according to certain embodiments of the present disclosures.

In some embodiments, electric field gradients are minimized by a design, for example, as shown in FIG. 9. A plug of emulsion droplets (1 and 2) is swept by a carrier stream of water-immiscible host matrix through an electrically conductive frit (3 and 4), which electrostatically charges the droplets by brief contact at high electric potential. The high electric potential is applied once the plug of droplets is contained within the frit. The carrier stream continues to sweep the droplets (5 and 6) into an electrically conductive cylinder that is held at the same electric potential as the frit. This ensures that there is minimal electric field gradient during electrostatic charging of the droplets, and after the droplets leave the frit.

In some embodiments, the exit of the electrically conductive cylinder is positioned very close to the exit of a second electrically conductive cylinder that generates droplets of opposite electrostatic charge. In some embodiments, the narrow interface between the cylinders has a strong electric field gradient, but it is constrained to a narrow plane that is much thinner than the width of the droplet plugs. In some embodiments, with a dilute emulsion, droplets preferentially align with a droplet of opposite charge prior to exposure to the strong electric field gradient.

In some embodiments, the two opposing carrier stream flows combine positively-charged droplets and negatively-charged droplets, allowing oppositely-charged droplets to merge in binary merge events (7). In some embodiments, the strong electric field gradient induces dipole charges across each droplet, but it is in the same direction that the droplets are preferentially aligned and travelling towards each other. Uncontrolled demulsification by dipole-dipole attractions produced by the strong electric field gradient is thereby minimized.

In some embodiments, the resulting merged droplets (8) are mostly constrained to the two-dimensional plane of the stream interface, where the electric field gradient would induce dipole charges across each merged droplet (8) in a direction that is perpendicular to that plane. The concentration of particles in that perpendicular direction is much lower than along the plane, reducing the probability of dipole-dipole attractions in the perpendicular direction. Uncontrolled demulsification by dipole-dipole attractions produced by the strong electric field gradient is thereby minimized.

In some embodiments, the merged droplets (8) are then be transported radially outward by the combined carrier streams, where they are collected.

In some embodiments, the first and second electrically-conductive cylinders are widely spaced, to reduce the magnitude of the electric field gradient between them, and thus reduce the magnitude of dipole-dipole attractions that could lead to uncontrolled demulsification.

In some embodiments, the surfactant is selected to have double or triple bonds along the length of the hydrophobic portion of the molecule, to assist with charge transfer.

Figure 10:
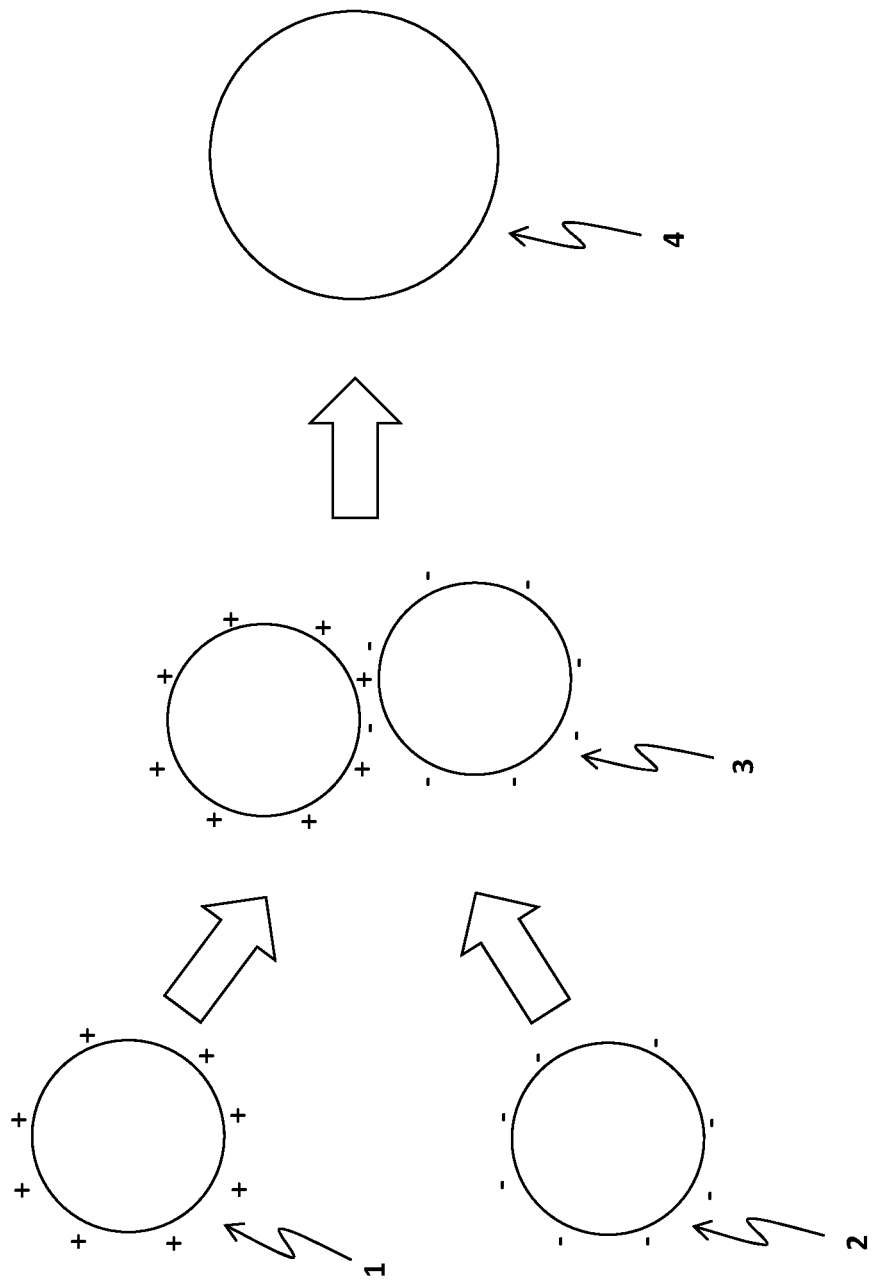
FIG. 10 is a schematic of the merging of two droplets of opposite electrostatic charge, according to certain embodiments of the present disclosures.

In some embodiments, after electrostatic charging, the two emulsions are mixed together in an analytic chamber, as shown in FIG. 10. Opposing electrostatic charges cause attraction between droplets (1) from the positive electrode and droplets (2) from the negative electrode. This leads to contact of the two droplets (3). The two droplets then merge together to form a merged droplet (4) of summed mass, which mixes the contents of the two droplets. This is referred to as a binary merge event. The attraction due to the electrostatic charge differential should be greater than the repulsion due to like-charged surfactants, if present.

In some embodiments, mixing of the pair of electrostatically-charged emulsions is implemented by a pair of streams that are continuously flowed into an analytic chamber. The pair of electrostatically-charged emulsions is mixed together by diffusion or by turbulence. Turbulence may be added by the use of static obstacles to the flow, or by the use of moving components. A static obstacle is a stationary object in the path of a stream that causes the flow of the stream to become turbulent. A moving component is a moving object in the path of a stream that causes the flow of the stream to become turbulent, such as a propeller. The pair of streams may be adjacent, transverse, perpendicular, oblique, opposed, or concentric.

In some embodiments, mixing of the pair of disparate emulsions is implemented by a pair of streams that are flowed into an analytic chamber carrying plugs of the emulsions. In some embodiments, the flows are stopped when the plugs are delivered to the analytic chamber. In some embodiments, the pair of electrostatically-charged emulsions is mixed together by diffusion or by turbulence. Turbulence may be added by the use of static obstacles to the flow, or by the use of moving components. The pair of streams may be adjacent, transverse, perpendicular, oblique, opposed, or concentric.

In some embodiments, mixing of the pair of electrostatically-charged emulsions is implemented by injecting a stream of one emulsion into an analytic chamber that contains the other emulsion. The pair of disparate emulsions is mixed together by diffusion or by turbulence. Turbulence may be added by the use of static obstacles to the flow, or by the use of moving components.

In some embodiments, mixing of the pair of electrostatically-charged emulsions is implemented by repeatedly compressing and expanding the thickness of the analytic chamber.

In some embodiments, after the binary merge event, the electrostatic charges neutralize each other, such that the net charge on the resulting droplet is neutral. The resulting neutrally-charged droplet does not attract either positively charged or negatively charged droplets, and thus there is no further merging with other droplets. The result of mixing of the two emulsions is thus largely constrained to binary merge events between droplets of opposite electrostatic charge.

D. Emulsion Comprising Magnetic Particles

In some embodiments, a method disclosed herein comprises using a first emulsion comprising aqueous droplets that contain a first magnetic particle with a positive electric charge in a first water-immiscible host matrix. In some embodiments, the method comprises a step of generating or providing the first emulsion.

In some embodiments, a method disclosed herein comprises using a second emulsion comprising aqueous droplets that contain a second magnetic particle with a negative electric charge in a second water-immiscible host matrix, is generated. In some embodiments, the method comprises a step of generating or providing the second emulsion.

In some embodiments, a method disclosed herein comprises using a first emulsion comprising aqueous droplets that contain a first magnetic particle with a first electric charge in a first water-immiscible host matrix, and using a second emulsion comprising aqueous droplets that contain a second magnetic particle with a second electric charge in a second water-immiscible host matrix, where the first and second electric charges are opposite charges, e.g., charges that can neutralize each other. In some embodiments, the method comprises a step of generating or providing the first emulsion and/or the second emulsion.

The electric charges on the magnetic particles may be imposed by the usage of bound charged moieties on the surface of each magnetic particle, or may be imposed by charge transfer from electrochemical electrodes as described in the above First Example. Droplets within both emulsions thus contain magnetic particles that are electrically charged with opposite charges. The two emulsions are then mixed together. After mixing of the first and second droplets, opposite electrically charged magnetic particles may exhibit a degree of attraction to each other. This degree of attraction may cause the Brownian motion of the magnetic particles to be statistically closer to each other, rather than randomly distributed across the droplets. The degree of attraction may be enhanced by the application of a weak magnetic field that is strong enough to cause the magnetic particles to tend to position themselves nearer each other, but not so strong that the magnetic particles overcome Brownian motion entirely and stick together. The subsequent application of a strong magnetic field then causes the magnetic particles to stick together, thereby breaking the interfacial barrier between the two droplets, resulting in a binary merge event. In some embodiments, such a merge event would only occur between droplets of the first emulsion and droplets of the second emulsion, even if all the droplets are in close proximity, such as during flocculation.

In some embodiments, an emulsion X is formed using methods known in the art. An example of a method well known in the art is to combine a slow flow of aqueous media with a fast flow of water-immiscible media within a flow cell. This generates aqueous droplets having a highly uniform size within a water-immiscible host matrix. Secondary emulsions that are composed of a water-immiscible droplet within an aqueous droplet that is itself within a water-immiscible host matrix can also be formed.

In some embodiments, an emulsion Y is also formed using methods well known in the art.

The aqueous media may contain magnetic particles, such that the resulting aqueous droplets contain the magnetic particles. The concentration of the magnetic particles in the aqueous media may be set such that statistically there is only one magnetic particle per aqueous droplet. Subsequent handling of the resulting droplets may then implement magnetic-based sorting to yield a population of droplets containing a single magnetic particle.

Magnetic particles typically have a magnetically permeable core surrounded by a protective layer, and are typically about 5 nm diameter. Examples of magnetic particles are maghemite, magnetite, iron metal, or cobalt metal. These may be coated with silica, surfactants, silicones, or phosphoric acid derivatives. With a size below about 128 nm, such particles become superparamagnetic, and thus do not retain a static magnetic field that would cause self-agglomeration. Application of an external magnetic field temporarily magnetizes the magnetic particles while the external magnetic field is applied. While magnetized, the magnetic particles may experience an attractive force between them that is proportional to the strength of the external magnetic field.

The aqueous media used to form either emulsion X or emulsion Y (or both) may contain materials other than magnetic particles, for either labeling the droplet, or as a desired cargo to be included in a merged droplet. For example, the aqueous media may contain fluorescent particles, protein molecules such as enzymes or receptors, nucleic acid molecules such as DNA or RNA, or small reagent molecules.

The aqueous media may include or consist of a complex biological sample. For example, the aqueous media may contain samples or components of blood, saliva, or cerebrospinal fluid.

The droplets of each emulsion X and Y are each separately suspended in a suitable host matrix. The host matrix of each emulsion is a liquid or liquid crystal that is water-immiscible. Examples of host matrices are lipids, hydrocarbon oils, and fluorocarbon oils. A host matrix may be chosen such that it forms a gel or glass at low temperatures, to enhance storage stability over long time periods.

The density of the droplets relative to its host matrix is thought to impose gravitationally-driven movement of the droplets, either floating upwards or sinking downwards. This movement tends to compact the droplets together, which lessens emulsion stability. This gravitationally-driven movement is mitigated by Brownian motion, such that emulsion stability is improved.

Either or both of emulsion X and emulsion Y may be stabilized with one or more surfactants, or no surfactant may be used.

A surfactant is an amphiphilic molecule containing a polar, hydrophilic group and a nonpolar, hydrophobic group. The polar, hydrophilic group can be either positively charged by a cation moiety, negatively charged by an anion moiety, nonionic, or amphoteric. Examples of cationic surfactants are benzalkonium chloride, benzethonium chloride, cetrimonium bromide, stearalkonium chloride, tetramethylammonium hydroxide, and thonzonium bromide. Examples of anionic surfactants are sodium alkyl sulfates, alkylbenzene sulfonates, chlorosulfolipids, perfluoroalkyl sulfonic acids, phospholipids, and sulfolipids. Examples of nonionic surfactants are alkyl polyglycosides, alkyl glucosides, cetyl alcohol, glycerol monostearate, maltosides, nonoxynols, polysorbates, and sorbitan stearates. Examples of amphoteric surfactants are imino propionates, imino acetates, lauryl betaine, betaine citrate, sodium hydroxymethylglycinate, sodium lauroamphoacetate, and (carboxymethyl)dimethyloleylammonium hydroxide. Amphoteric surfactants are also known as zwitterionic surfactants.

In some embodiments, without being bound to any particular theory, each emulsion is stabilized by having a charged surfactant, because their droplets have a like surface charge that repels other droplets, minimizing coalescence of the droplets. The surfactants self-assemble onto the surface of each droplet such that the polar, hydrophilic group of the surfactant molecule is toward the aqueous interior of the droplet, and the nonpolar, hydrophobic group of the surfactant molecule is away from the droplet.

In some embodiments, the sample droplet surfaces or the reagent droplet surfaces are populated with proteins that can occur as membrane proteins in cells. Such proteins have a hydrophobic component that extends into the phospholipid bilayer of cell membranes. Herein, such proteins are considered to be surfactants.

Figure 12:
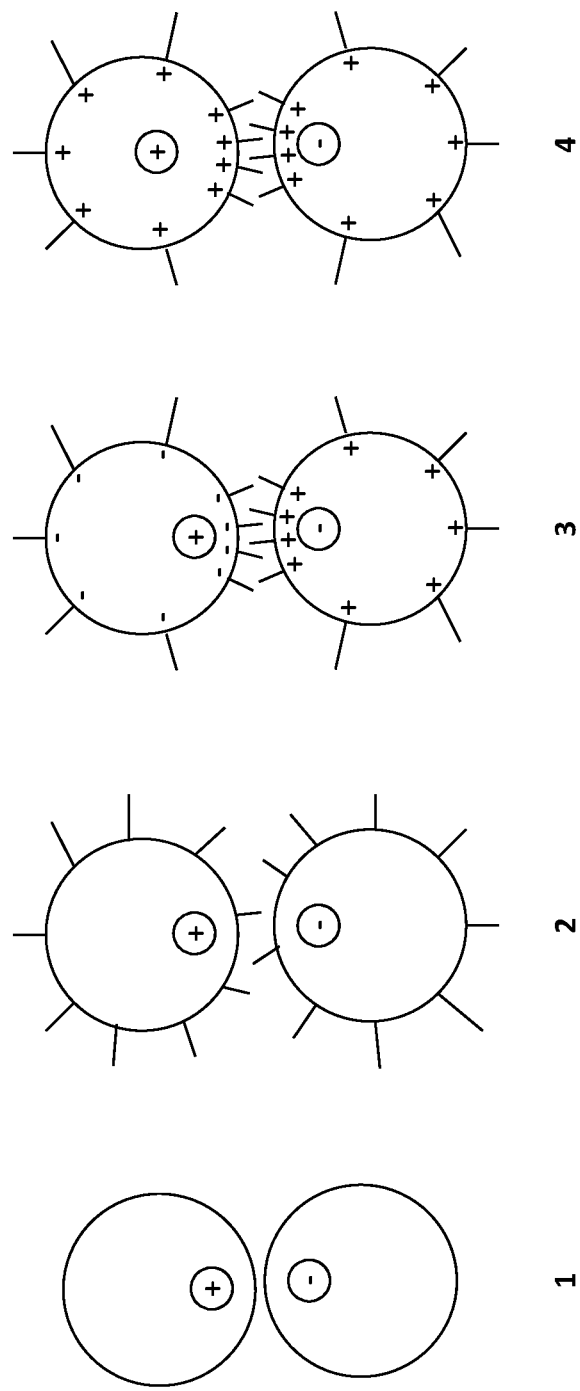
FIG. 12 is a schematic of droplets containing electrically-charged magnetic particles within aqueous droplets that are each within a water-immiscible host matrix, according to certain embodiments of the present disclosures.

In some embodiments, the two disparate emulsions are mixed together in an analytic chamber, as shown in FIG. 12. Opposing electric charges on the magnetic particles may cause a degree of attraction between droplets from emulsion X and droplets from emulsion Y. This may lead to contact of the two droplets (1). Droplets may also be contacted by floating or sinking within the analytic chamber (which compresses them together), or flocculation. This degree of attraction may also cause the Brownian motion of the magnetic particles to be statistically closer to each other, rather than randomly distributed across the droplets. The degree of attraction may be enhanced by the application of a weak magnetic field that is strong enough to cause the magnetic particles to tend to position themselves nearer each other, but not so strong that the magnetic particles overcome Brownian motion entirely and stick together. The subsequent application of a strong magnetic field then causes the magnetic particles to stick together, thereby breaking the interfacial barrier between the two droplets, resulting in a binary merge event. Such a merge event would only occur between droplets of emulsion X and droplets of emulsion Y, even if all the droplets are in close proximity, such as during flocculation.

In some embodiments, the presence of one or more surfactants influences the positioning of the magnetic particles and their mutual attraction. In some embodiments, the surfactants are nonionic or amphoteric (2), and there is only minimal effect on the positioning and mutual attraction. In some embodiments, the surfactants are anionic and cationic (3), both cationic (4), or both anionic, and an electrically charged magnetic particle can be attracted to or repelled from the inner wall of its droplet. This may partially shield the electric charge of that magnetic particle from an oppositely-charged magnetic particle in an adjacent droplet. A degree of shielding may also be induced by the presence of electrolytes that may form an electrical double-layer around the electrically charged magnetic particle.

In some embodiments, mixing of the pair of disparate emulsions is implemented by a pair of streams that are continuously flowed into an analytic chamber. The pair of emulsions is mixed together by diffusion or by turbulence. Turbulence may be added by the use of static obstacles to the flow, or by the use of moving components. A static obstacle is a stationary object in the path of a stream that causes the flow of the stream to become turbulent. A moving component is a moving object in the path of a stream that causes the flow of the stream to become turbulent, such as a propeller. The pair of streams may be adjacent, transverse, perpendicular, oblique, opposed, or concentric.

In some embodiments, mixing of the pair of disparate emulsions is implemented by a pair of streams that are flowed into an analytic chamber carrying plugs of the emulsions. In some embodiments, the flows are stopped when the plugs are delivered to the analytic chamber. The pair of emulsions is mixed together by diffusion or by turbulence. Turbulence may be added by the use of static obstacles to the flow, or by the use of moving components. The pair of streams may be adjacent, transverse, perpendicular, oblique, opposed, or concentric.

In some embodiments, mixing of the pair of disparate emulsions is implemented by injecting a stream of one emulsion into an analytic chamber that contains the other emulsion. The pair of disparate emulsions is mixed together by diffusion or by turbulence. Turbulence may be added by the use of static obstacles to the flow, or by the use of moving components.

In some embodiments, mixing of the pair of disparate emulsions is implemented by repeatedly compressing and expanding the thickness of the analytic chamber.

In any of the preceding embodiments, the method disclosed herein may comprise the use of aqueous emulsions to contain the sample and transport it to measurement apparatus, for example, as described in WO2002/068104, U.S. Pat. Nos. 7,268,167, 7,772,287, 7,717,615, 7,375,140, WO2005/089921, and U.S. Pat. No. 8,741,192 of the Japan Science and Technology Agency, the disclosures of all of which are incorporated herein by reference.

In any of the preceding embodiments, the method disclosed herein may comprise the use of electrochemistry with emulsions, for example, as described by H. Zhang, L. Sepunaru, S. Sokolov, et al. in "Electrochemistry of single droplets of inverse (water-in-oil) emulsions", Phys. Chem. Chem. Phys. 2017, 19, 15662-15666, the disclosure of which is incorporated herein by reference. In some embodiments, a method disclosed herein comprises the use of an electrode to perform a charge transfer between the electrode surface and redox species within a droplet.

In some embodiments, a method disclosed herein covers the controlled merging of emulsion droplets. In certain aspects, these methods are useful for the preparation of emulsion libraries that contain addressed compositions. A vial of such an emulsion library might contain droplets where each droplet contains a different antibody and a unique combination of quantum dots in free suspension. Subsequently charging this emulsion (electrochemically, with surfactants, or electrostatically) as described herein and then mixing it with an oppositely charged sample emulsion containing antigens would perform a massively parallel set of reactions.

The use of emulsions instead of fixed array plates allows the formation of arrays of arbitrary size, allows the sample volume to be small, and avoids having the sample contact plumbing surfaces that can adsorb analytes.

The addition of new and more powerful tools, such as the methods described herein, to the repertoire of medical researchers would deepen the understanding of protein systems and allow the development of new diagnostics and new drug therapies.

II. COMPOSITIONS AND METHODS FOR ANALYZING AN ANALYTE

In some embodiments, disclosed herein is a method, e.g., for detecting the presence/absence, a level or amount, and/or an activity of an analyte in a sample, which method comprises (a) providing a first emulsion that comprises a first aqueous droplet in a first liquid matrix, wherein the first aqueous droplet comprises a portion of the sample; (b) providing a second emulsion that comprises a second aqueous droplet in a second liquid matrix, wherein the second aqueous droplet comprises an analyte interacting reagent (e.g., analyte binding reagent); (c) contacting the first emulsion with the second emulsion to form a combined emulsion under conditions that allow the first aqueous droplet to merge with the second aqueous droplet to form a merged droplet; and (d) detecting a signal generated by a binding interaction of the analyte with the analyte interacting reagent (e.g., analyte binding reagent).

In some aspects, provided herein is a method for detection of an analyte in a sample, where the analyte is introduced into a droplet of a first emulsion, which is stabilized by a surfactant, typically an ionic surfactant. The first emulsion is then mixed with a second emulsion containing aqueous droplets that comprise an analyte binding reagent, and are optionally also stabilized by a surfactant that may be an ionic surfactant having the opposite charge from the surfactant in the sample-containing emulsion. The droplets of the first or second emulsion can contain a detectable species such as a magnetic particle or fluorescent particle or label. When the first and second emulsions are combined, permitting the droplets containing the analyte and the analyte binding reagent to combine, the binding of analyte to analyte binding reagent produces a detectable signal that is detected to determine the presence and/or amount of analyte present in the sample.

In some embodiments, disclosed herein is a method, e.g., for detecting the presence/absence, a level or amount, and/or an activity of an analyte in a sample, which method comprises: contacting a first emulsion with a second emulsion, wherein the first emulsion comprises a first aqueous droplet in a first liquid matrix and the second emulsion comprises a second aqueous droplet in a second liquid matrix. In some embodiments, the first aqueous droplet comprises an analyte, wherein the analyte is optionally derived from a biological sample. In some embodiments, the second aqueous droplet comprises an analyte interacting reagent (e.g., analyte binding reagent). In some embodiments, the contacting is under conditions that allow the first aqueous droplet to merge with the second aqueous droplet to form a merged droplet. In some embodiments, the method further comprises detecting a signal generated by a binding interaction of the analyte with the analyte interacting reagent (e.g., analyte binding reagent).

In some embodiments, the analyte interacting reagent (e.g., analyte binding reagent) is one that selectively binds to the analyte of interest, preferably with high affinity, e.g., sufficient affinity to produce a detectable signal when the analyte is present. The amount of the analyte interacting reagent (e.g., analyte binding reagent) is sufficient to provide a readily detectable signal if/when the analyte is present in the sample. In some embodiments, the first liquid matrix is the same as the second liquid matrix. In some embodiments, the first liquid matrix is different from the second liquid matrix. Suitable liquid matrices include lipids, hydrocarbon oils, and fluorocarbon oils.

In any of the preceding embodiments, the first aqueous droplet can have a net ionic charge. In any of the preceding embodiments, the second aqueous droplet can have a net ionic charge that is the opposite of the net ionic charge of the first aqueous droplet.

In any of the preceding embodiments, the first aqueous droplet can comprise a first surfactant, and the first surfactant may be cationic, anionic, nonionic, or amphoteric. In any of the preceding embodiments, the first surfactant may comprise a membrane protein.

In any of the preceding embodiments, the second aqueous droplet can comprise a second surfactant, and the second surfactant may be cationic, anionic, nonionic, or amphoteric.

In any of the preceding embodiments, the second surfactant may comprise a membrane protein.

In any of the preceding embodiments, at least one of the first aqueous droplet and the second aqueous droplet can be stabilized by a surfactant which may be cationic, anionic, nonionic, or amphoteric.

In any of the preceding embodiments, the first surfactant can be ionic. In any of the preceding embodiments, the second surfactant can be ionic and have a charge that is the opposite of the charge of the first surfactant.

In any of the preceding embodiments, the merged droplet can comprise a fluorescent label or a fluorescent particle.

In any of the preceding embodiments, the second aqueous droplet can comprise comprise a fluorescent particle, such as a quantum dot, fluorescent protein or fluorescent molecule, or a polymeric particle that contains a quantum dot, fluorescent molecule or fluorescent protein, and this fluorescent particle is thus present in the merged droplet. In any of the preceding embodiments, the analyte interacting reagent (e.g., analyte binding reagent) can be associated with or bound to the quantum dot.

In any of the preceding embodiments, the merged droplet can comprise a magnetic particle. The magnetic particle may have an electrical charge.

In any of the preceding embodiments, the first liquid matrix may be immiscible with water. The first liquid matrix can be selected from lipids, hydrocarbon oils, and fluorocarbon oils. Optionally, the first liquid matrix may comprise an electrolyte, such as tetrabutylammonium hexafluorophosphate or tetrabutylammonium tetrafluoroborate.

In any of the preceding embodiments, the second liquid matrix may be immiscible with water. Independently from the first liquid matrix, the second liquid matrix can be selected from lipids, hydrocarbon oils, and fluorocarbon oils. Optionally, the second liquid matrix may comprise an electrolyte, such as tetrabutylammonium hexafluorophosphate or tetrabutylammonium tetrafluoroborate.

In any of the preceding embodiments, mixing of the first emulsion and the second emulsion can occur in an analytic chamber. In any of the preceding embodiments, contacting said first emulsion and said second emulsion can comprises mixing adjacent streams of the first emulsion and the second emulsion. In any of the preceding embodiments, contacting said first emulsion and said second emulsion can comprises mixing transverse streams of the first emulsion and the second emulsion. In any of the preceding embodiments, contacting said first emulsion and said second emulsion can comprises mixing perpendicular streams of the first emulsion and the second emulsion. In any of the preceding embodiments, contacting said first emulsion and said second emulsion can comprises mixing oblique streams of the first emulsion and the second emulsion. In any of the preceding embodiments, contacting said first emulsion and said second emulsion can comprises mixing opposed streams of the first emulsion and the second emulsion. In any of the preceding embodiments, contacting said first emulsion and said second emulsion can comprises mixing concentric streams of the first emulsion and the second emulsion.

In any of the preceding embodiments, contacting said first emulsion and said second emulsion can comprise mixing streams of the first emulsion and the second emulsion and at least one demulsifying agent.

In any of the preceding embodiments, contacting said first emulsion and said second emulsion can comprise mixing streams of the first emulsion and the second emulsion and at least one additional surfactant.

In any of the preceding embodiments, the signal generated by binding of the analyte with the analyte interacting reagent (e.g., analyte binding reagent) can be or comprise a fluorescent signal.

In any of the preceding embodiments, the signal can be induced by an excitation light comprising, consisting essentially of, or consisting of a non-polarized light. In any of the preceding embodiments, the signal can be induced by an excitation light comprising, consisting essentially of, or consisting of a linearly polarized light. In any of the preceding embodiments, the signal can be induced by an excitation light comprising, consisting essentially of, or consisting of a circularly polarized light. In any of the preceding embodiments, the signal can be induced by an excitation light comprising, consisting essentially of, or consisting of a elliptically polarized light.

In any of the preceding embodiments, the signal can be induced by an excitation light comprising, consisting essentially of, or consisting of a non-coherent light. In any of the preceding embodiments, the signal can be induced by an excitation light comprising, consisting essentially of, or consisting of a coherent light.

In any of the preceding embodiments, the signal can be induced by an excitation light comprising, consisting essentially of, or consisting of a continuous light. In any of the preceding embodiments, the signal can be induced by an excitation light comprising, consisting essentially of, or consisting of a pulsed light.

In any of the preceding embodiments, the signal can be induced by an excitation light comprising, consisting essentially of, or consisting of a light applied at a single incident angle. In any of the preceding embodiments, the signal can be induced by an excitation light comprising, consisting essentially of, or consisting of a light applied at a set of incidence angles.

In any of the preceding embodiments, an external electric field can be applied to the combined emulsion with a magnitude sufficient to modify the distribution of the electric field vector of an evanescent wave within each droplet and thereby affect the fluorescence emission.

In any of the preceding embodiments, the external electric field can comprise, consist essentially of, or consist of a constant electric field in a constant direction. In any of the preceding embodiments, the external electric field can comprise, consist essentially of, or consist of a pulsed electric field in a constant direction. In any of the preceding embodiments, the external electric field can comprise, consist essentially of, or consist of an oscillating electric field in a constant direction. In any of the preceding embodiments, the external electric field can comprise, consist essentially of, or consist of a constant field electric switching between multiple directions. In any of the preceding embodiments, the external electric field can comprise, consist essentially of, or consist of a pulsed electric field switching between multiple directions. In any of the preceding embodiments, the external electric field can comprise, consist essentially of, or consist of an oscillating electric field switching between multiple directions.

In any of the preceding embodiments, an external electric field can be applied to the combined emulsion with a magnitude sufficient to induce a distortion of the merged droplets. In any of the preceding embodiments, the external electric field can comprise, consist essentially of, or consist of a constant electric field in a constant direction. In any of the preceding embodiments, the external electric field can comprise, consist essentially of, or consist of a pulsed electric field in a constant direction. In any of the preceding embodiments, the external electric field can comprise, consist essentially of, or consist of an oscillating electric field in a constant direction. In any of the preceding embodiments, the external electric field can comprise, consist essentially of, or consist of a constant field electric switching between multiple directions. In any of the preceding embodiments, the external electric field can comprise, consist essentially of, or consist of a pulsed electric field switching between multiple directions. In any of the preceding embodiments, the external electric field can comprise, consist essentially of, or consist of an oscillating electric field switching between multiple directions.

In any of the preceding embodiments, the excitation light can be only applied to the combined emulsion. In any of the preceding embodiments, the signal can be or comprise a fluorescence emission and can be optionally detected after the merge event has occurred.

In some aspects, disclosed herein is a method for detection of an analyte interacting with an analyte interacting reagent (e.g., analyte binding reagent), comprising mixing a first emulsion and a second emulsion together at a flat surface in an analytic chamber and allowing said droplets to merge into merged droplets. In some embodiments, the first emulsion comprises one or more aqueous sample droplet within a water-immiscible host matrix, stabilized with a first charged surfactant, wherein the sample droplet or droplets comprise an analyte. In some embodiments, the second emulsion comprises one or more aqueous reagent droplet within a water-immiscible host matrix, stabilized with a second surfactant of opposite charge from the charge of the first charged surfactant. In some embodiments, the reagent droplet or droplets contain one or more fluorescent particle. In some embodiments, the fluorescent particle or particles comprise an analyte-binding reagent. In any of the preceding embodiments, each fluorescent particle can comprise a unique analyte interacting reagent (e.g., analyte binding reagent) on its surface.

In any of the preceding embodiments, the method can further comprise asserting or applying an excitation light at an angle sufficient to produce total internal reflection at said flat surface during said mixing process sufficient to cause fluorescence of the said fluorescent particle. In any of the preceding embodiments, the fluorescence can be dependent on fluorescent particle position within the electric field vector of an evanescent wave that arises from a refractive index difference between said flat surface and the droplet.

In any of the preceding embodiments, the method can further comprise detecting and/or measuring the magnitude of the fluorescence emission during said mixing process.

In any of the preceding embodiments, the method can further comprise determining the identity of the analyte interacting reagent (e.g., analyte binding reagent) used within each droplet from the pattern of fluorescent emission wavelengths from each droplet, wherein a change in the stochastic behavior of the magnitude of the fluorescence emission provides an indication of analyte presence/absence, a amount, level or concentration, and/or an activity such as a binding interaction.

In any of the preceding embodiments, the aqueous sample droplet and said reagent droplet can be electrostatically charged with opposing charges.

In any of the preceding embodiments, the aqueous sample droplets can each comprise at least one fluorescent reagent such as a fluorescent particle. In any of the preceding embodiments, the aqueous sample droplets can each comprise more than one fluorescent particle. In any of the preceding embodiments, said aqueous sample droplets and said aqueous reagent droplets can each comprise at least one fluorescent particle. In any of the preceding embodiments, said aqueous sample droplets can each comprise at least one magnetic particle. In any of the preceding embodiments, said aqueous reagent droplets can each comprise more than one magnetic particle. In any of the preceding embodiments, said aqueous sample droplets and said aqueous reagent droplets can each comprise at least one magnetic particle.

In any of the preceding embodiments, the magnetic particle may optionally have an electric charge. In any of the preceding embodiments, the sample droplets may contain magnetic particles of opposite charge from the magnetic particles in the reagent droplets.

In any of the preceding embodiments, said analytic chamber can be used to perform said mixing of said aqueous sample droplets and said reagent droplets. In any of the preceding embodiments, said mixing can be performed by or comprise flowing adjacent streams of aqueous sample droplets and aqueous reagent droplets in their respective water-immiscible host matrices. In any of the preceding embodiments, said mixing can be performed by or comprise flowing transverse streams of aqueous sample droplets and aqueous reagent droplets in their respective water-immiscible host matrices. In any of the preceding embodiments, said mixing can be performed by or comprise flowing perpendicular streams of aqueous sample droplets and aqueous reagent droplets in their respective water-immiscible host matrices. In any of the preceding embodiments, said mixing can be performed by or comprise flowing oblique streams of aqueous sample droplets and aqueous reagent droplets in their respective water-immiscible host matrices. In any of the preceding embodiments, said mixing can be performed by or comprise flowing opposed streams of aqueous sample droplets and aqueous reagent droplets in their respective water-immiscible host matrices. In any of the preceding embodiments, said mixing can be performed by or comprise flowing concentric streams aqueous sample droplets and aqueous reagent droplets in their respective water-immiscible host matrices. In any of the preceding embodiments, said mixing can be performed by or comprise flowing streams of aqueous sample droplets and aqueous reagent droplets in their respective water-immiscible host matrices combined with one or more streams of demulsification agents. In any of the preceding embodiments, said mixing can be performed by or comprise flowing streams of aqueous sample droplets and aqueous reagent droplets in their respective water-immiscible host matrices combined with one or more streams of surfactants.

In any of the preceding embodiments, the excitation light can be or comprise a non-polarized light. In any of the preceding embodiments, the excitation light can be or comprise a linearly polarized light. In any of the preceding embodiments, the excitation light can be or comprise a circularly polarized light. In any of the preceding embodiments, the excitation light can be or comprise an elliptically polarized light. In any of the preceding embodiments, the excitation light can be or comprise a non-coherent light. In any of the preceding embodiments, the excitation light can be or comprise a coherent light. In any of the preceding embodiments, the excitation light can be or comprise a continuous light. In any of the preceding embodiments, the excitation light can be or comprise a pulsed light. In any of the preceding embodiments, the excitation light can be or comprise a light applied at a single incident angle. In any of the preceding embodiments, the excitation light can be or comprise a light applied at a set of incidence angles.

In any of the preceding embodiments, an external electric field can be applied to said emulsions with a magnitude sufficient to modify the distribution of the electric field vector of an evanescent wave within each droplet and thereby affect the fluorescence emission. In any of the preceding embodiments, the external electric field can be or comprise a constant electric field applied in a constant direction. In any of the preceding embodiments, the external electric field can be or comprise a pulsed electric field applied in a constant direction. In any of the preceding embodiments, the external electric field can be or comprise an oscillating electric field applied in a constant direction. In any of the preceding embodiments, the external electric field can be or comprise a constant field electric switching between multiple directions. In any of the preceding embodiments, the external electric field can be or comprise a pulsed electric field switching between multiple directions. In any of the preceding embodiments, the external electric field can be or comprise an oscillating electric field switching between multiple directions.

In any of the preceding embodiments, an external electric field can be applied to said emulsions with a magnitude sufficient to induce a distortion of the spherical droplets into prolate spheroids and thereby cause hydrodynamic stress to binding interactions between the fluorescent particle and moieties bound to it. In any of the preceding embodiments, the external electric field can be or comprise a constant electric field applied in a constant direction. In any of the preceding embodiments, the external electric field can be or comprise a pulsed electric field applied in a constant direction. In any of the preceding embodiments, the external electric field can be or comprise an oscillating electric field applied in a constant direction. In any of the preceding embodiments, the external electric field can be or comprise a constant field electric switching between multiple directions. In any of the preceding embodiments, the external electric field can be or comprise a pulsed electric field switching between multiple directions. In any of the preceding embodiments, the external electric field can be or comprise an oscillating electric field switching between multiple directions.

In any of the preceding embodiments, the method can comprise applying the excitation light after the merge event has occurred. In any of the preceding embodiments, the method can comprise measuring the magnitude of the fluorescence emission after the merge event has occurred. In any of the preceding embodiments, the excitation light may be only applied after the merge event has occurred. In any of the preceding embodiments, the magnitude of the fluorescence emission may be only measured after the merge event has occurred.

In any of the preceding embodiments, the method can comprise compressing said sample droplet or droplets into a disk. In any of the preceding embodiments, the method can comprise compressing the reagent droplet or droplets into a disk. In any of the preceding embodiments, the method can comprise compressing the merged droplet or droplets into a disk.

In any of the preceding embodiments, the method can comprise allowing the sample droplet or droplets to float or sink to said flat surface. In any of the preceding embodiments, the method can comprise allowing the reagent droplet or droplets to float or sink to said flat surface. In any of the preceding embodiments, the method can comprise allowing the merged droplet or droplets to float or sink to said flat surface.

In any of the preceding embodiments, the method can comprise floating or sinking the sample droplet or droplets to said flat surface. In any of the preceding embodiments, the method can comprise floating or sinking the reagent droplet or droplets to said flat surface. In any of the preceding embodiments, the method can comprise floating or sinking the merged droplet or droplets to said flat surface.

In some aspects, disclosed herein is a method for detection of an interaction between an analyte in a sample and an analyte interacting reagent (e.g., analyte binding reagent), wherein the method comprises mixing a first aqueous emulsion and a second aqueous emulsion together to form a combined emulsion under conditions where droplets from the first emulsion can combine with droplets from the second emulsion to form merged droplets. In any of the preceding embodiments, the first aqueous emulsion can comprise droplets containing a portion of the sample in a water-immiscible host matrix, wherein the emulsion is stabilized with a charged surfactant. In any of the preceding embodiments, the second aqueous emulsion can comprise one or more analyte interacting reagent (e.g., analyte binding reagent)s in droplets in a water-immiscible host matrix. In any of the preceding embodiments, the second aqueous emulsion can be stabilized with a surfactant having the opposite charge from that of the charged surfactant in the first aqueous emulsion.

In any of the preceding embodiments, each analyte interacting reagent (e.g., analyte binding reagent) can be coupled to a fluorescent reagent, such as a fluorescent particle, e.g., quantum dots. For example, each analyte interacting reagent may be on the surface of the fluorescent particle.

In any of the preceding embodiments, the method can further comprise directing excitation light to the combined emulsion during and/or after mixing, sufficient to cause fluorescence of said fluorescent particles, wherein said fluorescence is dependent on the position of each fluorescent particle within the electric field vector of an evanescent wave that arises from a refractive index difference between the host matrix and the droplet.

In any of the preceding embodiments, the method can further comprise detecting the fluorescence emission and/or measuring the magnitude of the fluorescence emission from the merged droplets.

In any of the preceding embodiments, the method can further comprise determining the identity of each affinity binding reagent within each merged droplet from the pattern of fluorescent emission wavelengths from each merged droplet.

In any of the preceding embodiments, a change in the stochastic behavior of the magnitude of the fluorescence emission may provide an indication of analyte presence/absence, an amount, level or concentration, and/or an activity such as a binding activity.

In any of the preceding embodiments, the aqueous sample droplet and the reagent droplet can be electrostatically charged with opposing charges.

In any of the preceding embodiments, the aqueous sample droplets can each contain at least one fluorescent particle. In any of the preceding embodiments, the aqueous reagent droplets can each contain more than one fluorescent particle. In any of the preceding embodiments, the aqueous sample droplets and the aqueous reagent droplets can each contain at least one fluorescent particle. In any of the preceding embodiments, the aqueous sample droplets can each contain at least one magnetic particle. In any of the preceding embodiments, the aqueous reagent droplets can each contain more than one magnetic particle. In any of the preceding embodiments, the aqueous sample droplets and the aqueous reagent droplets can each contain at least one magnetic particle.

In any of the preceding embodiments, said analytic chamber can be used to perform said mixing of said aqueous sample droplets and said reagent droplets. In any of the preceding embodiments, said mixing can comprise: flowing adjacent streams of aqueous sample droplets and aqueous reagent droplets in their respective water-immiscible host matrices; flowing transverse streams of aqueous sample droplets and aqueous reagent droplets in their respective water-immiscible host matrices; flowing perpendicular streams of aqueous sample droplets and aqueous reagent droplets in their respective water-immiscible host matrices; flowing oblique streams of aqueous sample droplets and aqueous reagent droplets in their respective water-immiscible host matrices; flowing opposed streams of aqueous sample droplets and aqueous reagent droplets in their respective water-immiscible host matrices; flowing concentric streams aqueous sample droplets and aqueous reagent droplets in their respective water-immiscible host matrices; flowing streams of aqueous sample droplets and aqueous reagent droplets in their respective water-immiscible host matrices combined with one or more streams of demulsification agents; flowing streams of aqueous sample droplets and aqueous reagent droplets in their respective water-immiscible host matrices combined with one or more streams of surfactants, and/or a suitable combination thereof.

In any of the preceding embodiments, the excitation light may be or comprise a non-polarized light, a linearly polarized light, a circularly polarized light, an elliptically polarized light; a non-coherent light; a coherent light; a continuous light; a pulsed light; a light applied at a single incident angle; a light applied at a set of incidence angles; and/or any suitable combination thereof.

In any of the preceding embodiments, an external electric field can be applied to said emulsions with a magnitude sufficient to modify the distribution of the electric field vector of an evanescent wave within each droplet and thereby affect the fluorescence emission. In any of the preceding embodiments, the external electric field can comprise, consist essentially of, or consist of: a constant electric field in a constant direction; a pulsed electric field in a constant direction; an oscillating electric field in a constant direction; a constant field electric switching between multiple directions; a pulsed electric field switching between multiple directions; an oscillating electric field switching between multiple directions; and/or any suitable combination thereof.

A. Compositions and Methods for Analyzing an Analyte Using Droplets in Suspension In some aspects, provided herein is a method comprising passing a pair of disparate emulsions into an analytic chamber and mixing the emulsions together while fluorescence is monitored. In some embodiments, one emulsion is formed of droplets of aqueous sample to be analyzed, and the other emulsion is formed of droplets of water containing a fluorescent particle that may bind to the sample. In some embodiments, the analytic chamber allows the droplets to be distributed in bulk suspension. Characteristics of the fluorescence are measured to provide concentration and binding interaction data for various analytes, which can provide useful information about biological samples.

In some embodiments, an emulsion of aqueous sample droplets containing analyte is mixed with an emulsion of aqueous reagent droplets in an analytic chamber. In some embodiments, the sample droplets contain analytes to be measured. In some embodiments, the sample droplet surfaces are stabilized with a cationic surfactant, and each may contain zero, one, or multiple fluorescent particles. In some embodiments, the reagent droplet surfaces are stabilized with an anionic surfactant, and each may contain one or multiple fluorescent particles, at least one of which has a surface coated with a reagent that can bind to said analytes.

In some embodiments, the sample droplet surfaces are stabilized with an anionic surfactant, and the reagent droplet surfaces are stabilized with a cationic surfactant.

In some embodiments, the surfactant is an amphiphilic molecule containing a polar, hydrophilic group and a nonpolar, hydrophobic group. In some embodiments, the polar, hydrophilic group is positively charged by a cation moiety. In some embodiments, the polar, hydrophilic group is negatively charged by an anion moiety. In some embodiments, the polar, hydrophilic group is nonionic. In some embodiments, the polar, hydrophilic group is amphoteric.

In some embodiments, the sample droplet surfaces and the reagent droplet surfaces are both stabilized with surfactants of the same polarity, either a cationic surfactant or an anionic surfactant.

Examples of cationic surfactants are benzalkonium chloride, benzethonium chloride, cetrimonium bromide, stearalkonium chloride, tetramethylammonium hydroxide, and thonzonium bromide. Examples of anionic surfactants are sodium alkyl sulfates, alkylbenzene sulfonates, chlorosulfolipids, perfluoroalkyl sulfonic acids, phospholipids, and sulfolipids. Examples of nonionic surfactants are alkyl polyglycosides, alkyl glucosides, cetyl alcohol, glycerol monostearate, maltosides, nonoxynols, polysorbates, and sorbitan stearates. Examples of amphoteric surfactants are imino propionates, imino acetates, lauryl betaine, betaine citrate, sodium hydroxymethylglycinate, sodium lauroamphoacetate, and (carboxymethyl)dimethyloleylammonium hydroxide. Amphoteric surfactants are also known as zwitterionic surfactants.

In some embodiments, each emulsion is stabilized by the surfactants because their droplets have a like surface charge that repels other droplets, minimizing coalescence of the droplets. In some embodiments, the surfactants self-assemble onto the surface of each droplet such that the polar, hydrophilic group of the surfactant molecule is toward the droplet, and the nonpolar, hydrophobic group of the surfactant molecule is away from the droplet.

In some embodiments, the sample droplet surfaces or the reagent droplet surfaces are populated with proteins that can occur as membrane proteins in cells. Such proteins have a hydrophobic component that extends into the phospholipid bilayer of cell membranes. Herein, such proteins are considered to be surfactants.

In some embodiments, the droplets of each emulsion are suspended in a host matrix. The host matrix of each emulsion is a liquid or liquid crystal that is water-immiscible. Examples of host matrices are lipids, hydrocarbon oils, and fluorocarbon oils. Commercially available fluorocarbon oils include Fluorinert FC-40, Fluorinert FC-43, Fluorinert FC-70, Fluorinert FC-75, Fluorinert FC-3283. A host matrix may be chosen such that it forms a gel or glass at low temperatures, to enhance storage stability over long time periods.

In some embodiments, the density of the droplets relative to its host matrix may impose gravitationally-driven movement of the droplets, either floating upwards or sinking downwards. This movement tends to compact the droplets together, which lessens emulsion stability. This gravitationally-driven movement is mitigated by Brownian motion, such that emulsion stability is improved.

In some embodiments, the emulsions can be formed using known methods by combining a slow flow of aqueous media with a fast flow of water-immiscible media within a flow cell. This method generates aqueous droplets having a highly uniform size within a water-immiscible host matrix. Secondary emulsions that are composed of a water-immiscible droplet within an aqueous droplet that is itself within a water-immiscible host matrix can also be formed.

In some embodiments, the aqueous media contain fluorescent particles, such that the resulting aqueous droplets contain the fluorescent particles. The concentration of the fluorescent particles in the aqueous media may be set such that statistically there is only one fluorescent particle per aqueous droplet. Subsequent handling of the resulting droplets may then implement fluorescence-based sorting to yield a population of droplets containing a single fluorescent particle. The internal water-immiscible droplet of a secondary emulsion may also contain fluorescent particles.

Fluorescent particles that are quantum dots typically have a semiconductor core surrounded by a protective layer, and are typically about 5 nm diameter. Additionally, a layer of reagent that can bind to an analyte is immobilized on the outer surface. Typical protein analytes have a size range from 10 nm to 50 nm diameter. This means that attachment of a protein analyte to the fluorescent particle may produce a large change in the hydrodynamic properties of the fluorescent particle.

Fluorescent particles with a bola structure may also be synthesized and used herein. These would consist of two fluorescent particles connected by a flexible linkage. An example of the use of such a bola structure would be for Fluorescence Resonant Energy Transfer (FRET) analysis. Another example would be the use of a nucleic acid strand exhibiting a binding interaction with the flexible linkage and affecting its mobility, thereby affecting the mobility of the fluorescent particles. Other types of fluorescent particles include fluorescent proteins, fluorescent molecules, and polymeric spheres that contain quantum dots, fluorescent proteins, or fluorescent molecules.

The excitation spectrum of quantum dots is quite broad, meaning that one excitation light can be used to produce fluorescence from a wide variety of quantum dots. Typically, ultraviolet light is used for quantum dot excitation. Excitation is produced from the electric field vector of the excitation light.

The emission spectrum of quantum dots is relatively narrow, and is defined by the semiconductor composition and physical size. Single quantum dots have a fluorescence emission spectrum band (color) of about 10 to 15 nm width at room temperature in the visible range. Commercially available quantum dots have aggregate colors of 30 to 50 nm width.

Mixing of the pair of disparate emulsions (sample emulsion and reagent emulsion) may be implemented by a pair of streams that are continuously flowed into an analytic chamber. The pair of disparate emulsions is mixed together by diffusion or by turbulence. Turbulence may be added by the use of static obstacles to the flow, or by the use of moving components. The pair of streams may be adjacent, transverse, perpendicular, oblique, opposed, or concentric.

Alternatively, the mixing of the pair of disparate emulsions may be implemented by a pair of streams that are flowed into an analytic chamber carrying plugs of the emulsions; the flows are stopped when the plugs are delivered to the analytic chamber. The pair of disparate emulsions is mixed together by diffusion or by turbulence. Turbulence may be added by the use of static obstacles to the flow, or by the use of moving components. The pair of streams may be adjacent, transverse, perpendicular, oblique, opposed, or concentric.

Alternatively, the mixing of the pair of disparate emulsions may be implemented by injecting a stream of one emulsion into an analytic chamber that contains the other emulsion. The pair of disparate emulsions is mixed together by diffusion or by turbulence. Turbulence may be added by the use of static obstacles to the flow, or by the use of moving components.

Alternatively, the mixing of the pair of disparate emulsions may be implemented by repeatedly compressing and expanding the thickness of the analytic chamber.

Figure 13:
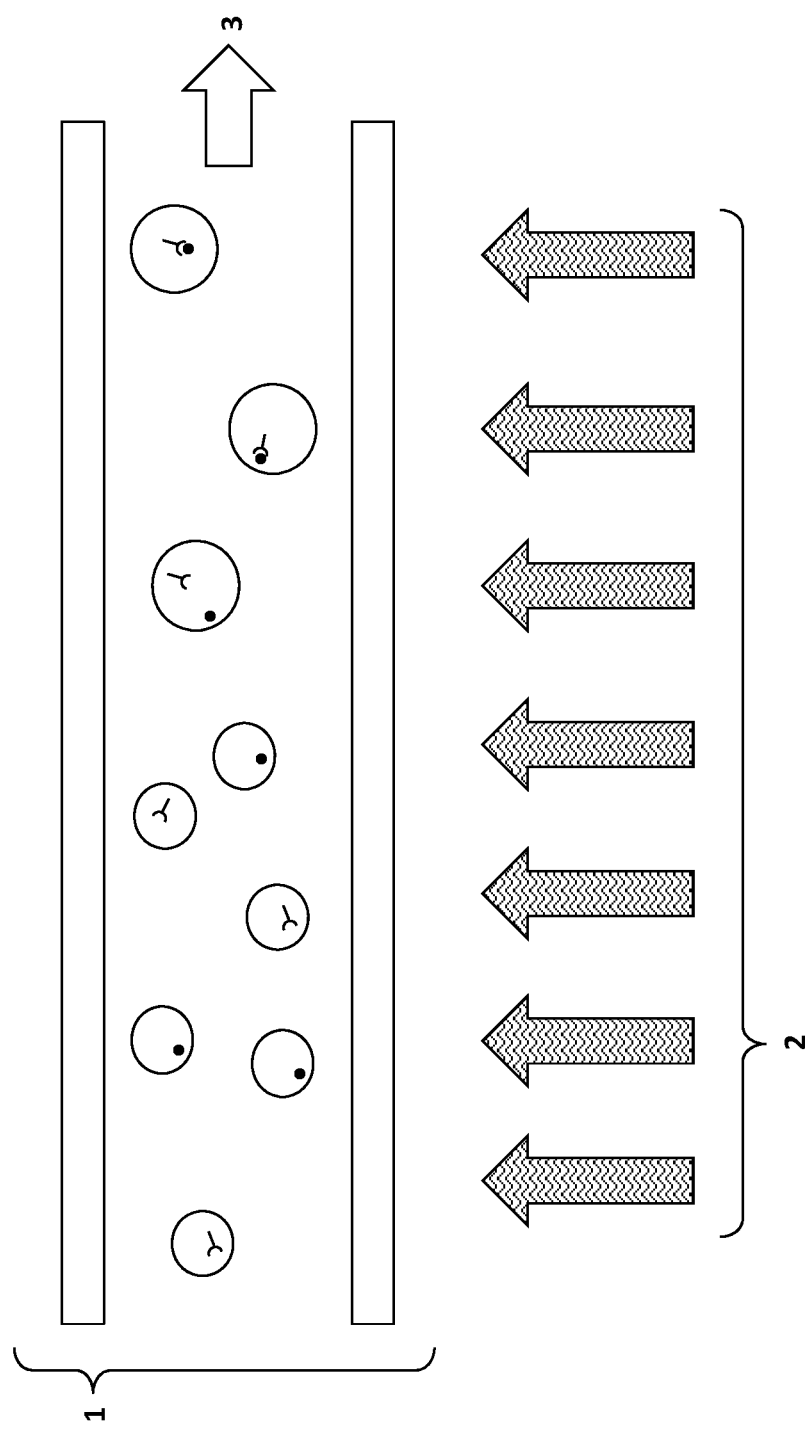
FIG. 13 is a schematic of an analytic cell where excitation light is passed through the mixed emulsions, according to certain embodiments of the present disclosures.
Figure 14:
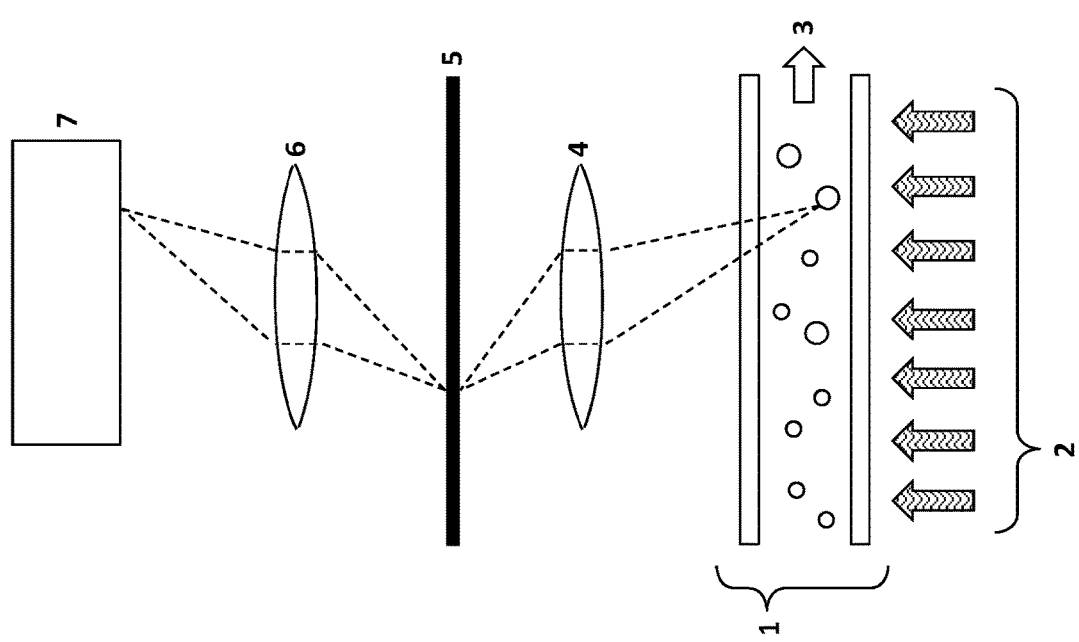
FIG. 14 is a schematic of an optical system for measuring fluorescence emission light from the analytic cell of FIG. 13, according to certain embodiments of the present disclosures.

One example of a device using a method of the invention is depicted schematically in FIGS. 13-14. For convenient discussion, the examples in FIGS. 13-14 involves a first emulsion of aqueous droplets that contain a sample that contains or may contain an analyte of interest, suspended in a suitable fluid matrix, and a second emulsion of aqueous droplets that contain an analyte binding reagent, suspended in a second suitable fluid matrix. The first emulsion and the second emulsion can be mixed together, e.g., by bringing a flowing stream of the first emulsion (referred to as sample droplets or the sample stream) and a flowing stream of the second emulsion (referred to as the reagent droplets or reagent stream) together in an analytic chamber. The analytic chamber is constructed such that an excitation light (2) can be applied to the mixing emulsions, as shown in FIG. 13. An analytic chamber (1) contains sample droplets and reagent droplets that merge as the two separate emulsions mix, eventually flowing out (3) of the analytic cell (1). Excitation light (2) is applied such that it passes through a wall of the analytic chamber (1) to reach the droplets inside.

The analytic chamber is constructed such that fluorescence emission can be emitted to an optic system, as shown in FIG. 14. An analytic chamber (1) contains sample droplets and reagent droplets that merge, eventually flowing out (3) of the analytic chamber (1). Excitation light (2) is applied such that it passes through a wall of the analytic chamber (1) to reach the droplets. A lens (4) focuses the fluorescence emission from the droplets onto a diffraction grating (5). Another lens (6) focuses the light from the diffraction grating onto a camera (7).

The geometry of the analytic chamber may be made thin along one plane, in order to minimize scattering of the excitation light amongst multiple droplets. This ensures that the magnitude of the electric field vector across all droplets is consistent and known. Optionally, the thickness of the analytic chamber is adjustable, to allow mixing of the droplets by oscillating the thickness of the analytic chamber. Optionally, the analytic chamber may be made sufficiently large such that multiple mixtures of droplets may be contained, separated by a material such as water or air. For example, an analytic chamber may be constructed such that it has a large area containing a multitude of non-aqueous droplets within a water matrix, where the non-aqueous droplets contain a multitude of aqueous droplets that are of a composition as described herein. This would allow multiplying the size of the address space. Such non-aqueous droplets may contain fluorescent labels to differentiate them.

Upon mixing of the two disparate emulsions together, pairs of droplets can merge together to form merged droplets of summed mass, which mixes an analyte from droplets of the sample stream with an analyte binding reagent, such as an antibody on a fluorescent particle, from the droplets of the reagent stream, and allows a binding interaction to occur inside a merged droplet. Selective merging of the analyte (sample) droplets with reagent droplets is promoted by the methods described below, whereby droplets of each of the separate streams are adapted to minimize merging with droplets from the same stream, and preferentially merge with droplets from the other stream. This is referred to as a binary merge event.

The binary merge event can be promoted or caused by one or more of the following seven mechanisms. Other mechanisms may also be implemented using the basic underlying principles to minimize merging of 'like' droplets, e.g., merging of sample droplets with sample droplets, or of reagent droplets with other reagent droplets, and to instead promote merging of unlike droplets, i.e., merging of a sample droplet with a reagent droplet.

Figure 15:
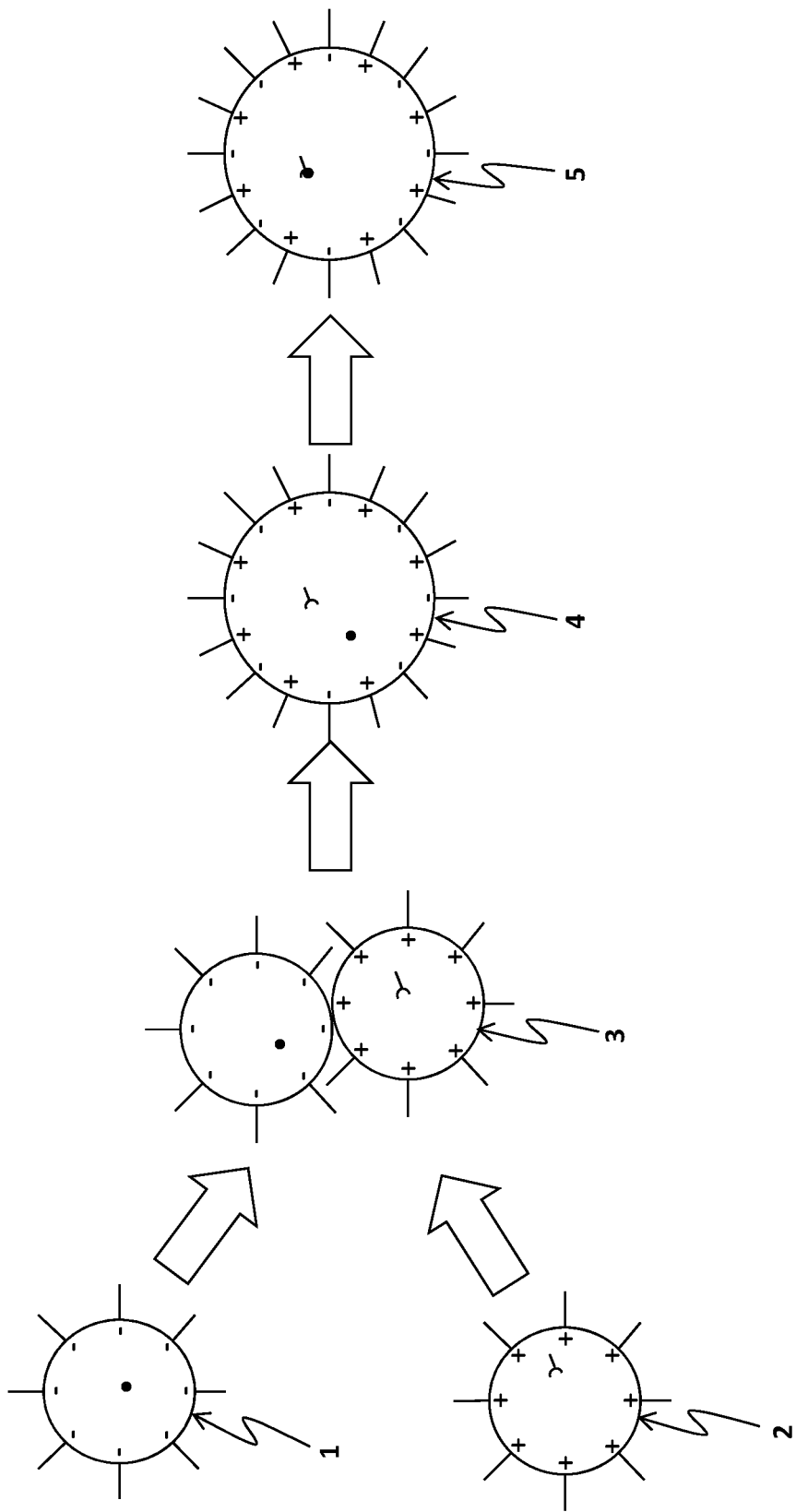
FIG. 15 is schematic of merging droplets having opposite surfactant charges, according to certain embodiments of the present disclosures.

A first mechanism is by electrostatic attraction of oppositely-charged surfactants on the droplet surfaces, as shown in FIG. 15. If the sample droplet surfaces (2) are stabilized with a cationic surfactant and the reagent droplet surfaces (1) are stabilized with an anionic surfactant (or vice versa), then their surfaces charges may cause attraction between a sample droplet and a reagent droplet. This leads to contact of the two droplets (3), followed by a binary merge event (4).

After the binary merge event, the surfactant charges neutralize each other, such that the net charge on the resulting droplet is neutral. Since that resulting neutrally-charged droplet does not electrostatically attract either positively charged or negatively charged droplets, and thus there is no further merging with other droplets. The result of mixing of the two emulsions is thus largely constrained to binary merge events.

The surfactant charges may be selected such that binary merge events produce droplets with a small non-zero net charge. This would be small enough to minimize further merge events into the droplet, while large enough to provide a degree of emulsion stabilization.

After the binary merge event, the sample and reagent may exhibit a binding interaction (5). The binding interaction may be detected by methods described herein, and the appearance and/or magnitude of the binding interaction or signal representing the binding interaction can be used to determine the presence or amount of analyte in the sample.

Figure 16:
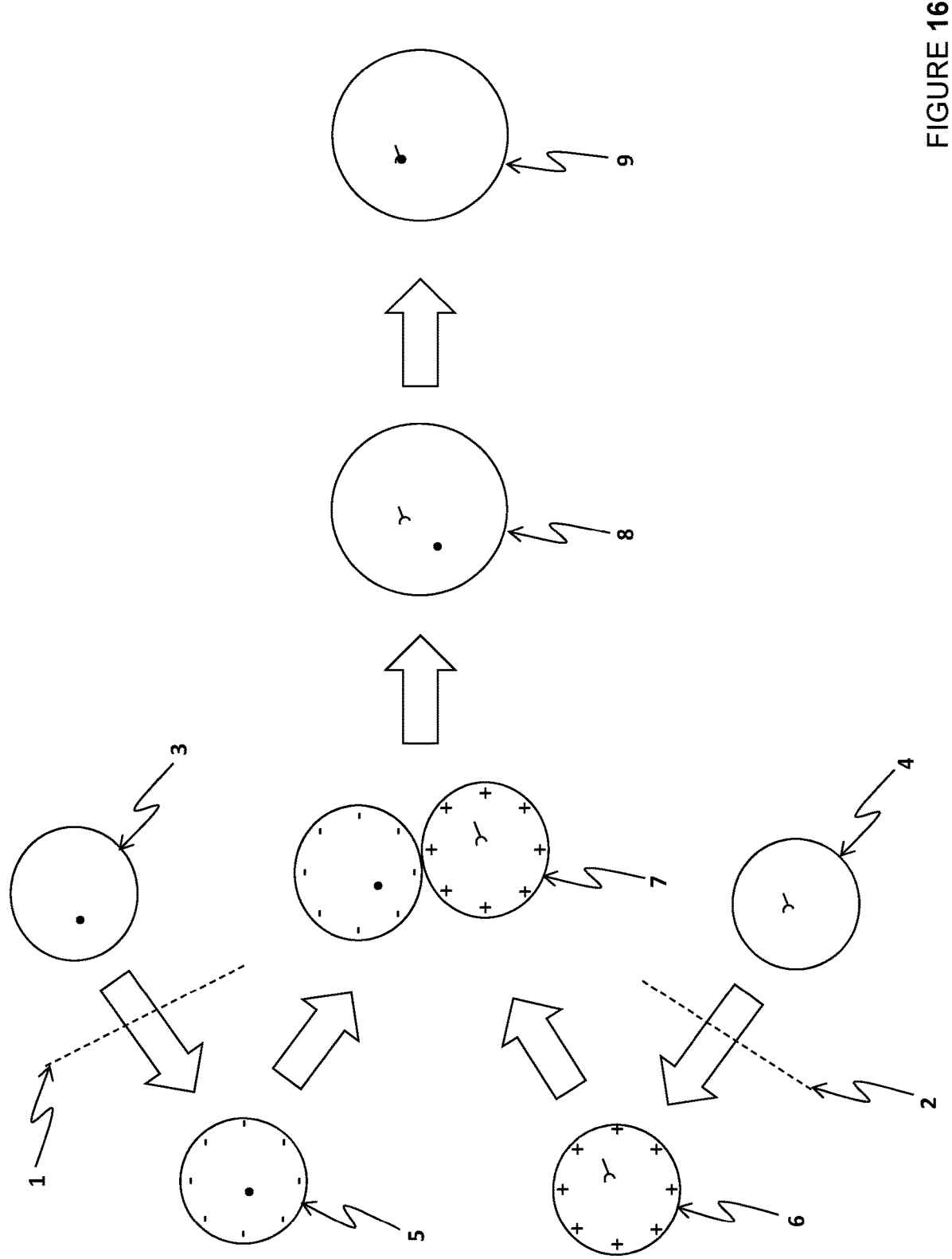
FIG. 16 is a schematic of merging droplets having opposite electrostatic charges, according to certain embodiments of the present disclosures.

A second mechanism to promote selective merging of sample droplets with reagent droplets is by electrochemical charging of the droplets, as shown in FIG. 16. Droplets are electrochemically charged by passing them to metallic electrodes at an electric potential sufficient to cause charge transfer between the metal and the droplet, and thereby cause an oxidation or reduction reaction to occur. An example of an oxidation reaction is ferrous (2+) ion to ferric (3+) ion plus 1 electron transferred to a metallic electrode. If the water-immiscible host matrix contains an electrolyte, then the charge transferred into the droplet is balanced by opposing ionic charges of the electrolyte on the outer surface of the droplet. Examples of such electrolytes are tetrabutylammonium hexafluorophosphate and tetrabutylammonium tetrafluoroborate. Care should be exercised in the selection of electrolyte, because an electrolyte may reduce the zeta-potential of the droplet surfaces and lead to uncontrolled demulsification. If the sample droplets (4) are given a positive electrochemical charge at an electrode (2) and the reagent droplets (3) are given a negative electrochemical charge at an electrode (1) (or vice versa), then their opposing surface charges may cause attraction between a sample droplet (6) and a reagent droplet (7). This leads to contact of the two droplets (7), followed by a binary merge event (8).

The attraction due to the electrochemical charge differential needs to be greater than the repulsion due to like-charged surfactants, if present. Care must be taken to minimize electric field gradients, which can cause demulsification.

After the binary merge event, the sample and reagent may exhibit a binding interaction (9).

Figure 17:
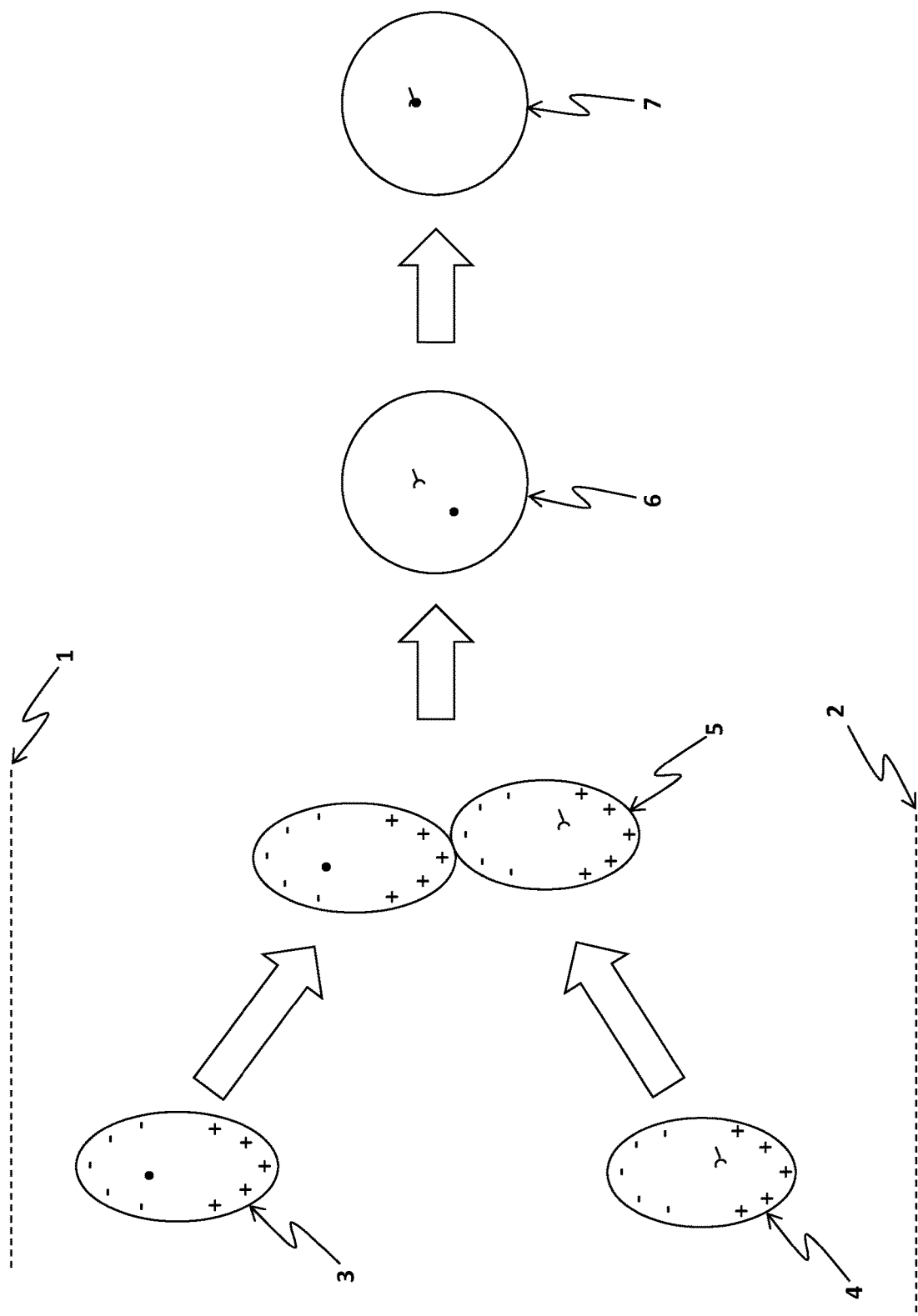
FIG. 17 is a schematic of merging droplets in an external electric field, according to certain embodiments of the present disclosures.

A third mechanism to promote selective merging of sample droplets with reagent droplets is by assertion of an externally-applied electric field to a mixed population of sample droplets and reagent droplets, as shown in FIG. 17. The externally-applied electric field between a positive grid (1) and a negative grid (2) induces a separation of charges within the sample droplet (4) and reagent droplet (3), such that one side is positively charged, and the other side is negatively charged. For a dilute suspension of droplets, oppositely-charged sides may cause attraction between droplets (5), followed by a binary merge event (6). This mechanism allows the useless merging of two sample droplets together, and allows the useless merging of two reagent droplets together; however, with continual optical tracking, the resulting droplets can be excluded from the final dataset.

The angle of the externally-applied electric field may be dynamically adjusted throughout the droplet merging in order to minimize merging of two sample droplets or merging of two reagent droplets.

A dynamically-adjusted externally-applied light that is absorbed by the host matrix is focused on the interstices between droplets that are not to merge. Local heating pushes them apart.

After the binary merge event, the sample and reagent may exhibit a binding interaction (7).

Figure 18:
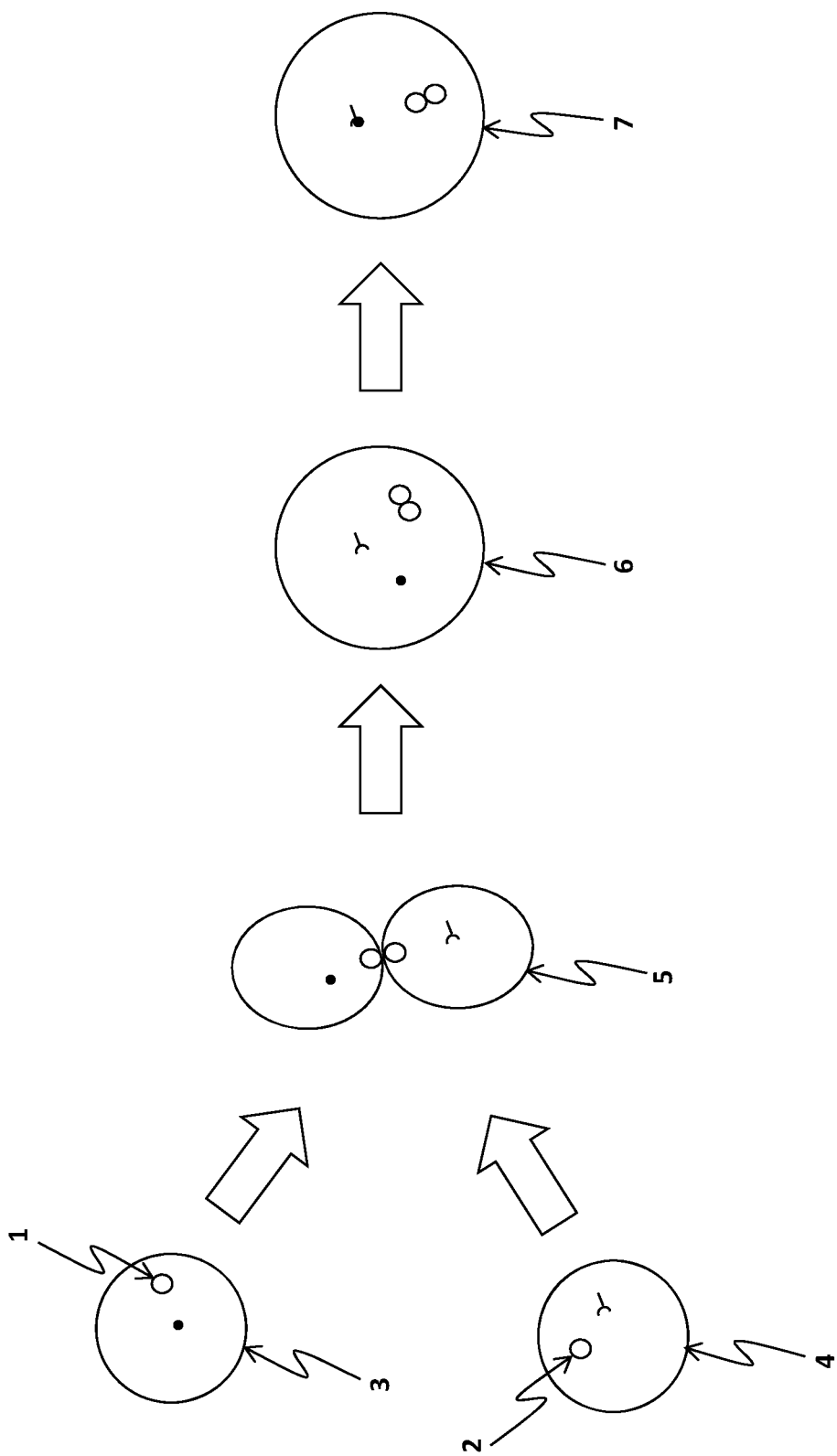
FIG. 18 is a schematic of merging droplets having magnetic particles within an external magnetic field, according to certain embodiments of the present disclosures.

A fourth mechanism to promote selective merging of sample droplets with reagent droplets is by addition of magnetic particles to the droplets when they are first generated, followed by an externally-applied magnetic field, as shown in FIG. 18. The magnetic field causes the magnetic particle (2) in a sample droplet (4) and the magnetic particle (1) in a reagent droplet (3), to be attracted to each other, due to magnetization of the magnetic particles. In consequence, the droplets that the magnetic particles are embedded in are attracted to each other (5), followed by a binary merge event (6) that is caused by the magnetic particles touching each other and breaking the interfacial barrier of the droplets. Alternatively, the magnetic particles may have opposing electric charges in the sample and reagent droplets. After mixing of the sample and reagent droplets, the oppositely charged magnetic particles may exhibit a degree of attraction to each other. This degree of attraction may cause the Brownian motion of the magnetic particles to be statistically closer to each other, rather than randomly distributed across the droplets. The degree of attraction may be enhanced by the application of a suitable magnetic field that is strong enough to cause the magnetic particles to tend to position themselves nearer each other, but not so strong that the magnetic particles overcome Brownian motion entirely and stick together. The subsequent application of a strong magnetic field then causes the magnetic particles to stick together, thereby breaking the interfacial barrier of the droplets, resulting in a binary merge event. Such a merge event would only occur between a sample droplet and a reagent droplet, even if the droplets are in close proximity, such as during flocculation.

After the binary merge event, the sample and reagent may exhibit a binding interaction (7).

Figure 19:
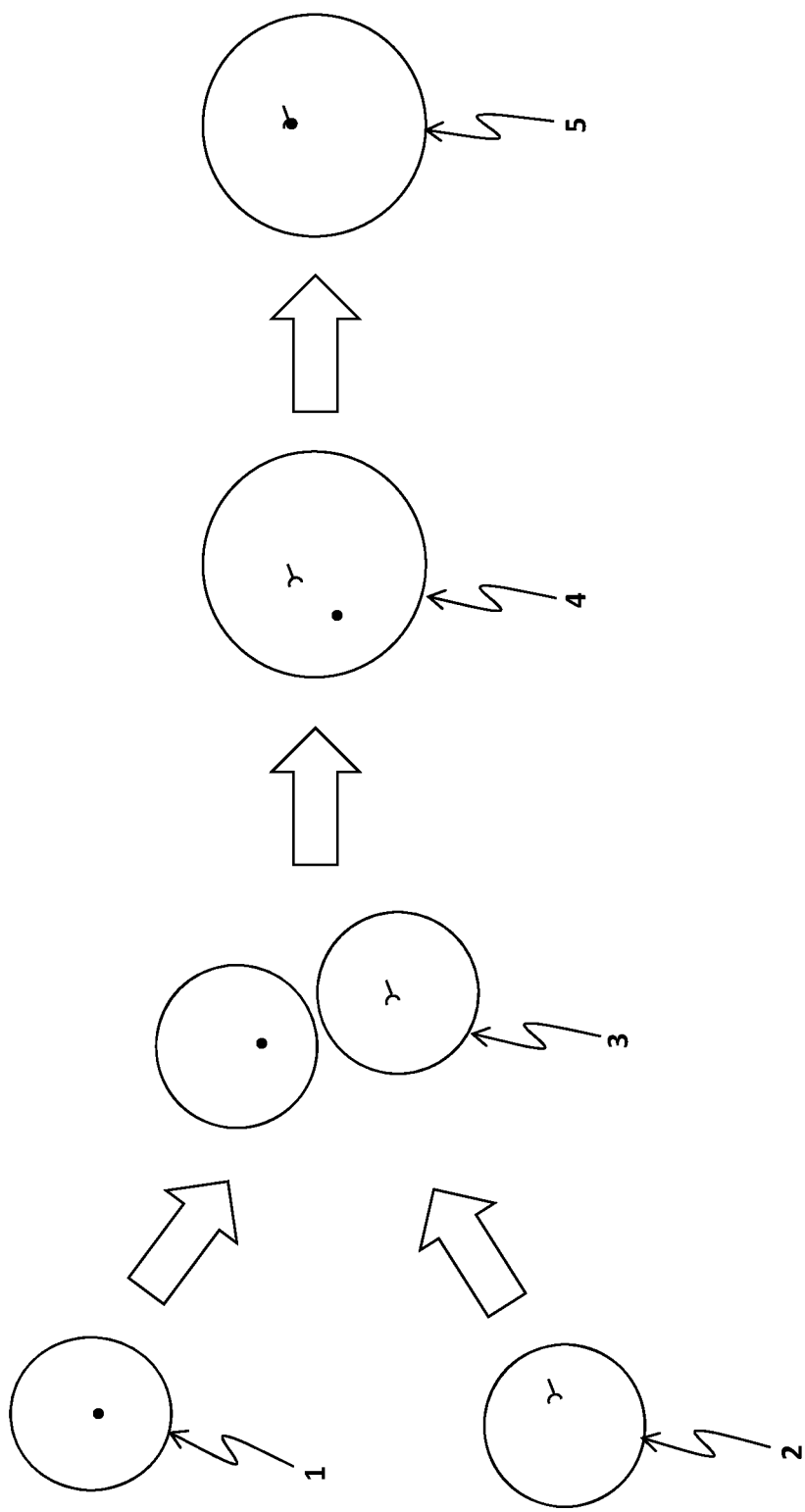
FIG. 19 is a schematic of merging droplets that combine randomly, according to certain embodiments of the present disclosures.

A fifth mechanism to promote selective merging of sample droplets with reagent droplets is by just letting the droplets randomly merge, and selecting the merge events of interest during data processing, as shown in FIG. 19. A sample droplet (2) and a reagent droplet (1) randomly touch (3) due to Brownian motion, followed by a binary merge event (4). This merging may be assisted by a demulsification technology, such an electric field gradient.

After the binary merge event, the sample and reagent may exhibit a binding interaction (5).

Figure 20:
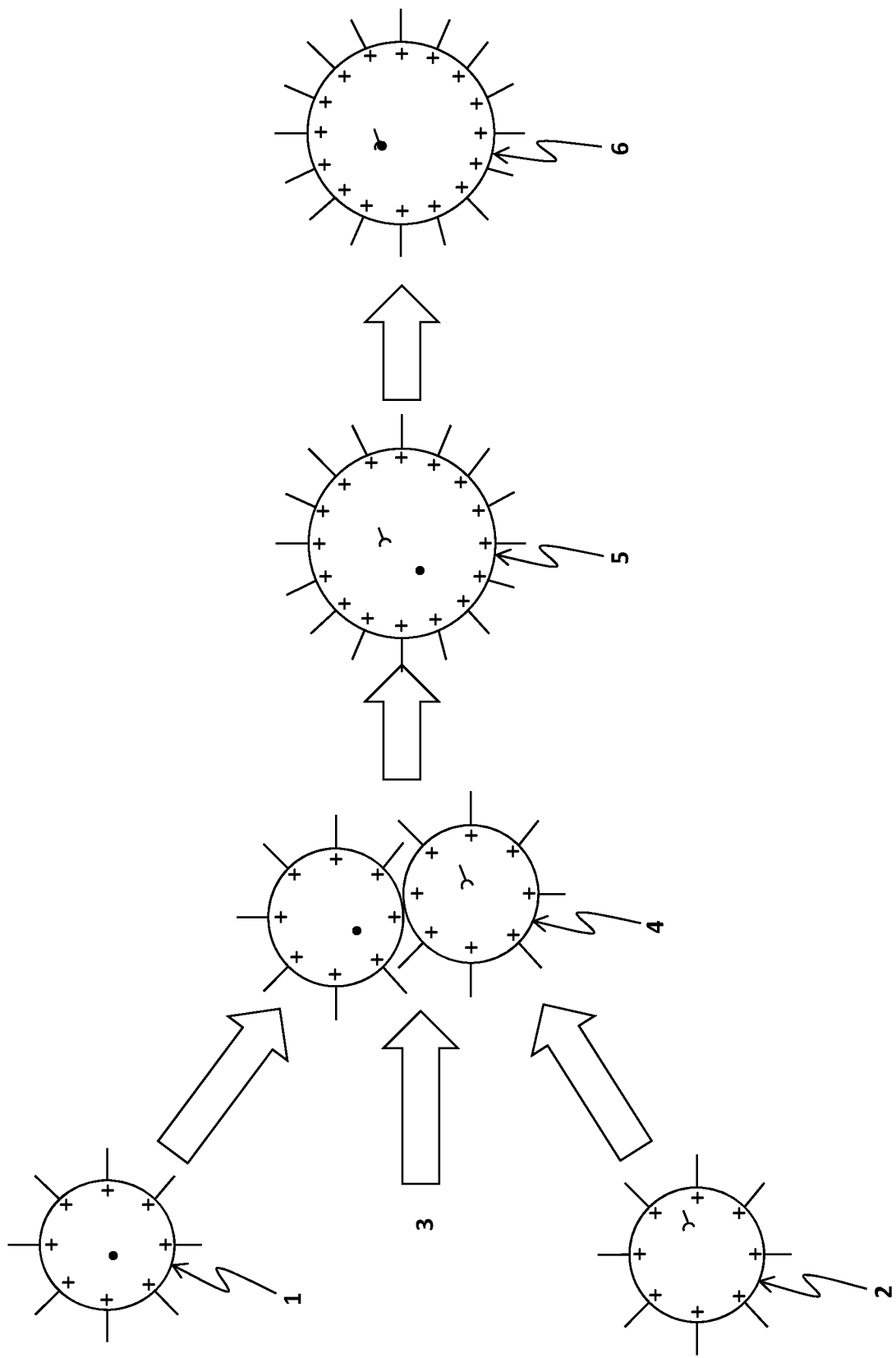
FIG. 20 is a schematic of merging droplets where merging of droplets is assisted with a stream of a demulsification agent, according to certain embodiments of the present disclosures.

A sixth mechanism to promote selective merging of sample droplets with reagent droplets is by combining a stream of sample emulsion, a stream of reagent emulsion, and a stream of water-immiscible host matrix containing a demulsification agent, as shown in FIG. 20. A stream containing a sample droplet (2), a stream containing a reagent droplet (1), and a stream containing a demulsification agent (3) are combined. The demulsification agent lessens the surfactant stabilization (4) of the sample droplets and the reagent droplets sufficient to promote merging of droplets (5).

Alternatively, a surfactant can be used in place of the demulsification agent. The surfactant interacts with the droplet surfaces to change the structure of the surface and near-surface charges (for example the Zeta potential) such that merging or stabilization is achieved.

A seventh mechanism to promote selective merging of sample droplets with reagent droplets is to apply an optical signal to a flocculated mixture of sample and reagent droplets. Specific junctions between two droplets are targeted with a focused beam of light that induces merging of the two droplets.

After the binary merge event, the sample and reagent may exhibit a binding interaction (6).

Any one of the first to seventh mechanisms may be used alone or in combination with one or more other mechanism described herein or known to one of skill in the art, in any suitable order. Any two or more of the first to seventh mechanisms may be used in combination in any suitable order.

For any of the seven mechanisms described above, in addition to binary merge events, other types of merge events are possible. For example, droplets of disparate size may be merged, where multiple small droplets may merge into a single large droplet to produce a larger merged droplet. Binary merge events may be assisted by the use of a momentary electric field, which induces charge differentials across droplets that help with merging the droplets.

Flocculation may occur during mixing of the sample and reagent droplets. This may be minimized by using only low concentrations of surfactants, and low concentrations of droplets. Flocculation may also be minimized by using narrow streams of sample and reagent droplets during the mixing stage; this reduces the probability of multiple droplets sticking together if each of the streams delivers one droplet at a time. Alternatively, flocculation may be acceptable if the analytic chamber is thin enough to ensure that the droplets stick together only along a flat plane; binary merge events would be more probable between oppositely-charged droplets and would be monitored over time.

In some embodiments, either sample droplets or reagent droplets or both contain a fluorescent dye or fluorescent particle such as a quantum dot, which can be used to monitor mixing and to provide a signal of a binding interaction. In some embodiments, the fluorescent dye or fluorescent particle is chemically associated with, and optionally covalently bound to, the analyte binding reagent.

During the process of mixing sample droplets with reagent droplets, excitation light illuminates both types of droplets, producing fluorescence emission light which is continuously monitored and tracked for each fluorescent particle, from before a merge event occurs, through after its completion.

Alternatively, fluorescence emission light is only monitored for merged droplets after the merge event has occurred.

The host matrix of each emulsion is preferably transparent to the excitation light.

The excitation light may be non-polarized. The excitation light may be linearly, circularly, or elliptically polarized. The excitation light may be coherent. The excitation light may be pulsed. The excitation light may be applied at a variety of incidence angles to the analytic chamber.

Stray excitation light is removed by the use of a matching optical filter.

Alternatively, the stray excitation light may be used to image the droplets for use in data processing, such as monitoring of bacteria within the droplets, or monitoring of pH-sensitive dyes.

Alternatively, additional light may be used for the intended purpose of imaging the droplets for use in data processing, such as monitoring of bacteria within the droplets, or monitoring of pH-sensitive dyes.

The fluorescence emission light from each fluorescent particle behaves as a point source and is emitted in all directions. This light is also refracted and diffracted by the droplet that contains the fluorescent particle, and refracted and diffracted by nearby droplets.

The mixing process can be optically monitored by an imaging lens, diffraction grating, and camera. The camera collects a continual series of camera images during the mixing process. The images are formed of the point sources by focusing with lenses and dispersion by a diffraction grating. The diffraction grating disperses each point source into a spectral streak, such that a camera image consists of many spectral streaks. As each fluorescent particle moves with its droplet during the mixing process, the continual series of camera images captures the movement of the associated spectral streaks. Each streak is tracked, and its behavior over time is extracted by image-processing software.

The identity of the reagent and sample combination for each droplet is determined by the wavelength pattern contained in each spectral streak. The wavelength pattern is a combination of the colors for each fluorescent particle within a droplet. The average magnitudes of the colors determine the count of each type of fluorescent particle within a droplet.

The 30 to 50 nm width of each color means that only about nine colors can be spectrally distinguished when using quantum dot particles. For a collection of merged droplets that each contain only one fluorescent particle, there are thus only nine combinations of sample and reagent that can be unambiguously identified simultaneously within the collection. The fluorescent particles function as labels having an address space of only nine combinations.

However, if the merged droplets contain multiple colors and multiple quantum dots, then the address space is considerably larger. For example, a merged droplet may contain a reagent-labeled red quantum dot, an unlabeled green quantum dot, and three un-labeled blue quantum dots. With nine possible colors and three possible magnitudes per color, the address space becomes the summation of $r(n!/(r!(n-r)!)$ for $r=1$ to $n$, where $n=9\times3=27$. This gives a total of 2,359,296 combinations.

Compositions and methods for sample analysis based on the address space of fluorophore combinations are described in U.S. Provisional Application No. 62/935,766, entitled "Assay Compositions and Methods Based on Diffusion of Fluorophores," filed Nov. 15, 2019, the contents of which are incorporated herein by reference for all purposes.

Sample droplets and reagent droplets can be synthesized with known populations of fluorescent particles. An example of such a synthesis involves first generating an emulsion of droplets each containing one fluorescent particle of a particular color, and generating another emulsion of droplets each containing one fluorescent particle of another particular color; commercial technology allows the generation of such droplets along with sorting to obtain uniform emulsions. Next, one emulsion is positively electrochemically charged, and the other is negatively electrochemically charged. Mixture of the two emulsions results in binary combinations that result in merged droplets that contain two fluorescent particles (one of each color). This merging process can be repeated to add more fluorescent particles in a controlled manner. This merging process is comparable to the merging process used herein to merge sample droplets with reagent droplets.

Throughout the mixing process, the fluorescent particle may move by Brownian motion.

Brownian motion is a stochastic process that may cause the fluorescent particle to exhibit non-deterministic motion, such as toward and away from the inner wall surface of the droplet, along the inner wall surface of the droplet, or both at the same time.

Figure 21:
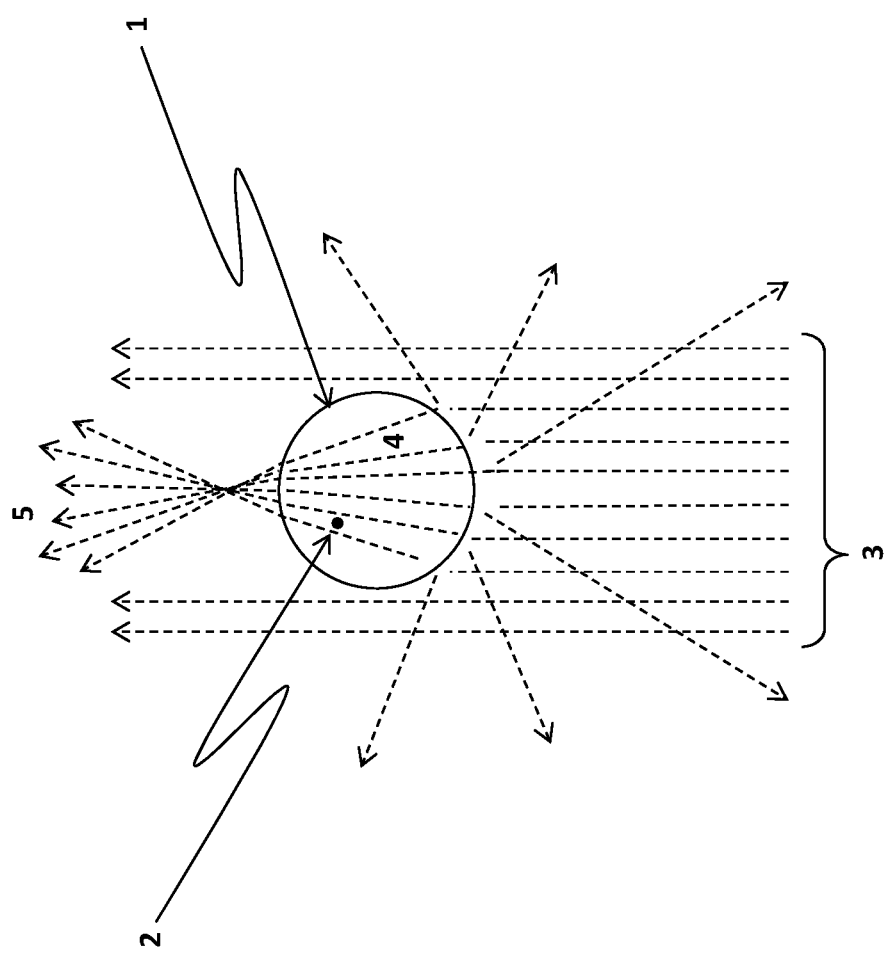
FIG. 21 is a schematic of excitation light rays passing through a droplet, according to certain embodiments of the present disclosures.

The droplets and the host matrix have differing refractive indices. When excitation light is applied, the excitation light may refract and diffract at the refractive index boundaries, as shown in FIG. 21. The excitation light (3) impinges on a droplet (1), and is refracted and diffracted at various angles (4), eventually exiting (5) the droplet (1). This produces an evanescent wave near the surface of the droplets when the excitation light is applied. The evanescent wave consists of an electric field vector and a magnetic field vector.

Due to refraction and diffraction at the surface of each droplet (1), the magnitude of the electric field vector of the excitation light is not uniform across the droplet (1) internal volume. Polarization and coherence of the excitation light may contribute to the electric field vector not being uniform across the droplet (1) internal volume.

Additionally, excitation light absorption due to various components of the sample may also contribute to the magnitude of the electric field vector not being uniform across the droplet (1) internal volume.

As a fluorescent particle (2) is moved by Brownian motion within the droplet (1), the magnitude of its fluorescence may vary with the magnitude of the local electric field vector produced by the evanescent wave. While the fluorescent particle (2) moves in a stochastic manner in and out of the local electric field vector, its fluorescence magnitude follows the stochastic motion. Continual measurement of the stochastic fluorescence emission magnitude, along with statistical analysis of the measurements over time, provides a measure of the magnitude of the stochastic movement. Large fluorescent particles may show small stochastic movement over time, and small fluorescent particles may show large stochastic movement over time. There may be additional information on the movement of the fluorescent particle from the refraction and diffraction of the fluorescence emission light, which may cause the point source to appear circular or semi-circular in the camera images. The circular or semi-circular pattern would be indicative of the location of the fluorescent particle within the droplet. Additionally, the fluorescent particle may be bonded to a magnetic particle, and a magnetic field can be used to pull on the magnetic particle and thereby affect the motion of the fluorescent particle and its corresponding fluorescence. The fluorescent and magnetic particle may be rigidly bonded together as described by (Yu, et al., "A Facile Approach to Fabrication of Bifunctional Magnetic-Optical $Fe_3O_4$@ZnS Microspheres", *Chem. Mater.* 2009, 21, 4892-4898), or may be flexibly bonded as described by Atwood (U.S. Application Publication 2017-0336403). For example, a construct of a magnetic particle and a fluorescent particle may be pulled by a magnetic field along the inner perimeter of a droplet in order to produce a variation in fluorescence that is dependent on analyte binding to the construct.

Additionally, the excitation light can be applied such that the local electric field vector moves past the fluorescent particle, rather than the fluorescent particle moving through the electric field vector. For example, the polarization angle of the excitation light may be rapidly rotated, such that the electric field vector sweeps past the fluorescent particle. This introduces a degree of determinism into the non-deterministic fluorescence emission magnitudes resulting from Brownian motion. This determinism may be analytically useful by allowing correlation between the rotation of the excitation light and the change in the fluorescence emission magnitudes.

Additionally, an external electric field can be applied by positioning the droplets between electrodes set at an oscillating electric potential difference, within the analytic chamber. The electric field would cause charged components of the sample to re-distribute across the droplet and thereby physically distort the droplet from a sphere to a prolate spheroid. The change in the physical shape of the droplet induces a change to the structure of the electric field vector, causing the electric field vector to sweep past the fluorescent particle. This introduces a degree of determinism into the non-deterministic fluorescence emission magnitudes resulting from Brownian motion. This determinism may be analytically useful by allowing correlation between the oscillation of the external electric field and the change in the fluorescence emission magnitudes. The application of the external field would need to be performed with fairly dilute droplets, so that they are not coalesced by the charge differentials.

While the external electric field is causing a physical shape change, the higher density of a quantum dot relative to water causes the quantum dot to move less than the water due to simple inertia. There may also be relative movement due to electrophoretic effects. This results in water molecules flowing past the quantum dot, which hydrodynamically stresses the binding interaction of the analyte with the fluorescent particle. This stress can be scaled upwards, so that weakly bound moieties are stripped off at particular stress levels. This can assist in differentiating non-specific adsorption of sample inert material from the binding interaction with the analyte of interest. A plot of hydrodynamic stress versus fluorescence intensity would thereby yield a graph containing discontinuities that are representative of various binding interactions. The behavior of the interaction of interest can then be singled out.

The movement of the fluorescent particle may be affected by a binding interaction with an analyte. If the analyte is distributed homogeneously, such as solvated uniformly in the water of the merged droplet, then the binding interaction may increase hydrodynamic drag on the fluorescent particle. If the analyte is distributed heterogeneously, such as adhered to the inner wall surface of the merged droplet, then the binding interaction may restrict movement of the fluorescent particle away from the wall or along the wall. The emulsion host matrix and surfactant composition may be selected to optimize adherence of analyte to the inner wall of the droplet, or to avoid it.

Changes in the Brownian movement of the fluorescent particle by a binding interaction may thereby cause changes in the stochastic behavior of the fluorescence emission magnitude. The transition in the stochastic behavior of the fluorescence emission magnitude during each droplet merge event constitutes a measurement signal for the binding interaction of the analyte to the reagent. Since each fluorescent particle is optically tracked individually, variations in the fluorescent particle physical attributes (such as thickness of the protective shell around the semiconductor core) may be nulled by measuring the difference in optical behavior before and after the droplet merge event. This provides enhanced precision in the measurements.

Attachment of a fluorescent particle to one side of an analyte produces an asymmetric geometry, which may affect Brownian movement. Statistical analysis would show that the movement was not purely stochastic, but that it is constrained by the asymmetric geometry. Such statistical analysis may be used to differentiate the Brownian movement of a bound fluorescent particle from that of an un-bound fluorescent particle that has a symmetric geometry, in addition to the magnitude of the Brownian movement.

Presence of the analyte can be determined by the presence of a change in the stochastic behavior of the magnitude of the fluorescence emission.

Concentration of the analyte can be determined by the time required for a change in the stochastic behavior of the magnitude of the fluorescence emission.

Concentration of the analyte can be determined by the proportion of droplets that exhibit a change in the stochastic behavior of the magnitude the fluorescence emission. Generally this applies when the analyte is at sufficiently low concentrations that not all droplets contain an analyte molecule.

Concentration of the analyte can be determined by the degree of saturation of the binding sites on the fluorescent particle, which can be determined by a comparison of the measured change in the stochastic behavior of the magnitude of the fluorescence emission to the expected change in the stochastic behavior of the magnitude of the fluorescence emission.

Association and dissociation constants for the binding interaction between the analyte and the reagent can be determined by varying the size of the droplets. For a sequence of measurements where the merged droplets are successively larger, each containing a fixed number of analyte molecules and fluorescent particles, the effective concentration is successively smaller. Since binding interactions at equilibrium are dependent on concentration, a graph of binding interaction versus concentration yields the association and dissociation constants.

Association and dissociation constants for the binding interaction between the analyte and the reagent can be determined by measuring the duration between a merge event and the occurrence of a change in the stochastic behavior of the magnitude of the fluorescence emission, if the droplets are of known size and composition. For example, if a small sample droplet and a small reagent droplet (having effective high concentrations) merge together, then the duration until the lessening of the stochastic behavior of the magnitude of the fluorescence emission is proportional to the association constant. If that merged small droplet is then merged with a large empty droplet, the effective concentration is greatly lowered, and the duration until the increase of the stochastic behavior of the magnitude of the fluorescence emission is proportional to the dissociation constant.

The fluorescent particle may be a component of a heterogeneous structure containing a magnetic particle, where the magnetic particle is used to move the fluorescent particle into and out of an electric field vector. Such heterogeneous structures are difficult to synthesize with a uniform composition and diffusivity (Yu, et al., "A Facile Approach to Fabrication of Bifunctional Magnetic-Optical $Fe_3O_4$@ZnS Microspheres", *Chem. Mater.* 2009, 21, 4892-4898), the fluorescence bands are broadened, the fluorescence quantum yield is reduced, and the larger size reduces sensitivity for measurements of binding interaction. However, the ability to explicitly control the movement of the fluorescent particle allows correlating the measured fluorescence emission with the asserted movement, which may give data that is less dependent on stochastic movement and thus more precise.

B. Compositions and Methods for Analyzing an Analyte Using Droplets on a Surface In some embodiment, disclosed herein is a method comprising passing a pair of disparate emulsions into an analytic chamber and mixing them together while fluorescence is monitored. One emulsion is formed of droplets of aqueous sample to be analyzed, and the other emulsion is formed of droplets of water containing a fluorescent particle that may bind to an analyte in the sample. The analytic chamber allows the droplets to be distributed along a flat surface. Characteristics of the fluorescence are measured to provide concentration and binding interaction data for various analytes, which can provide useful information about biological samples.

The embodiments in this section are similar to those described in Section II-A, except that the sample droplets and the reagent droplet are not distributed in bulk suspension within the analytic chamber, but rather are distributed along a flat surface within the analytic chamber.

If the droplet floats or sinks within the host matrix, then the droplets may be pressed against the flat upper or lower surface of the analytic chamber.

The analytic chamber may be oriented horizontally, vertically, or at an intermediate angle, in consideration of any floating or sinking properties of the droplets.

Figure 22:
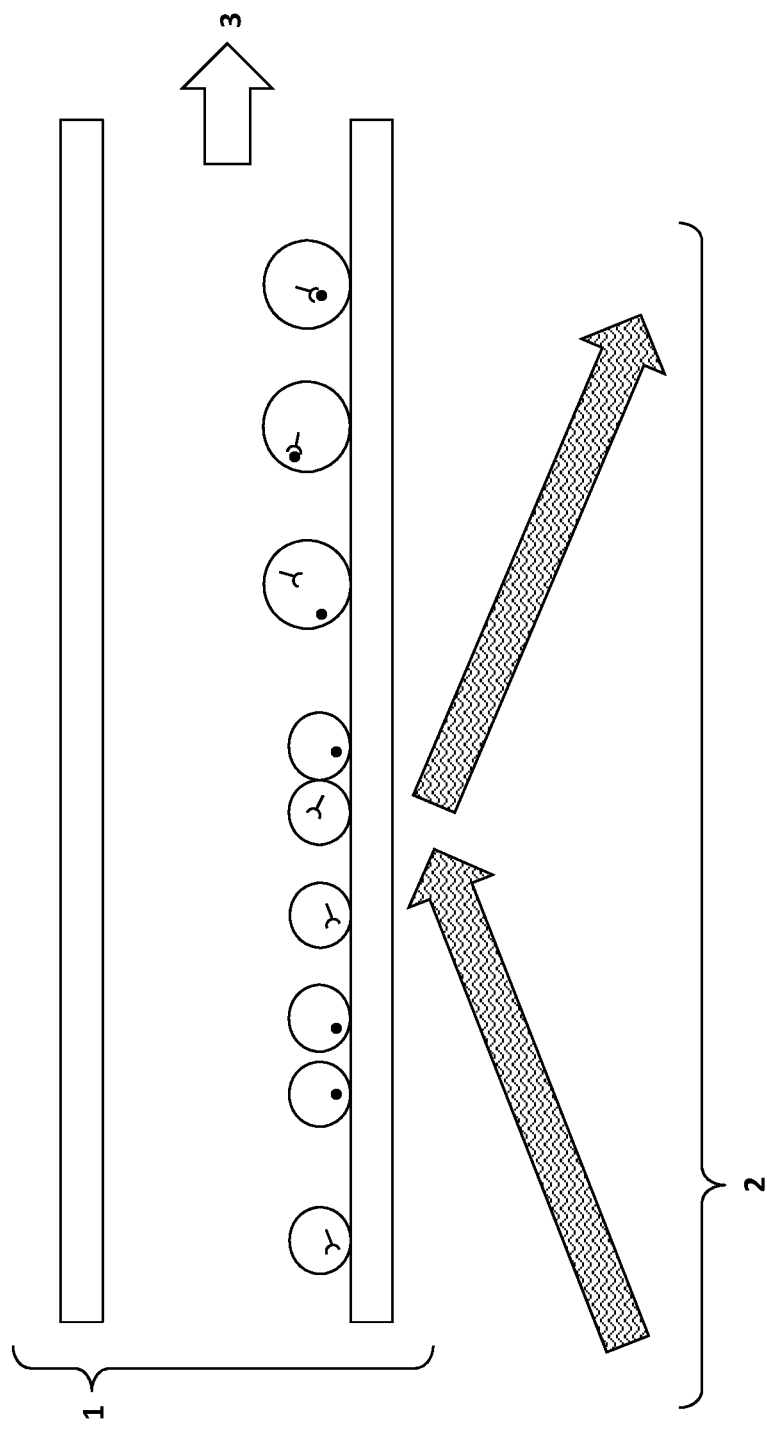
FIG. 22 is a schematic of an analytic cell where excitation light is angled to produce total internal reflection, according to certain embodiments of the present disclosures.

The analytic chamber is constructed such that an excitation light can be applied, as shown in FIG. 22. An analytic chamber (1) contains sample droplets and reagent droplets that merge, eventually flowing out (3) of the analytic chamber (1). Excitation light (2) is applied at an angle such that it exhibits total internal reflection. This generates an evanescent wave that extends into each droplet.

Figure 23:
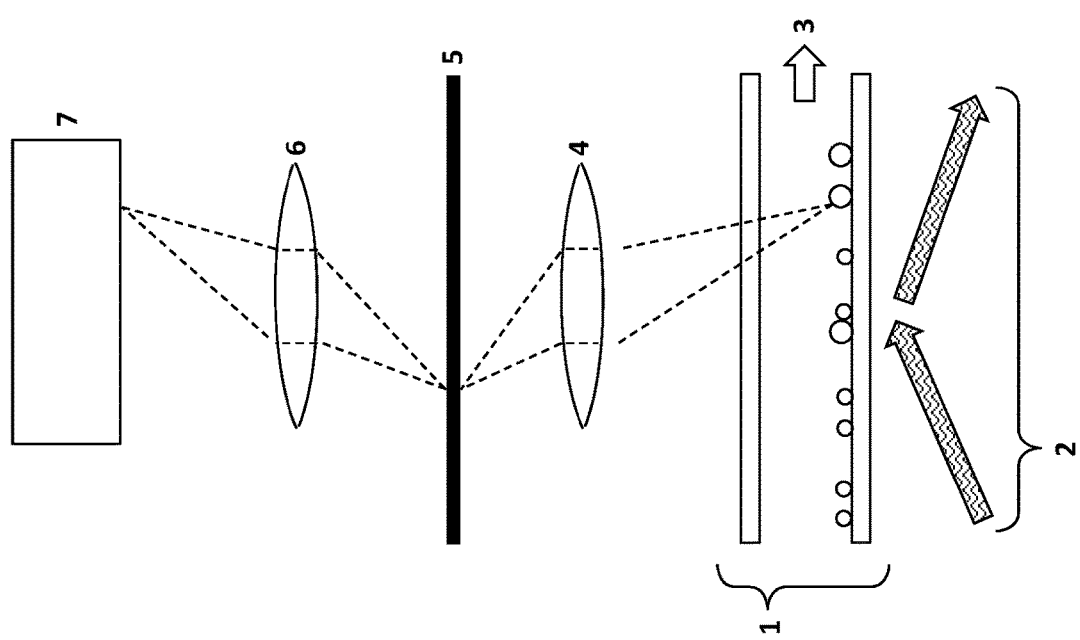
FIG. 23 is a schematic of an optical system for measuring fluorescence emission light from the analytic cell of FIG. 22, according to certain embodiments of the present disclosures.

The analytic chamber is constructed such that fluorescence emission can be emitted to an optic system, as shown in FIG. 23. An analytic chamber (1) contains sample droplets and reagent droplets that merge, eventually flowing out (3) of the analytic chamber (1). Excitation light (2) is applied at an angle such that it exhibits total internal reflection. This generates an evanescent wave that extends into each droplet. A lens (4) focuses the fluorescence emission onto a diffraction grating (5). Another lens (6) focuses the light from the diffraction grating onto a camera (7).

Alternatively, the geometry of the analytic chamber may be made thin along one plane, in order to compress a droplet from a spherical shape to a disk shape.

Figure 24:
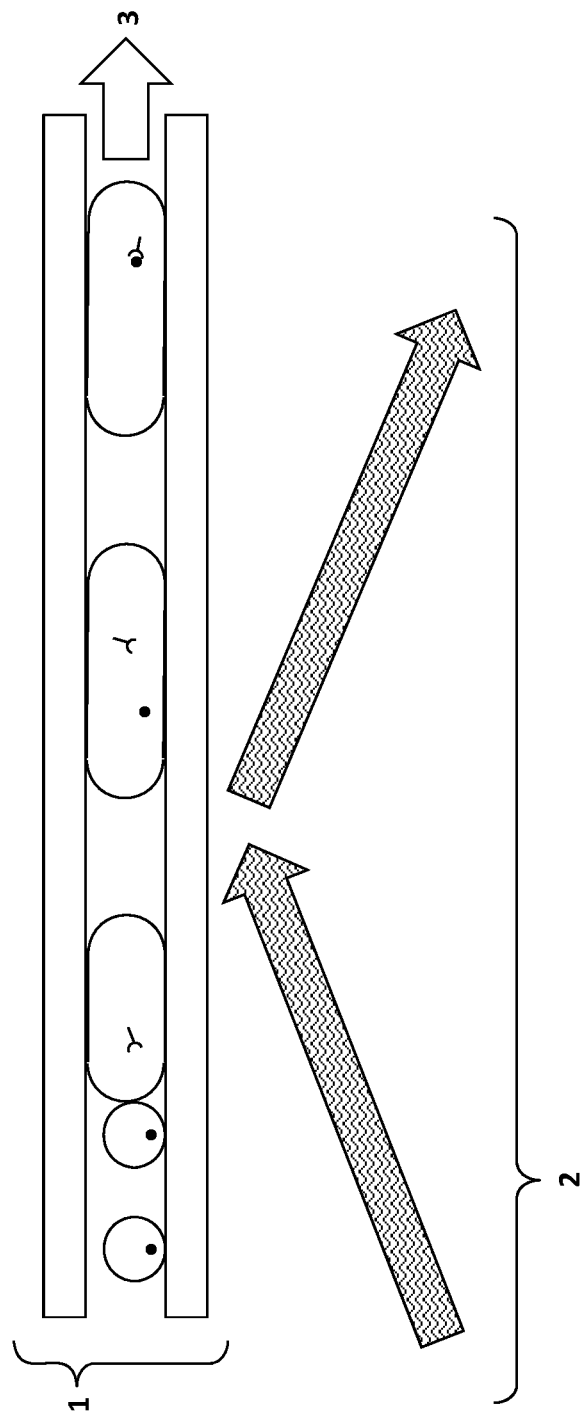
FIG. 24 is a schematic of an analytic cell where excitation light is angled to produce total internal reflection and at least one droplet is compressed into a disk, according to certain embodiments of the present disclosures.

The analytic chamber is constructed such that an excitation light can be applied, as shown in FIG. 24. An analytic chamber (1) contains sample droplets and reagent droplets that merge, eventually flowing out (3) of the analytic chamber (1). Excitation light (2) is applied at an angle to the flat surface of the analytic chamber (and thereby also to the flat surface of a droplet disk), such that total internal reflection occurs. This generates an evanescent wave along the flat surface of the droplet disk that extends into each droplet disk. This allows multiple fluorescent particles to co-exist within a single droplet disk and be individually optically tracked.

Figure 25:
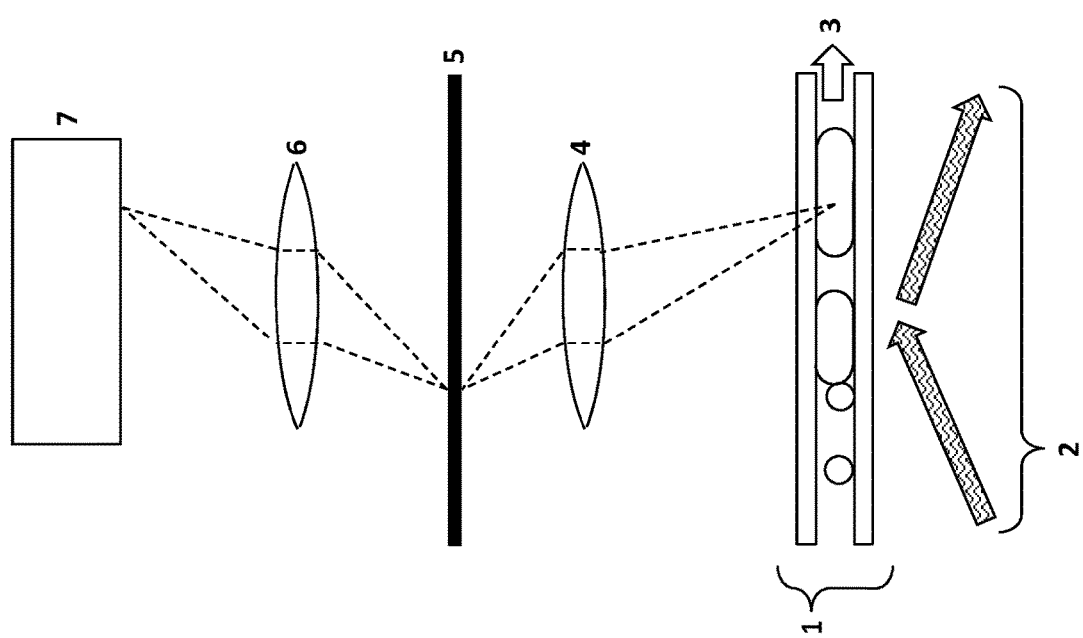
FIG. 25 is a schematic of an optical system for measuring fluorescence emission light from the analytic cell of FIG. 24, according to certain embodiments of the present disclosures.

The analytic chamber is constructed such that fluorescence emission can be emitted to an optic system, as shown in FIG. 25. An analytic chamber (1) contains sample droplets and reagent droplets that merge, eventually flowing out (3) of the analytic chamber (1). Excitation light (2) is applied at an angle to the flat surface of the analytic chamber (and thereby also to the flat surface of a droplet disk), such that total internal reflection occurs. This generates an evanescent wave along the flat surface of the droplet disk that extends into each droplet disk. A lens (4) focuses the fluorescence emission onto a diffraction grating (5). Another lens (6) focuses the light from the diffraction grating onto a camera (7).

Similar to the first Example described above, pairs of droplets within the analytic chamber may merge together to form merged droplets of summed mass, which mixes an analyte with a fluorescent particle and allows a binding interaction to occur. This is referred to as a binary merge event.

Similar to the first Example described above, the binary merge event is caused by one or more of the seven mechanisms described in the discussion of the first example.

Figure 26:
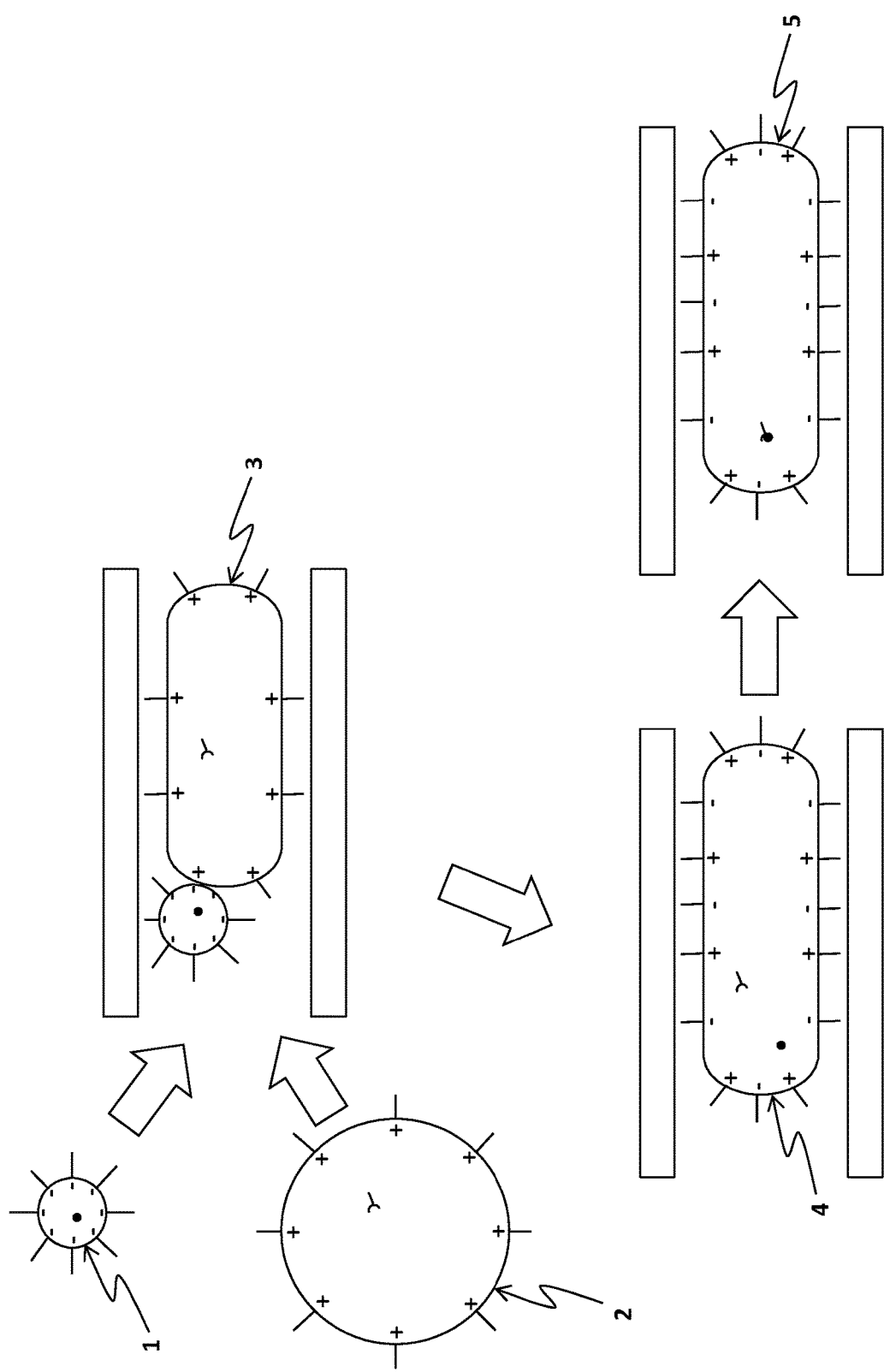
FIG. 26 is a schematic of merging droplets where at least one droplet has been compressed into a disk, according to certain embodiments of the present disclosures.

One of these mechanisms is the electrostatic attraction of oppositely-charged surfactants on the droplet surfaces, as shown in FIG. 26. If the sample droplet surfaces (2) are stabilized with a cationic surfactant and the reagent droplet surfaces (1) are stabilized with an anionic surfactant (or vice versa), then their surfaces charges may cause attraction between a sample droplet and a reagent droplet. This leads to contact of the two droplets (3), followed by a binary merge event (4).

After the binary merge event, the sample and reagent may exhibit a binding interaction (5).

Similar to the first example described above, the second example also includes the features, combinations, and alternatives set forth above in the description of the first Example.

REFERENCES

H. Zhang, L. Sepunaru, S. Sokolov, et al. in "Electrochemistry of single droplets of inverse (water-in-oil) emulsions", Phys. Chem. Chem. Phys. 2017, 19, 15662-15666.

A. Kulesa, J. Kehe, J. Hurtado, P Tawde, P. Blainey, "Combinatorial Drug Discovery in Nanoliter Droplets", Proceedings of the National Academy of Sciences, 115 (26) 6685-6690, 26 Jun. 2018.

David R. Walt, Manuel A. Palacios, and Michael Lacy; U.S. Pat. No. 9,664,667B2 (priority date April 2012).

Gammon, Snow, Shanabrook, Katzer, and Park; "Fine Structure Splitting in the Optical Spectra of Single GaAs Quantum Dots", Phys. Rev. Letters 1996, 76, 3005.

Pouya, Koochesfahani, Snce, Bawendi, and Nocera; "Single Quantum Dot Imaging of Fluid Flow Near Surfaces", Experiments in Fluids, published October 2005.

X. Yu, J. Wan, Y. Shan, K. Chen, and X. Han; "A Facile Approach to Fabrication of Bifunctional Magnetic-Optical Fe3O4@ZnS Microspheres", Chem. Mater. 2009, 21, 4892-4898.

A. Kulesa, J. Kehe, J. Hurtado, P Tawde, P. Blainey, "Combinatorial Drug Discovery in Nanoliter Droplets", Proceedings of the National Academy of Sciences, 115 (26) 6685-6690, 26 Jun. 2018.

All of the references above are incorporated herein by reference.

III. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known. Reference to "about" a value or parameter herein includes (and describes) embodiments that are directed to that value or parameter per se. For example, description referring to "about X" includes description of "X". In certain embodiments, "about X" refers to a value of ±25%, ±10%, ±5%, ±2%, ±1%, ±0.1%, or ±0.01% of X.

As used herein, a composition refers to any mixture of two or more products, substances, or compounds, including cells. It may be a solution, a suspension, liquid, powder, a paste, aqueous, non-aqueous or any combination thereof.

As used herein, a "subject" may include a mammal, such as a human or other animal, and typically is human.

In this application, the term "analyte" may include specific components of complex biological media such as blood, and may consist of proteins, small molecules, or nucleic acids. The term "analyte" may also refer to molecular species that are to be measured in terms of concentration, presence, size, or binding interaction characteristics. The term "analyte" may also refer to a bacterium or virus. The term "analyte" may also refer to molecular species that are to be measured in terms concentration, presence, size, or binding interaction characteristics. The term "analyte" may also refer to a bacterium or virus. The term "analyte" may also refer to a molecular species that is bound to the interface between the aqueous droplet and the water-immiscible host matrix, or between the aqueous droplet and an inner water-immiscible droplet of a secondary emulsion. The term "analyte" may also refer to an oligonucleotide or to a cell such as a blood cell or bacterium, which can be detected by imaging methods.

In this application, the term "analyte binding reagents" may include components that bind or interact with analytes, typically with high selectivity and high affinity In this application, the term "particle" refers to a collection of atoms, e.g., that are fluorescent or magnetic, or both. Typically, a particle is a solid that is substantially insoluble in the context in which it is described.

In this application, a "flocculation" comprising droplets refers to the sticking together of more than two droplets, generally into a large amorphous mass.

In this application, the term "electric field vector" may include the electric field component of an evanescent wave near a transition in refractive index.

In this application, the term "stochastic" may include a non-deterministic behavior, and to non-deterministic behavior that contains a degree of deterministic behavior.

In this application, the term "binding interaction" may include a combination of an analyte and a reagent, having a particular association constant and a particular dissociation constant under particular conditions. It may also refer to an interaction between a reagent and a bacterium or virus. Occurrence of a binding interaction may be observed by detection of various signals as described herein.

A "signal" or "measurement signal" as used herein may include any detectable emission or observable change. Examples include a fluorescence emission, a color change, or a change in size or appearance. In each case, the signal can be detected as described herein or using techniques and devices known in the art, such as a CCD, CMOS, camera, and the like.

IV. EXEMPLARY EMBODIMENTS

Among the provided embodiments are:

Embodiment 1

A method for controlled merging of emulsion droplets, comprising:
 a. providing a first emulsion comprising aqueous droplets containing a first redox species within a first water-immiscible host matrix containing a first electrolyte;
 b. contacting said first emulsion with an anode of an electrochemical cell sufficient to cause charge transfer with the aqueous droplets of the first emulsion;
 c. providing a second emulsion comprising aqueous droplets containing a second redox species within a second water-immiscible host matrix containing a second electrolyte;

d. contacting said second emulsion with a cathode of an electrochemical cell sufficient to cause charge transfer with the aqueous droplets of the second emulsion;
e. mixing said first and second emulsions together to form a combined emulsion, wherein droplets from the first emulsion selectively combine with droplets from the second emulsion to form merged droplets.

Embodiment 2

The method of Embodiment 1, wherein said first emulsion has droplets at least partially coated with a surfactant selected from the group consisting of:
a. nonionic surfactant;
b. amphoteric surfactant;
c. anionic surfactant;
d. cationic surfactant;
e. membrane protein; and
f. no surfactant.

Embodiment 3

The method of Embodiment 1 or 2, wherein said second emulsion has droplets at least partially coated with a surfactant selected from the group consisting of:
a. nonionic surfactant;
b. amphoteric surfactant;
c. anionic surfactant;
d. cationic surfactant;
e. membrane protein; and
f. no surfactant.

Embodiment 4

The method of any one of the preceding Embodiments, wherein said first water-immiscible matrix and said second water-immiscible host matrix are the same, and said water-immiscible host matrix contains a gelling agent that reversibly gels the water-immiscible host matrix below a temperature selected from the group consisting of:
a. 10 degrees Celsius;
b. 20 degrees Celsius;
c. 30 degrees Celsius;
d. 40 degrees Celsius; and
e. 50 degrees Celsius.

Embodiment 5

The method of any one of the preceding Embodiments, wherein said first and/or second redox species are contained within a water-immiscible droplet that is itself within an aqueous droplet of a secondary emulsion.

Embodiment 6

The method of any one of the preceding Embodiments, wherein the aqueous droplets of the first emulsion contain a first cargo, and the aqueous droplets from the second emulsion contain a second cargo, and combining the first and second emulsions selectively forms merged droplets that contain both the first cargo and the second cargo.

Embodiment 7

The method of Embodiment 6, wherein the first cargo and the second cargo are different.

Embodiment 8

The method of Embodiment 6 or 7, wherein the first cargo comprises a compound or particle capable of producing a fluorescent signal.

Embodiment 9

The method of Embodiment 8, wherein the second cargo comprises an analyte.

Embodiment 10

The method of Embodiment 9, wherein the analyte is a protein, bioactive small molecule, or polynucleotide.

Embodiment 11

A method for controlled merging of emulsion droplets, comprising:
a. providing a first emulsion comprising aqueous droplets within a first water-immiscible host matrix, stabilized with a first charged surfactant;
b. providing a second emulsion comprising aqueous droplets within a second water-immiscible host matrix, stabilized with a second surfactant of opposite charge from that of the first charged surfactant;
c. mixing the first and second emulsions together to form a combined emulsion;

wherein droplets from the first emulsion selectively combine with droplets from the second emulsion to form merged droplets.

Embodiment 12

The method of Embodiment 11, wherein said water-immiscible host matrix contains a gelling agent that reversibly gels the water-immiscible host matrix below a temperature selected from the group consisting of:
a. 10 degrees Celsius;
b. 20 degrees Celsius;
c. 30 degrees Celsius;
d. 40 degrees Celsius; and
e. 50 degrees Celsius.

Embodiment 13

A method for controlled merging of emulsion droplets, comprising:
a. providing a first emulsion comprising aqueous droplets;
b. contacting said first emulsion with a positive electrode of an electrostatic cell sufficient to cause electrostatic charging of the aqueous droplets of the first emulsion;
c. providing a second emulsion comprising aqueous droplets;
d. contacting said second emulsion with a negative electrode of an electrostatic cell sufficient to cause electrostatic charging of the aqueous droplets of the second emulsion;
e. mixing of both emulsions together, wherein droplets from the first emulsion selectively combine with droplets from the second emulsion to form merged droplets.

Embodiment 14

The method of Embodiment 13, wherein said first emulsion has droplets coated with a surfactant selected from the group consisting of:

a. nonionic surfactant;
b. amphoteric surfactant;
c. anionic surfactant;
d. cationic surfactant;
e. membrane protein; and
f. no surfactant.

Embodiment 15

The method of Embodiment 13 or 14, wherein said second emulsion has droplets coated with a surfactant selected from the group consisting of:
a. nonionic surfactant;
b. amphoteric surfactant;
c. anionic surfactant;
d. cationic surfactant;
e. membrane protein; and
f. no surfactant.

Embodiment 16

The method of Embodiment 13, 14 or 15, wherein said water-immiscible host matrix contains a gelling agent that reversibly gels the water-immiscible host matrix below a temperature selected from the group consisting of:
a. 10 degrees Celsius;
b. 20 degrees Celsius;
c. 30 degrees Celsius;
d. 40 degrees Celsius; and
e. 50 degrees Celsius.

Embodiment 17

A method for controlled merging of emulsion droplets, comprising:
a. providing a first emulsion comprising aqueous droplets that contain a first cargo and have a positive charge and are suspended in a first water-immiscible host matrix;
b. providing a second emulsion comprising aqueous droplets that contain a second cargo and have a negative charge and are suspended in a second water-immiscible host matrix;
c. mixing said first emulsion and said second emulsion together to form a combined emulsion,
wherein aqueous droplets from the first emulsion selectively combine with aqueous droplets from the second emulsion to form merged droplets that contain both the first cargo and the second cargo.

Embodiment 18

The method of Embodiment 17, wherein said water-immiscible host matrix contains a gelling agent that reversibly gels the water-immiscible host matrix below a temperature selected from the group consisting of:
a. 10 degrees Celsius;
b. 20 degrees Celsius;
c. 30 degrees Celsius;
d. 40 degrees Celsius; and
e. 50 degrees Celsius.

Embodiment 19

A method for controlled merging of emulsion droplets, comprising:
a. providing a first emulsion comprising aqueous droplets containing a first magnetic particle within a first water-immiscible host matrix;
b. providing a second emulsion comprising aqueous droplets containing a second magnetic particle within a second water-immiscible host matrix;
c. mixing said first and second emulsions together to form a combined emulsion;
d. applying an external magnetic field sufficient to produce an attractive force between said first magnetic particle and said second magnetic particle,
wherein droplets from the first emulsion selectively combine with droplets from the second emulsion to form merged droplets.

Embodiment 20

The method of Embodiment 19, wherein said first magnetic particle has an electric charge.

Embodiment 21

The method of Embodiment 19, wherein said second magnetic particle has an electric charge.

Embodiment 22

The method of Embodiment 19, wherein said first emulsion has droplets at least partially coated with a surfactant selected from the group consisting of:
a. nonionic surfactant;
b. amphoteric surfactant;
c. anionic surfactant;
d. cationic surfactant;
e. membrane protein; and
f. no surfactant.

Embodiment 23

The method of Embodiment 19 or 22, wherein said second emulsion has droplets at least partially coated with a surfactant selected from the group consisting of:
a. nonionic surfactant;
b. amphoteric surfactant;
c. anionic surfactant;
d. cationic surfactant;
e. membrane protein; and
f. no surfactant.

Embodiment 24

The method of any one of the preceding Embodiments, wherein said first water-immiscible matrix and said second water-immiscible host matrix are the same, and said water-immiscible host matrix contains a gelling agent that reversibly gels the water-immiscible host matrix below a temperature selected from the group consisting of:
a. 10 degrees Celsius;
b. 20 degrees Celsius;
c. 30 degrees Celsius;
d. 40 degrees Celsius; and
e. 50 degrees Celsius.

Embodiment 25

The method of any one of the preceding Embodiments, wherein said first and/or second magnetic particles are contained within a water-immiscible droplet that is itself within an aqueous droplet of a secondary emulsion.

Embodiment 26

The method of any one of the preceding Embodiments, wherein the aqueous droplets of the first emulsion contain a first cargo, and the aqueous droplets from the second emulsion contain a second cargo, and combining the first and second emulsions selectively forms merged droplets that contain both the first cargo and the second cargo.

Embodiment 27

The method of Embodiment 26, wherein the first cargo and the second cargo are different.

Embodiment 28

The method of Embodiment 26 or 27, wherein the first cargo comprises a compound or particle capable of producing a fluorescent signal.

Embodiment 29

The method of Embodiment 28, wherein the second cargo comprises an analyte.

Embodiment 30

The method of Embodiment 29, wherein the analyte is a protein, bioactive small molecule, or polynucleotide.

Exemplary Instance 1

A method to detect the presence of an analyte in a sample, which comprises:
a. providing a first emulsion that comprises a first aqueous droplet in a first liquid matrix, wherein the first aqueous droplet comprises a portion of the sample;
b. providing a second emulsion that comprises a second aqueous droplet in a second liquid matrix, wherein the second aqueous droplet comprises an analyte interacting reagent (e.g., analyte binding reagent);
c. contacting the first emulsion with the second emulsion to form a combined emulsion under conditions that allow the first aqueous droplet to merge with the second aqueous droplet to form a merged droplet; and
d. detecting a signal generated by a binding interaction of the analyte with the analyte interacting reagent (e.g., analyte binding reagent).

Exemplary Instance 2

The method of Exemplary Instance 1, wherein the first aqueous droplet has a net ionic charge.

Exemplary Instance 3

The method of Exemplary Instance 2, wherein the second aqueous droplet has a net ionic charge that is the opposite of the net ionic charge of the first aqueous droplet.

Exemplary Instance 4

The method of any one of the preceding Exemplary Instances, wherein the first aqueous droplet comprises a first surfactant, optionally wherein the first surfactant is cationic, anionic, nonionic, or amphoteric, and optionally wherein the first surfactant is or comprises a membrane protein.

Exemplary Instance 5

The method of any one of the preceding Exemplary Instances, wherein the second aqueous droplet comprises a second surfactant, optionally wherein the second surfactant is cationic, anionic, nonionic, or amphoteric, and optionally wherein the second surfactant is or comprises a membrane protein.

Exemplary Instance 6

The method of any one of the preceding Exemplary Instances, wherein at least one of the first aqueous droplet and the second aqueous droplet is stabilized by a surfactant.

Exemplary Instance 7

The method of any of Exemplary Instances 4-6, wherein the first surfactant is ionic.

Exemplary Instance 8

The method of Exemplary Instance 7, wherein the second surfactant is ionic and has a charge that is the opposite of the charge of the first surfactant.

Exemplary Instance 9

The method of any of the preceding Exemplary Instances, wherein the merged droplet comprises a fluorescent label or a fluorescent particle.

Exemplary Instance 10

The method of any one of Exemplary Instances 1-9, wherein the merged droplet comprises a magnetic particle.

Exemplary Instance 11

The method of any one of the preceding Exemplary Instances, wherein the first liquid matrix is not miscible with water.

Exemplary Instance 12

The method of any one of the preceding Exemplary Instances, wherein the second liquid matrix is not miscible with water.

Exemplary Instance 13

The method of any one of the preceding Exemplary Instances, wherein mixing of the first emulsion and the second emulsion occurs in an analytic chamber.

Exemplary Instance 14

The method of any one of the preceding Exemplary Instances, wherein contacting said first emulsion and said second emulsion comprises mixing:
a. adjacent streams of the first emulsion and the second emulsion; or
b. transverse streams of the first emulsion and the second emulsion; or c. perpendicular streams of the first emulsion and the second emulsion; or
d. oblique streams of the first emulsion and the second emulsion; or
e. opposed streams of the first emulsion and the second emulsion; or
f. concentric streams of the first emulsion and the second emulsion.

Exemplary Instance 15

The method of any one of the preceding Exemplary Instances, wherein contacting said first emulsion and said second emulsion comprises mixing streams of the first emulsion and the second emulsion and at least one demulsifying agent.

Exemplary Instance 16

The method of any one of the preceding Exemplary Instances, wherein contacting said first emulsion and said second emulsion comprises mixing streams of the first emulsion and the second emulsion and at least one additional surfactant.

Exemplary Instance 17

The method of any one of the preceding Exemplary Instances, wherein the signal generated by binding of the analyte with the analyte interacting reagent (e.g., analyte binding reagent) is a fluorescent signal.

Exemplary Instance 18

The method of any one of the preceding Exemplary Instances, wherein the signal is induced by excitation light having at least one property selected from the group consisting of:
a. non-polarized;
b. linearly polarized;
c. circularly polarized;
d. elliptically polarized;
e. non-coherent;
f. coherent;
g. continuous;
h. pulsed;
i. applied at a single incident angle; and
j. applied at a set of incidence angles.

Exemplary Instance 19

The method of any of the preceding Exemplary Instances, wherein an external electric field is applied to the combined emulsion with a magnitude sufficient to modify the distribution of the electric field vector of an evanescent wave within each droplet and thereby affect the fluorescence emission, in a manner selected from the group consisting of:
a. a constant electric field in a constant direction;
b. a pulsed electric field in a constant direction;
c. an oscillating electric field in a constant direction;
d. a constant field electric switching between multiple directions;
e. a pulsed electric field switching between multiple directions; and
f. an oscillating electric field switching between multiple directions.

Exemplary Instance 20

The method of any one of the preceding Exemplary Instances, wherein an external electric field is applied to the combined emulsion with a magnitude sufficient to induce a distortion of the merged droplets, in a manner selected from the group consisting of:
a. a constant electric field in a constant direction;
b. a pulsed electric field in a constant direction;
c. an oscillating electric field in a constant direction;
d. a constant field electric switching between multiple directions;
e. a pulsed electric field switching between multiple directions; and
f. an oscillating electric field switching between multiple directions.

Exemplary Instance 21

The method of Exemplary Instance 18, wherein said excitation light is only applied to the combined emulsion, and the signal is a fluorescence emission and is only detected after the merge event has occurred.

Exemplary Instance 22

A method for detection of an analyte interacting with an analyte interacting reagent (e.g., analyte binding reagent), comprising:
a. providing a first emulsion comprising aqueous sample droplets within a water-immiscible host matrix, stabilized with a first charged surfactant, wherein the sample droplets comprise the analyte;
b. providing a second emulsion comprising aqueous reagent droplets within a water-immiscible host matrix, stabilized with a second surfactant of opposite charge from the charge of the first charged surfactant, wherein the reagent droplets contain one or more fluorescent particles, where each fluorescent particle has a unique analyte interacting reagent (e.g., analyte binding reagent) surface;
c. mixing of both emulsions together at a flat surface in an analytic chamber and allowing said droplets to merge into merged droplets;
d. asserting excitation light at an angle sufficient to produce total internal reflection at said flat surface during said mixing process sufficient to cause fluorescence of the said fluorescent particle, wherein said fluorescence is dependent on fluorescent particle position within the electric field vector of an evanescent wave that arises from a refractive index difference between said flat surface and the droplet;
e. detecting and/or measuring the magnitude of the fluorescence emission during said mixing process; and
f. determining the identity of the analyte interacting reagent (e.g., analyte binding reagent) used within each droplet from the pattern of fluorescent emission wavelengths from each droplet; and
wherein a change in the stochastic behavior of the magnitude of the fluorescence emission provides an indication of analyte presence, concentration, and/or binding interaction.

Exemplary Instance 23

The method of Exemplary Instance 22, wherein said aqueous sample droplet and said reagent droplet are electrostatically charged with opposing charges.

Exemplary Instance 24

The method of Exemplary Instance 22, wherein said droplets have additional components selected from the group consisting of:
a. said aqueous sample droplets each contain at least one fluorescent particle;
b. said aqueous reagent droplets each contain more than one fluorescent particle;
c. said aqueous sample droplets and said aqueous reagent droplets each contain at least one fluorescent particle;
d. said aqueous sample droplets each contain at least one magnetic particle;
e. said aqueous reagent droplets each contain more than one magnetic particle; and
f. said aqueous sample droplets and said aqueous reagent droplets each contain at least one magnetic particle.

Exemplary Instance 25

The method of Exemplary Instance 22, wherein said analytic chamber performs said mixing of said aqueous sample droplets and said reagent droplets by flowing streams in a manner selected from the group consisting of:
a. adjacent streams of aqueous sample droplets and aqueous reagent droplets in their respective water-immiscible host matrices;
b. transverse streams of aqueous sample droplets and aqueous reagent droplets in their respective water-immiscible host matrices;
c. perpendicular streams of aqueous sample droplets and aqueous reagent droplets in their respective water-immiscible host matrices;
d. oblique streams of aqueous sample droplets and aqueous reagent droplets in their respective water-immiscible host matrices;
e. opposed streams of aqueous sample droplets and aqueous reagent droplets in their respective water-immiscible host matrices;
f. concentric streams aqueous sample droplets and aqueous reagent droplets in their respective water-immiscible host matrices;
g. streams of aqueous sample droplets and aqueous reagent droplets in their respective water-immiscible host matrices combined with one or more streams of demulsification agents; and
h. streams of aqueous sample droplets and aqueous reagent droplets in their respective water-immiscible host matrices combined with one or more streams of surfactants.

Exemplary Instance 26

The method of Exemplary Instance 22, wherein said excitation light has properties selected from the group consisting of:
a. non-polarized;
b. linearly polarized;
c. circularly polarized;
d. elliptically polarized;
e. non-coherent;
f. coherent;
g. continuous;
h. pulsed;
i. applied at a single incident angle; and
j. applied at a set of incidence angles.

Exemplary Instance 27

The method of Exemplary Instance 22, wherein an external electric field is applied to said emulsions with a magnitude sufficient to modify the distribution of the electric field vector of an evanescent wave within each droplet and thereby affect the fluorescence emission, in a manner selected from the group consisting of:
a. a constant electric field in a constant direction;
b. a pulsed electric field in a constant direction;
c. an oscillating electric field in a constant direction;
d. a constant field electric switching between multiple directions;
e. a pulsed electric field switching between multiple directions; and
f. an oscillating electric field switching between multiple directions.

Exemplary Instance 28

The method of Exemplary Instance 22, wherein an external electric field is applied to said emulsions with a magnitude sufficient to induce a distortion of the spherical droplets into prolate spheroids and thereby cause hydrodynamic stress to binding interactions between the fluorescent particle and moieties bound to it, in a manner selected from the group consisting of:
a. a constant electric field in a constant direction;
b. a pulsed electric field in a constant direction;
c. an oscillating electric field in a constant direction;
d. a constant field electric switching between multiple directions;
e. a pulsed electric field switching between multiple directions; and
f. an oscillating electric field switching between multiple directions.

Exemplary Instance 29

The method of Exemplary Instance 22, wherein said excitation light is only applied after the merge event has occurred, and said magnitude of the fluorescence emission is only measured after the merge event has occurred.

Exemplary Instance 30

The method of Exemplary Instance 22, wherein compression into a disk is applied to items selected from the group consisting of:
a. said sample droplets;
b. said reagent droplets; and
c. said merged droplets.

Exemplary Instance 31

The method of Exemplary Instance 22, wherein floating or sinking to said flat surface occurs for items selected from the group consisting of:
a. said sample droplets;
b. said reagent droplets; and
c. said merged droplets.

Exemplary Instance 32

A method for detection of an interaction between an analyte in a sample and an analyte interacting reagent (e.g., analyte binding reagent), wherein the method comprises:

a. providing a first aqueous emulsion comprising droplets containing a portion of the sample in a water-immiscible host matrix, wherein the emulsion is stabilized with a charged surfactant;
b. providing a second aqueous emulsion comprising one or more analyte interacting reagent (e.g., analyte binding reagent)s in droplets in a water-immiscible host matrix, where each analyte interacting reagent (e.g., analyte binding reagent) is on the surface of a fluorescent particle, wherein the second aqueous emulsion is stabilized with a surfactant having the opposite charge from that of the charged surfactant in the first aqueous emulsion;
c. mixing the first and second aqueous emulsions together to form a combined emulsion under conditions where droplets from the first emulsion can combine with droplets from the second emulsion to form merged droplets;
d. directing excitation light to the combined emulsion during and/or after mixing, sufficient to cause fluorescence of said fluorescent particles, wherein said fluorescence is dependent on the position of each fluorescent particle within the electric field vector of an evanescent wave that arises from a refractive index difference between the host matrix and the droplet;
e. detecting the fluorescence emission and/or measuring the magnitude of the fluorescence emission from the merged droplets; and
f. determining the identity of each affinity binding reagent within each merged droplet from the pattern of fluorescent emission wavelengths from each merged droplet;

wherein a change in the stochastic behavior of the magnitude of the fluorescence emission provides an indication of analyte presence, concentration, and/or binding interaction.

Exemplary Instance 33

The method of Exemplary Instance 32, wherein said aqueous sample droplet and said reagent droplet are electrostatically charged with opposing charges.

Exemplary Instance 34

The method of Exemplary Instance 32, wherein said droplets have additional components selected from the group consisting of:
a. said aqueous sample droplets each contain at least one fluorescent particle;
b. said aqueous reagent droplets each contain more than one fluorescent particle;
c. said aqueous sample droplets and said aqueous reagent droplets each contain at least one fluorescent particle;
d. said aqueous sample droplets each contain at least one magnetic particle;
e. said aqueous reagent droplets each contain more than one magnetic particle; and
f. said aqueous sample droplets and said aqueous reagent droplets each contain at least one magnetic particle.

Exemplary Instance 35

The method of Exemplary Instance 32, wherein said analytic chamber performs said mixing of said aqueous sample droplets and said reagent droplets by flowing streams in a manner selected from the group consisting of:

a. adjacent streams of aqueous sample droplets and aqueous reagent droplets in their respective water-immiscible host matrices;
b. transverse streams of aqueous sample droplets and aqueous reagent droplets in their respective water-immiscible host matrices;
c. perpendicular streams of aqueous sample droplets and aqueous reagent droplets in their respective water-immiscible host matrices;
d. oblique streams of aqueous sample droplets and aqueous reagent droplets in their respective water-immiscible host matrices;
e. opposed streams of aqueous sample droplets and aqueous reagent droplets in their respective water-immiscible host matrices;
f. concentric streams of aqueous sample droplets and aqueous reagent droplets in their respective water-immiscible host matrices;
g. streams of aqueous sample droplets and aqueous reagent droplets in their respective water-immiscible host matrices combined with one or more streams of demulsification agents; and
h. streams of aqueous sample droplets and aqueous reagent droplets in their respective water-immiscible host matrices combined with one or more streams of surfactants.

Exemplary Instance 36

The method of Exemplary Instance 32, wherein said excitation light properties selected from the group consisting of:
a. non-polarized;
b. linearly polarized;
c. circularly polarized;
d. elliptically polarized;
e. non-coherent;
f. coherent;
g. continuous;
h. pulsed;
i. applied at a single incident angle; and
j. applied at a set of incidence angles.

Exemplary Instance 37

The method of Exemplary Instance 32, wherein an external electric field is applied to said emulsions with a magnitude sufficient to modify the distribution of the electric field vector of an evanescent wave within each droplet and thereby affect the fluorescence emission, in a manner selected from the group consisting of:
a. a constant electric field in a constant direction;
b. a pulsed electric field in a constant direction;
c. an oscillating electric field in a constant direction;
d. a constant field electric switching between multiple directions;
e. a pulsed electric field switching between multiple directions; and
f. an oscillating electric field switching between multiple directions.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing an analyte, comprising:
contacting (i) a first emulsion comprising a first aqueous droplet in a first liquid matrix, with (ii) a second emulsion comprising a second aqueous droplet in a second liquid matrix, wherein the first aqueous droplet comprises an analyte and the second aqueous droplet comprises a reagent, under conditions that allow the first aqueous droplet to merge with the second aqueous droplet to form a merged droplet,
wherein an interaction or a reaction in the merged droplet involving the analyte and the reagent generates a detectable signal, and
wherein merging of the first and second aqueous droplets is controlled, and the controlled merging is provided by:
(i) the first aqueous droplet comprising a first redox species and the first liquid matrix comprising a first electrolyte, the second aqueous droplet comprising a second redox species and the second liquid matrix comprising a second electrolyte, wherein the first and second aqueous droplets are each contacted with an electrode to cause charge transfer between the aqueous droplet and the electrode;
(ii) the first emulsion stabilized with a first charged surfactant, and the second emulsion stabilized with a second charged surfactant of opposite charge from that of the first charged surfactant;
(iii) contacting the first emulsion with a positive electrode sufficient to cause electrostatic charging of the first aqueous droplet, and contacting the second emulsion with a negative electrode sufficient to cause electrostatic charging of the second aqueous droplet; and/or
(iv) the first aqueous droplet comprising a first magnetic particle, the second aqueous droplet comprising a second magnetic particle, wherein an external magnetic field is applied to produce an attractive force between said first magnetic particle and said second magnetic particle.

2. The method of claim 1, wherein the detectable signal is detected for analyzing the presence or absence, an amount or concentration, and/or an activity of the analyte in a sample.

3. The method of claim 1, wherein the first aqueous droplet has a first net ionic charge, and the second aqueous droplet has a second net ionic charge that is the opposite of the first net ionic charge.

4. The method of claim 1, wherein the first aqueous droplet comprises a first charged surfactant and the second aqueous droplet comprises a second charged surfactant, and wherein the second surfactant is of opposite charge from the charge of the first charged surfactant.

5. The method of claim 1, wherein the reagent comprises a fluorescent label.

6. The method of claim 1, wherein the reagent comprises a magnetic label.

7. The method of claim 1, wherein the contacting step comprises mixing streams of the first emulsion and the second emulsion and at least one demulsifying agent.

8. The method of claim 1, wherein the contacting step comprises mixing streams of the first emulsion and the second emulsion and at least one surfactant.

9. The method of claim 1, wherein the detectable signal comprises a fluorescent signal, which is optionally induced by a non-polarized excitation light, a linearly polarized excitation light, a circularly polarized excitation light, an elliptically polarized excitation light, a non-coherent excitation light, a coherent excitation light, a continuous excitation light, a pulsed excitation light, an excitation light applied at a single incident angle, or an excitation light applied at a set of incidence angles.

10. The method of claim 1, further comprising applying an external electric field to the merged droplet to modify the distribution of the electric field vector of an evanescent wave within each droplet and thereby affect fluorescence emission.

11. The method of claim 1, further comprising applying an external electric field to distort the merged droplet.

12. The method of claim 1, wherein the reagent comprises a fluorescent particle and is capable of specifically binding to the analyte.

13. The method of claim 12, wherein the first and second emulsions are mixed on a surface in an analytical chamber, thereby allowing the first and second aqueous droplets to form the merged droplet on the surface, and allowing the reagent to specifically bind to the analyte in the merged droplet.

14. The method of claim 13, further comprising applying an excitation light at an angle sufficient to produce total internal reflection on the surface during said mixing process sufficient to cause fluorescence of the fluorescent particle, wherein said fluorescence is dependent on fluorescent particle position within the electric field vector of an evanescent wave that arises from a refractive index difference between said flat surface and the aqueous droplet.

15. The method of claim 14, further comprising:
detecting and/or measuring the magnitude of the fluorescence emission during said mixing process; and
determining the identity of reagent used within each droplet from the pattern of fluorescent emission wavelengths from each droplet,
wherein a change in the stochastic behavior of the magnitude of the fluorescence emission provides an indication of analyte presence/absence, amount or concentration, and/or binding interaction.

16. The method of claim 12, wherein the first and second emulsions are mixed to form a combined emulsion wherein the merged droplet is in suspension in the combined emulsion.

17. The method of claim 16, further comprising applying an excitation light during said mixing process sufficient to cause fluorescence of the fluorescent particle, wherein said fluorescence is dependent on fluorescent particle position within the electric field vector of an evanescent wave that arises from a refractive index difference between said liquid matrix and the aqueous droplet.

18. The method of claim 17, further comprising:
detecting and/or measuring the magnitude of the fluorescence emission during said mixing process; and
determining the identity of reagent used within each droplet from the pattern of fluorescent emission wavelengths from each droplet,
wherein a change in the stochastic behavior of the magnitude of the fluorescence emission provides an indication of analyte presence/absence, amount or concentration, and/or binding interaction.

19. A method for controlled merging of emulsion droplets, comprising contacting (i) a first emulsion comprising a first aqueous droplet in a first liquid matrix, with (ii) a second emulsion comprising a second aqueous droplet in a second liquid matrix, under conditions that allow the first aqueous droplet to merge with the second aqueous droplet to form a merged droplet, wherein the merging is controlled and is provided by:
- (i) the first aqueous droplet comprising a first redox species and the first liquid matrix comprising a first electrolyte, the second aqueous droplet comprising a second redox species and the second liquid matrix comprising a second electrolyte, wherein the first and second aqueous droplets are each contacted with an electrode to cause charge transfer between the aqueous droplet and the electrode;
- (ii) the first emulsion stabilized with a first charged surfactant, and the second emulsion stabilized with a second charged surfactant of opposite charge from that of the first charged surfactant;
- (iii) contacting the first emulsion with a positive electrode sufficient to cause electrostatic charging of the first aqueous droplet, and contacting the second emulsion with a negative electrode sufficient to cause electrostatic charging of the second aqueous droplet; and/or
- (iv) the first aqueous droplet comprising a first magnetic particle, the second aqueous droplet comprising a second magnetic particle, wherein an external magnetic field is applied to produce an attractive force between said first magnetic particle and said second magnetic particle.

* * * * *